United States Patent [19]

Leonard et al.

[11] Patent Number: 5,518,880
[45] Date of Patent: May 21, 1996

[54] METHODS FOR DIAGNOSIS OF XSCID AND KITS THEREOF

[75] Inventors: Warren J. Leonard, Bethesda; Masayuki Noguchi, Rockville; O. Wesley McBride, Bethesda, all of Md.

[73] Assignee: The United States of America as represented by the Secretary of the Department of Health and Human Services, Washington, D.C.

[21] Appl. No.: 31,143

[22] Filed: Mar. 12, 1993

[51] Int. Cl.⁶ .............................. C12Q 1/68; C07H 21/04
[52] U.S. Cl. ..................... 435/6; 435/172.3; 435/320.1; 435/810; 436/501; 536/22.1; 536/23.1; 536/24.1; 536/24.3; 536/24.31; 536/24.32; 536/24.33; 935/9; 935/13; 935/77; 935/78
[58] Field of Search .......................... 435/6, 7.1, 69.1, 435/172.3, 69.52, 320.1, 810; 436/501, 63; 424/85.2, 132.1, 158.1; 536/22.1, 23.1, 24.1, 24.3–.33; 935/9, 13, 77, 78

[56] References Cited

U.S. PATENT DOCUMENTS 5,106,728  4/1992  Conley et al. ........................ 435/6

OTHER PUBLICATIONS

Noguchi et al. (1993) Cell, vol. 73, pp. 147–157.
Cao et al. (1993) Proc. Nat'l Acad Sci (USA), vol. 90, pp. 8464–8468.
Pediatric Research Abstract No. 1005, Apr. 1989, vol. 25, No. 4/Part 2.
Gelfand, E. W. and Dosch, H. M. *Birth Defects: Original Article Series* 19 (3): 65–72 (1983).
Puck, J. M., et al. *J. Clin. Invest.* 79: 1395–1400 (1987).
Conley, M. E., et al. *Proc. Natl. Acad. Sci. USA* 85: 3090–3094 (1988).
Cooper, M. D. and Butler, J. L. *Fundamentals Immunology*, (Paul, W. E. editor, Raven Press, New York), pp. 1034–1039 (1989).
Pahwa, R., et al. *Proc. Natl. Acad. Sci. USA* 86: 5069–5073 (1989).

Weinberg, M. D. and Parkman, R. *N. Engl. J. Med.* 322 (24): 1718–1723 (1990).
Chatila, T. et al. *Proc. Natl. Acad. Sci. USA* 87: 10033–10037 (1990).
Goodship, J., et al. *Clin. Exp. Immunol.* 83: 4–9 (1991).
Felsburg, P. J. and Somberg, R. L. *Immuno. Rev.* 3: 277–303 (1992).
Puck, J. M., et al. *Am. J. Hum. Genet.* 50: 742–748 (1992).
Hendriks, R. W., et al. *Clin. Genetics* 42(3): 114–121 (1992).
Conley, M. E. *Annu. Rev. Immunol.* 10: 215–238 (1992).
Takeshita, T., et al. *Intl. Immunology* 2(5): 477–480 (1990).
Sugamura, K., et al. *Lymph. Res.* 9(4): 539–542 (1990).
Asao, H., et al. *FEBS Letters* 304: 141–145 (1992).
Takeshita, T., et al. *Science* 257: 379–382 (1992).
Voss, S. D., et al. *J. Exp. Med.* 176: 531–541 (1992).
Zurawski, S. M. and Zurawski, G. *EMBO Journal* 11(11):3905–3910 (1992).

*Primary Examiner*—W. Gary Jones
*Assistant Examiner*—Ardin H. Marschel
*Attorney, Agent, or Firm*—Morgan & Finnegan

[57] ABSTRACT

The present invention provides a method for diagnosing XSCID in a male subject or determining whether a female subject is a carrier of XSCID which comprises determining whether the male or female subject possesses a mutated IL-2Rγ gene, the presence of the mutated IL-2Rγ gene being indicative that the male subject has XSCID or the female subject is a carrier of XSCID. The present invention also provides a method for diagnosing XSCID in a subject which comprises determining whether the subject possesses a truncated IL-2Rγ protein, the presence of the truncated IL-2Rγ protein being indicative of XSCID. The present invention further provides kits for diagnosing XSCID in a male subject or determining whether a female subject is a carrier of XSCID. The present invention still further provides methods for treating XSCID and a method for monitoring therapy. Lastly, the present invention provides a promoter which regulates expression of IL-2Rγ, a vector comprising a DNA molecule operably linked to the promoter, a prokaryotic or eukaryotic cell host stably transformed or transfected with the vector, and a transgenic animal comprising a gene regulated by the promoter or a transgenic animal comprising a mutant IL-2Rγ gene.

44 Claims, 8 Drawing Sheets

*Hind* III
AAGCTT|GAAGCTAGTATTGTTGTTCCTCCATTTCTAGAATATTTTGTATTATAAGTCAC    -547
ACTTCCTCGCCAGTCTCAACAGGACCCAGTCAGGCAGCTCAGGAGCTAAGGGTGGGTATTCTG    -487
GTTTGGATTAGATCAGAGGAAAGAGACAGCTGTATATGTGCCCACAGGAGCCAAGACGGTAT    -427
TTTCCATCCTCCCAAAAACAGTATGAGCTTTGACAGAGATTTAAGGGTGACCAAGTCAAG    -367
GAAGAGGCATGGCATAGAACGGTGATGTCGGGGGTGGGGGTTCAGAACTTCCATTATAG    -307
AAGGTAATGATTTAGAGGAGAAGGTGTTGAGAATGGTGCTAGTGGTAGTGAACAGATCC    -247
                                                  *Ple* I
TTCCCAGGATCTAGGTGGGCTGAGGATTTTT|GAGTC|TGTGACACTATTGTATATCCAGCT    -187
TTAGTTTCTGTTTACCACCTTACAGCAGCACCTAATCTCCTAGAGGACTTAGCCCGTGTC    -127
ACACAGCACATATTGCCACACCCTGTAAAGCCCTGGTTATAAGGTTCTTTCCACCGG    -67
AAGCTATGACAGAGGAAACGTGTGGGTGGGGAGGGTAGTGGGTGAGGGACCCAGGTTCC    -7
                                                        +1
TGACA<u>A</u>GACAGACTACACCCAGGAATGAAGAGCAAGCGCCATGTTGAAGCCATCATTA    +54
                                 MetLeuLysProSerLeu
CCATTCACATCCCTCTTATTCCTGCAGCTGCCCCTGCTGGGAGTGGGCTGAACACGACA    +114
ProPheThrSerLeuLeuPheLeuGlnLeuProLeuLeuGlyValGlyLeuAsnThrThr
ATTCTGACGCCAATGGGAATGAAGAGACACCACAGCTG|GTGGGAAATCTGGGACTGGAGGG
IleLeuThrProAsnGlyAsnGlyAspThrThrAla
                                         *Bgl* II
GGCTGGTGAGAGGGTGGCTGTGGGAAGGGCCGTACAG|AGATCT|GGTGCCTGCCACTGG
CCATTACAATCATGTGGGCAGAATTGAAAAGTGGAGTGGGAAGGGCAAGGGGAGGGTTC
CCTCCCT.........

FIG. 5

METHODS FOR DIAGNOSIS OF XSCID AND KITS THEREOF

Severe combined immunodeficiency diseases (SCIDs) represent a spectrum of disorders characterized by profound defects of both cellular and humoral immunity (Cooper, M. D. and Butler, J. L. *Fundamental Immunology*, (Paul, W. E., editor, Raven Press, New York), pp. 1034–1039 (1989); Gelfand, E. W. and Dosch, H. M. *Birth Defects: Original Article Series* 19(3): 65–72 (1983); Conley, M. E. *Annu. Rev. Immunol.* 10: 215–238 (1992)). One in every $10^5$ to $10^6$ live births are affected by these diseases. Infants with SCID usually become ill in the first few months of life. While their growth and development may initially proceed normally, infections leading to cessation of growth soon become evident (Cooper, M. D. and Butler, J. L., supra, at 1034). Individuals with SCID are vulnerable to virtually every type of pathogenic microorganism, even those that rarely cause disease in normal individuals (Cooper, M. D. and Butler, J. L., supra, at 1034). Candida fungal infection of mucocutaneous surfaces is often the first indication of immunodeficiency, followed by intractable diarrhea and pneumonia (Cooper, M. D. and Butler, J. L., supra, at 1034). The majority of infected infants die before their first birthday.

Classical SCID ("Swiss-type agammaglobulinemia") is characterized by the absence of both T and B cells, presumably related to a defect affecting the lymphocytic stem cell. Autosomal recessive forms of SCID result from deficiencies of adenosine deaminase (ADA) or purine nucleoside phosphorylase (PNP), the inability to express class II molecules of the major histocompatibility complex ("Bare Lymphocyte Syndrome"), or defective IL-2 production. Other autosomal recessive forms have no known defect (Cooper, M. D. and Butler, J. L., supra, at 1034–1037; Gelfand, E. W. and Dosch, H. M., supra, at 66–67; Conley, supra, at 215–238).

X-linked severe combined immunodeficiency (XSCID) accounts for approximately half of all cases of SCID. This form of SCID is inherited in an X-linked fashion. XSCID is characterized by an absence of T-cells and histologic evidence of hypoplastic and abnormal differentiation of the thymic epithelium. Levels of B-cells are normal or even elevated, and therefore patients are only mildly lymphopenic (Cooper, M. D. and Butler, J. L., supra, at 1037; Gelfand, E. W. and Dosch, H. M., supra, at 66–70; Conley, M. E., supra, at 226–227). Since the B-cells are not functional, these males are hypo- or agammaglobulinemic.

There also is evidence to suggest that there might be intrinsic B-cell defects in XSCID. X chromosome inactivation patterns from mothers of children with XSCID provide support for a component of B-cell defect (Conley, M. E., supra, at 226–227). XSCID carrier females are immunologically normal. They exhibit non-random X chromosome inactivation in T-cells (i.e., they inactivate the mutant X chromosome) (Puck, J. M., et al. *J. Clin. Invest.* 79: 1395–1400 (1987); Conley, M. E., et al. *J. Clin. Invest.* 85: 1548–1554 (1990)). While random X chromosome inactivation is observed in B-cell hybrids derived from less mature surface IgM positive B-cells, non-random X chromosome inactivation is seen in surface IgM negative B-cells which have undergone further replication and differentiation (Conley, M. E., et al. *Proc. Natl. Sci. USA* 85: 3090–3094 (1988)). These results are consistent with the XSCID gene product playing a role during terminal B-cell differentiation.

Linkage studies have localized the defective gene for XSCID to Xq11–13 (Goodship, J., et al. *Clin. Exp. Immunol.* 83: 4–9 (1991)). The gene defect, however, has not been cloned and therefore the gene product is unknown (Goodship, J., et al., supra, at 4).

Presently, diagnosis of XSCID is based on linkage analysis and X chromosome inactivation studies (Conley, M. E., supra, at 216–224). These methods are only suited for families with prior history of immunodeficiency. Conley, M. E., Supra provides a detailed explanation of linkage analysis and X chromosome inactivation and the problems associated with these methods (Conley, M. E., supra, at 216–224).

Current treatment of XSCID involves transplantation of histocompatible bone marrow precursors from healthy siblings or by transplants of haplotype-mismatched bone marrow precursors from the healthy parents (Cooper, M. D. and Butler, J. L., supra, at 1037). Patients also may benefit from gammaglobulin therapy and specific antimicrobial treatment. However, the only long-term effective therapy for XSCID is bone marrow transplantation (Conley, M. E., supra, at 226). Bone marrow transplantation, unfortunately, is limited by the availability of compatible donors.

IL-2 and IL-2 receptors critically regulate the magnitude and duration of the T-cell immune response following antigen activation (Leonard, W. J. In *Interleukin*-2. Blackwell Scientific Publications, Ltd., Osney Mead, Oxford, England (J. Waxman and F. Balkwill, editors), pp. 29–46, (1992); Smith, K. A. *Ann. Rev. Cell Biol.* 5: 397–425 (1989); Waldmann, T. A. *Ann. Rev. Biochem.* 58: 875–911 (1989)). Roles for this system also have been suggested in thymic maturation (Raulet, D. H. *Nature* 314: 101–103 (1985); Jenkinson, E. J., et al. *Nature* 329: 160–162 (1987); Ceredig, R., et al. *Nature* 314: 98–100; Tentori, L., et al. *Exp. Med.* 168: 1741–1747 (1988)) and B-cell responses (Smith, K. A. supra; Waldmann, T. A., et al. *J. Exp. Med.* 160: 1450–1466 (1984); Mingari, M. D., et al. *Nature* 312: 641–643 (1984); Loughnan, M. S. & Nossal, G. J. V. *Nature* 340: 76–79 (1989)).

Three chains of the IL-2 receptor have been identified: the $\alpha$, $\beta$, and $\gamma$ chains. IL-2R$\alpha$ is not expressed on resting cells but is strongly induced following T cell activation (Leonard, W. J., et al. *Nature* 311: 625–631 (1984); Nikaido, T., et al. *Nature* 311: 631–635 (1984)). Its gene spans more than 35 kb on chromosome 10 p14–15 (Leonard, W. J., et al. *Science* 230: 633–639 (1985); Leonard, W. J., et al. *Science* 228: 1547–1549 (1985); Ishida, et al. *Nucl. Acids Res.* 13: 7579–7589 (1985)) and is organized in 8 exons and 7 introns. IL-2R$\beta$ is constitutively expressed, but is induced 5–10 fold following T-cell activation (Loughnan, M. S. & Nossal, G. J. V., supra). Its gene spans 24 kb on chromosome 22q11.2–12 and is organized in 10 exons and 9 introns (Gnarra, J. R., et al. *Proc Natl. Acad. Sci USA* 87: 3440–3444 (1990); Shibuya, H., et al. *Nucl. Acids. Res.* 18: 3697–3703 (1990)). IL-2R$\gamma$ is constitutively expressed. Its gene spans 4.2 kb and is composed of 8 exons and 7 introns (Noguchi, M., et al, submitted).

Different combinations of the IL-2 receptor $\alpha$, $\beta$, and $\gamma$ chains (Takeshita, T., et al. *Science* 257: 379–382 (1992); Leonard, W. J., et al. *Nature* 311: 625–631 (1984); Nikaido, T., et al. *Nature* 311: 631–635 (1984); Sharon, M., et al. *Science* 234: 859–863 (1986); Tsudo, M., et al. *Proc. Natl. Acad. Sci USA* 83: 9694–9698 (1986); Teshigawara, K., et al. *J. Exp. Med.* 165: 223–238 (1987); Dukovich, M., et al. *Nature* 327: 518–522 (1987); Sharon, M. et al. *J. Exp. Med.* 167: 1265–1270 (1988); Siegel, J. P., et al. *Science* 238: 75–78 (1987); Hatakeyama, M. et al. *Science* 244: 551–556 (1989); Takeshita, T., et al. *Intl. Immunol.* 2: 477–480 (1990); Takeshita, T., et al. *J. Immunol.* 148: 2154–2158 (1992); Voss, S. D., et al. *J. Exp. Med.* 176: 531–541 (1992); Arima, N. *J. Exp. Med.* 176: 1265–1272 (1992)) result in the formation of three different classes of IL-2 receptors. Low affinity receptors contain IL-2R$\alpha$, but not IL-2R$\beta$ and IL-2Rγ chains; intermediate affinity receptors contain IL-2Rβ and IL-2Rγ chains, but not IL-2Rα; and high affinity receptors contain all three chains. The high and intermediate affinity receptors are important for IL-2 signaling by transducing IL-2 signals.

Although other forms of SCID has been associated with defective IL-2 production (Pahwa, R., et al. *Proc. Natl. Sci. USA* 86: 5069–5073 (1989); Weinberg, K. and Parkman, R. *N. Eng. J. Med.* 322(24): 1718–1723 (1990)), there is no teaching or suggestion in the art that XSCID or any other forms of SCID are associated with a mutation of the IL-2Rγ gene product.

In one patient, the defective IL-2 production resulted from defective production of NF-AT, a nuclear factor required for IL-2 gene transcription (Pahwa, R., et al., supra; Chatila, T., et al. *Proc. Natl. Acad. Sci. USA* 87: 10033–10037 (1990)). The patient's cells were capable of producing at least some IL-2 mRNA (Chatila, T., et al., supra), consistent with the possibility that the amount of IL-2 produced was sufficient for a degree of thymic maturation but not sufficient for normal mature T-cell immune function in the periphery.

Weinberg and Parkman described a phenotypically similar patient. In that case, however, no IL-2 mRNA was detectable in peripheral blood T cells activated with nitogens (Weinberg, K. and Parkman, R., supra). Although peripheral T cells were present, some circulating cells appeared to be thymocytes, consistent with a thymic maturation defect. The basis for the lack of IL-2 mRNA production in this patient is unknown, particularly since genomic Southern blot analysis revealed that the IL-2 gene was grossly intact.

The present invention is based upon the discovery that patients with XSCID possess a mutated IL-2Rγ gene. This discovery has both diagnostic and therapeutic applications.

SUMMARY OF THE INVENTION

The present invention provides a method for diagnosing XSCID in a male subject or determining whether a female subject is a carrier of XSCID which comprises determining whether the male or female subject possesses a mutated IL-2Rγ gene, the presence of the mutated IL-2Rγ gene being indicative that the male subject has XSCID or the female subject is a carrier of XSCID.

The present invention also provides a method for diagnosing XSCID in a subject which comprises determining whether the subject possesses a truncated IL-2Rγ protein, the presence of the truncated IL-2Rγ protein being indicative of XSCID.

The present invention also provides a kit for diagnosing XSCID in a male subject or determining whether a female subject is a carrier of XSCID which comprises IL-2Rγ primers capable of amplifying a portion of genomic DNA, or a portion of cDNA synthesized by reverse transcription of mRNA from the subject; and a standard nucleotide base sequence for normal IL-2Rγ for determining at least one difference in nucleotide base sequence of corresponding regions of the subject's DNA, whereby a difference in the base sequence of the subject's DNA as compared with the standard sequence indicates that the male subject has XSCID or the female subject is a carrier of XSCID.

The present invention further provides a kit for diagnosing XSCID in a male subject or determining whether a female subject is a carrier of XSCID which comprises a labeled IL-2Rγ probe from a normal IL-2Rγ gene capable of hydridizing a portion of genomic DNA, or a portion of cDNA synthesized by reverse transcription of mRNA from the subject; and a standard nucleotide base sequence for normal IL-2Rγ for determining at least one difference in nucleotide base sequence of corresponding regions of the subject's DNA, whereby a difference in the base sequence of the DNA from the sample as compared with the standard sequence indicates that the male subject has XSCID or the female subject is a carrier of XSCID.

The present invention still further provides a method for treating XSCID in a patient in need of such treatment which comprises removing cells from the patient, delivering a normal IL-2Rγ gene or IL-2Rγ cDNA into the cells so removed, and administering a therapeutically effective amount of the cells containing the normal IL-2Rγ gene or the IL-2Rγ cDNA to the patient so that the cells express the protein encoded by the normal IL-2Rγ gene, thereby treating XSCID in the patient.

Also provided by the present invention is a method for treating XSCID in a patient with a mutation in the IL-2Rγ gene which comprises removing cells from the patient, replacing the mutation in the IL-2Rγ gene contained within the cells with normal nucleic acid by homologous recombination, and administering a therapeutically effective amount of the cells to the patient so that the cells express the protein encoded by the normal IL-2Rγ gene, thereby treating XSCID.

Moreover, the present invention provides a method for monitoring therapy in a patient receiving treatment for XSCID which comprises monitoring the level of normal IL-2Rγ mRNA at various stages of treatment according to the method above, an increase in the level of mRNA being indicative of therapeutic efficacy.

Lastly, the present invention provides a promoter which regulates expression of IL-2Rγ, a vector comprising a DNA molecule operably linked to the promoter, a prokaryotic or eukaryotic cell host stably transformed or transfected with the vector, a transgenic animal comprising a gene regulated by the promoter, and a transgenic animal comprising a mutated IL-2Rγ.

BRIEF DESCRIPTION OF THE FIGURES

FIG. 2(a). Mendelian inheritance of the IL-2Rγ gene in three-generation CEPH family 1331. The pedigree of the family is shown (squares, males; circles, females) above the lanes and the alleles in each lane are indicated below the lanes. SSCP analysis of this family was performed as described in the Experimental Details section using PCR primers corresponding to intron 2. Bands 1 and 3 were present in all DNAs in this family. Bands 2 and 4 represent allele 1 and band 5 represents allele 2. In genotypes, the designation "0" indicates hemizygosity, as inferred from the male sex and X chromosomal location of the gene.

FIG. 2(b). Multipoint linkage analysis of IL-2Rγ with other loci spanning Xcen-q22. The five loci (upper part of panel) were ordered using the CILINK program and all possible orders were considered. The most likely recombination fractions between loci and the odds against reversing the order of adjacent loci (parentheses) are shown. Although DXS3 is telomeric of DXYS1, in the linkage analysis the odds (9.4×) for ordering DXYS1 and DXS3 are not significant, and the odds against reversing DXS132 and IL-2Rγ are only $7.7×10^2$; the odds against all other orders exceeds $3×10^3$. Lower part of panel: Two more loci (DXS159 and PGK1) were then added to this cluster, and the order and most likely recombination fractions were determined by sequential use of the programs CMAP and CILINK considering all 8 possible orders; all other orders were excluded by CMAP with odds >1000: 1. The three pairs of loci within parentheses could not be ordered with odds of even $10^2$. The most likely recombination fractions between adjacent loci are shown including those between loci in parentheses. The total interval spanned is approximately 15 centimorgans.

FIG. 2(c). Recombinants between the IL-2Rγ gene and other loci within the region Xcen-q13. Only meioses which are informative for at least two loci in addition to IL-2Rγ are shown. Circles indicate informative loci which are recombinant with IL-2Rγ in a meiosis and these circles are joined by solid lines. Squares indicate loci which are nonrecombinant with IL-2Rγ in a meiosis and these points are joined by dashed lines. Hatched lines join adjacent circles to squares, and indicate the regions containing a recombination breakpoint in each meiosis. The absence of circles or squares at loci indicates maternal homozygosity at those loci. The gene must be telomeric to DXS132 based upon individuals 134013, 134106, 134707, and 1329207. Recombinants of DXYS1 and/or DXS3 in individuals 133106, 134703, 134707, and 140806 indicate that the gene must be centromeric to these loci. Thus, the shaded area between DSX132 and DXYS1 indicates the region containing the IL-2Rγ gene. Double recombinants in proximal Xq were found in individuals 1708 and 133108.

FIG. 3(a). Pedigrees and histories of the XSCID patients studied. The pedigree for each patient is shown (squares, males; circles, females; black squares, males with XSCID; slashes, deceased; small squares and diamonds indicate miscarriages).

FIG. 3(b). Sequencing of XSCID IL-2Rγ gene DNA. Shown is the nucleotide sequence from a normal donor (left panel in each pair) and DNA from patients 1, 2 and 3 (right panel in each pair). Patient 1 has an AAA (lys) to TAA (stop codon) transversion in exon 3, resulting in truncation of the C-terminal 251 amino acids; patient 2 has a CGA (arg) to TGA (stop codon) transition in exon 7, resulting in the truncation of 81 amino acids; and patient 3 has a TCG (ser) to TAG (stop codon) transversion in exon 7, resulting in the truncation of 62 amino acids. The location of each mutation is indicated in the sequence to the right of each set of panels. The sequence shown is complementary to the coding strand. The boxed residues are complementary to TAA, TGA, and TAG stop codons, respectively.

FIG. 3(c). Schematic showing locations of the artificial stop codons (heavy arrows) present in the XSCID patients. Patient 1 has a premature stop codon in exon 3 and patients 2 and 3 have premature stop codons in exon 7.

FIG. 4(a) At the top is a schematic representation of the cDNA, divided according to exon boundaries. Below the cDNA is a scale representation of the exons and introns. Positions of restriction enzyme recognition sites are indicated. All exons are contained on two contiguous EcoRI fragments of 7.9 kb and 4 kb. The EcoRI site dividing these fragments corresponds to the EcoRI site contained within the cDNA.

FIG. 4(b). The relationship between exons and functional domains of IL-2Rγ. Locations of the signal sequence, extracellular region, transmembrane domain, and cytoplasmic region are indicated. Numbers denote the nucleotide positions at which the introns interrupt the cDNA. The positions of the four conserved cysteine residues (black-solid arrows) and six potential N-linked glycosylation sites (gray arrows) are indicated. Exons 1 to 6 encode the extracellular domain. Exon 4 encodes the region hypothesized to potentially represent a leucine zipper (Hatakeyama, M., et al. *Science* 244: 551–556 (1989)) and exon 5 encodes the WSXWS motif. Exon 6 encodes the transmembrane domain and exons 7 and 8 encode the cytoplasmic domain.

FIG. 5. DNA sequence of the IL-2Rγ promoter (SEQ ID NO. 1). +1 corresponds to the major initiation site identified by primer extension and ribonuclease protection assays. The three principal transcription initiation sites are underlined (−2, +1, and +5). Also included is the sequence of the entire exon and part of the first intron. The coding region and deduced amino sequence (SEQ ID NO. 2) are in bold. The beginning of the first intron is indicated by an open bracket. The Hind III, Ple I, and Bgl II sites are marked. The arrow indicates the point of digestion by Ple I on the bottom strand, and therefore represents the 3' end of the RNA probe generated in the ribonuclease protection assay.

FIG. 6(a). Schematic of the 641 bp fragment (−606 to +35) generated by PCR.

FIG. 6(b). This promoter fragment (−606 to +35) was subcloned in both orientations in the vector pLucO which contains the luciferase reporter gene. A DNA fragment from the multiple cloning site of pBluescript was inserted in the Hind III site of pLucO and used as a promoterless control.

DETAILED DESCRIPTION OF THE INVENTION

Figure 1:
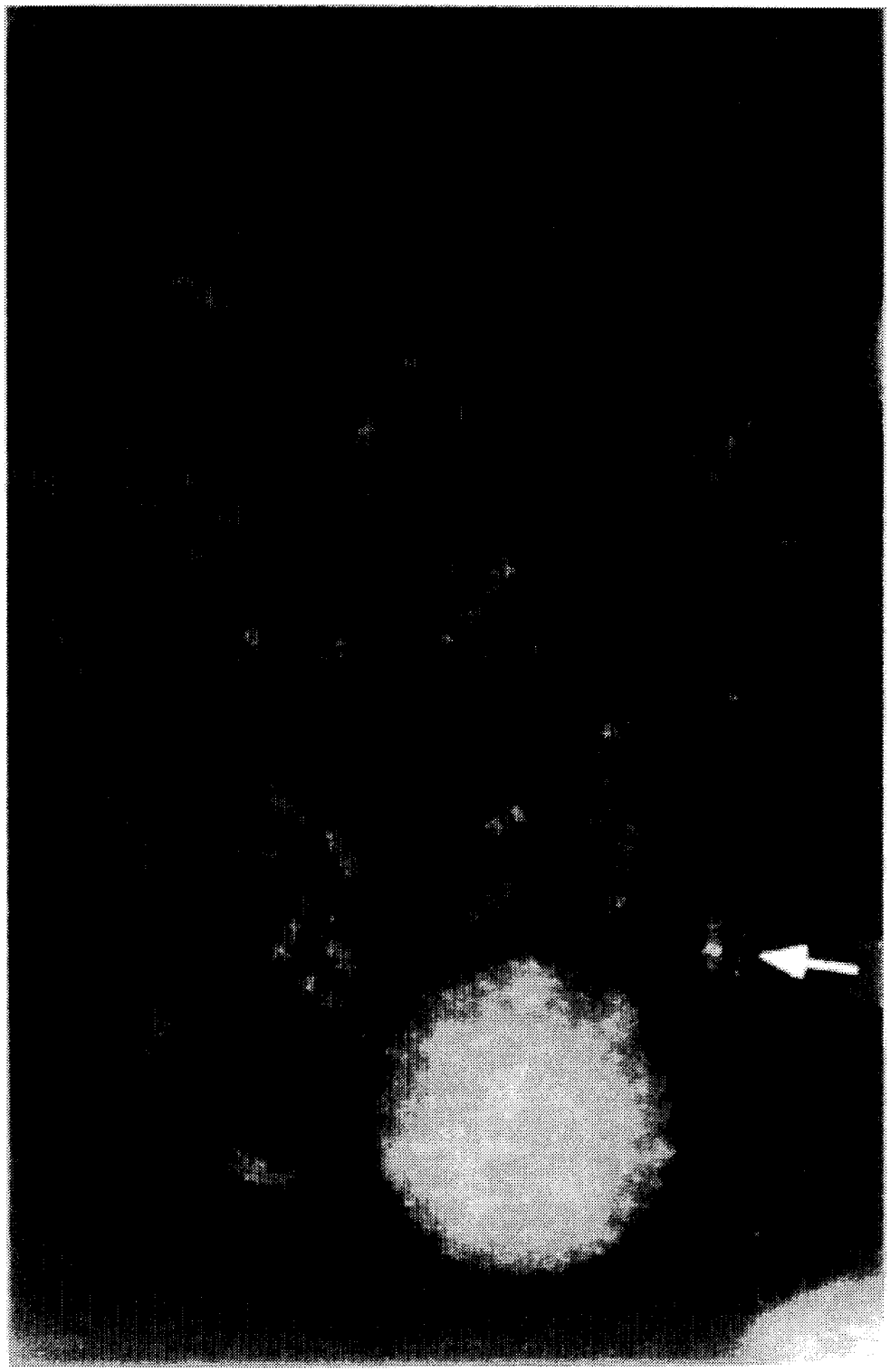
FIG. 1. Localization of IL-2Rγ to Xq13 by in situ hybridization. Arrow indicates hybridization of IL-2Rγ probe at one or both chromatids at Xq13.

The present invention provides a method for diagnosing XSCID in a male subject or determining whether a female subject is a carrier of XSCID which comprises determining whether the male or female subject possesses a mutated IL-2Rγ gene, the presence of the mutated IL-2Rγ gene being indicative that the male subject has XSCID or the female subject is a carrier of XSCID.

The method of the present invention may be used for diagnosing XSCID in embryos, fetuses, or newborn males, or determining whether females considering having children are carriers of XSCID. Preferably, candidates for the diagnostic test include females with family relatives who have or had the disease to determine if these females are carriers, and prenatal or newborn males whose mothers have been diagnosed or might be suspected to be carriers.

The normal IL-2Rγ gene spans approximately 4.2 kb and is organized in 8 exons and 7 introns. The term "IL-2Rγ gene" as used herein thus includes the coding regions (translated regions), the non-coding regions (promoter, enhancer, 5' and 3' untranslated regions), as well as the exon/intron splice junctions. The mutation may occur in any of the coding regions, the non-coding regions, or in the exon/intron splice junctions. In the preferred embodiment, the mutation is in one of the coding regions. The mutation may be a point mutation, a frame-shift mutation, a deletion, an insertion, or a rearrangement. Preferably, the mutation is one or more point mutations, and specifically a nonsense mutation. A nonsense mutation changes a codon that normally codes for a particular amino acid into a premature stop codon.

Whether the subject possesses the mutated IL-2Rγ gene may be determined by various procedures known in the art or procedures that are not yet discovered or practical. The particular procedure will depend upon whether the mutation is known (i. e. the location and type of mutation was previously determined from a relative or immediate family member of a subject who has or had XSCID or is a carrier of XSCID), whether the mutation is unknown, as well as the type of mutation. The subject invention is therefore not limited to the procedures discussed below.

In the methods of the present invention, the biological fluid or tissue samples which contain nucleic acid or protein may be removed by procedures known to those skilled in the art and are not limited to the following procedures.

In the earlier stages of pregnancy (i. e., the ninth through eleventh weeks) chorionic villus sampling, or CVS may be employed. Chorionic villi are fingerlike projections of the membrane surrounding the embryo which contain the same nucleic acid as the developing fetus. The chorionic villi may be removed by insertion of a catheter through the vagina into the uterus and using suction to remove a small sample of villi. Alternatively, the villa may be collected using a needle through the mother's abdominal wall.

Amniocentesis of amniotic fluid or blood sampling may be performed after the fourteen week of pregnancy, and usually between weeks eighteen and twenty-one. Amniocentesis involves insertion of needle through the mother's abdominal wall. Fetal blood sampling involves inserting a needle through the mother's abdomen directly into the large blood vessels in the umbilical cord.

For newborns or adult subjects, blood is drawn by known procedures.

The cells may then be grown in culture or subjected to nucleic acid extraction directly depending upon the level of cells required. For example, the cells from amniotic fluid generally have to be grown in culture for 1 to 3 weeks to have sufficient numbers of cells for nucleic acid extraction. The villa usually contain enough cells to permit the nucleic acid to be extracted directly. The nucleic acid from one cell is sufficient for PCR amplification (Zhang, et al. *Proc. Natl. Acad. Sci.* 89: 5847–5851 (1992)).

The nucleic acid (e. g. genomic DNA or mRNA) is extracted from the cells by known procedures. Specifically, the cells are lysed using an enzyme such as proteinase K, in the presence of detergents such as sodium dodecyl sulfate (SDS), NP40, or Tween 20. If the nucleic acid is genomic DNA, it is then extracted using known techniques such as phenol/chloroform extraction, or other procedures (see U.S. Pat. Nos. 4,900,677 and 5,047,345). Alternatively, the DNA may be isolated using one of the commercially available kits such as the Oncor Genomic DNA isolation kit. RNA is extracted using various known procedures such as guanidinium thiocyanate followed by centrifugation in cesium chloride (Sambrook, J., Fritsch, E. F., and Maniatis, T. "Molecular Cloning, A Laboratory Manual," second edition, Cold Spring Harbor Laboratory Press, pp. 7.0–7.25 (1989)).

In one embodiment, determining whether the subject possesses a mutated IL-2Rγ gene comprises sequencing nucleic acid from the subject and comparing the sequenced nucleic acid with the sequence of a normal IL-2Rγ gene, any difference in sequences being indicative of the mutated IL-2Rγ gene.

The nucleic acid from the subject may be sequenced by known procedures such as the Sanger method of dideoxy-mediated chain termination or the Maxam-Gilbert chemical degradation of DNA method (Sambrook, J., Fritsch, E. F., and Maniatis, T. "Molecular Cloning, A Laboratory Manual," second edition, Cold Spring Harbor Laboratory Press, pp. 13.1–13.104 (1989)), or other procedures known to those skilled in the art. Any difference in sequences other than normal polymorphisms indicates that the subject has a mutated IL-2Rγ gene.

It is within the confines of the present invention that if the nucleic acid is DNA, it may be amplified by PCR prior to sequencing as described below. If the nucleic acid is mRNA, it may be converted into cDNA using reverse transcriptase and then amplified using polymerase chain reaction (RT-PCR) prior to sequencing.

It also is within the confines of the present invention that the nucleic acid from the subject may be hybridized with a probe from a normal IL-2Rγ gene prior to sequencing. Hybridization may be performed essentially as described below.

In another embodiment, PCR amplification may be used to determine whether the subject possesses a mutated IL-2Rγ gene.

In this regard, the method comprises contacting genomic DNA from the subject or cDNA synthesized by reverse transcription of mRNA from the subject with IL-2Rγ primers from a normal IL-2Rγ gene, wherein the primers are capable of amplifying a portion of the genomic DNA or cDNA, detecting no amplification of genomic DNA or cDNA, thereby determining that the subject possesses the mutated IL-2Rγ gene.

Polymerase chain reaction is performed by methods and conditions disclosed in U.S. Pat. Nos. 4,683,202 and 4,683,195 and in Perkin Elmer Cetus PCR kit protocols. The DNA polymerase, deoxyribonucleotide triphosphates (dNTPS) (e.g. dATP, dCTP, dTTP, and dGTP), and amplification buffer (e.g. glycerol, tris-hydrochloric acid, potassium chloride, Tween 20, and magnesium chloride) are readily commercially available (Perkin Elmer Cetus). The polymerase chain reaction may be performed as many cycles as desired.

Reverse transcription (RT) of mRNA and RT-PCR are performed by methods described in commercially available kits such as the RT and RT-PCR kits (Perkin Elmer Cetus).

The IL-2Rγ sense and antisense primers for use in PCR may be selected from the primers listed below or others synthesized from the IL-2Rγ gene. The primers may be produced using a commercially available oligonucleotide synthesizer such as Applied Biosystems Model 392 DNA/RNA synthesizer.

Either the sense or antisense primer may be labeled with a detectable marker by known procedures such as phosphorylation with bacteriophage T4 polynucleotide kinase (Sambrook, J., Fritsch, E. F., and Maniatis, T. "Molecular Cloning, A Laboratory Manual," second edition, Cold Spring Harbor Laboratory Press, pp. 11.31–11.32 (1989)). Suitable markers include but are not limited to fluorescence, enzyme or radiolabeled markers such as $^{32}p$ and biotin.

The nucleic acid from the subject also may be digested with one or more restriction enzymes and separated according to size by electrophoresis prior to PCR or RT-PCR. The digestion and separation by electrophoresis are accomplished by methods well known to those skilled in the art (Sambrook, J., Fritsch, E. F., and Maniatis, T. "Molecular Cloning, A Laboratory Manual," second edition, Cold Spring Harbor Laboratory Press, pp. 6.3–6.6, 7.30–7.36 (1989)).

PCR also may be employed if the subject has a relative who has or had XSCID, or the relative is a carrier of XSCID, and the specific mutation in the IL-2Rγ gene has already been determined.

The method comprises contacting genomic DNA from the subject or cDNA synthesized by reverse transcription of mRNA from the subject with IL-2Rγ primers, wherein at least one of the primers contains an IL-2Rγ mutation from a family relative of the subject who has or had XSCID, or who is a carrier of XSCID, and wherein the primers are capable of amplifying a portion of the genomic DNA or cDNA, detecting amplification of genomic DNA or cDNA, thereby determining that the subject possesses the mutated IL-2Rγ gene.

In another embodiment, hybridization procedures may be used to determine whether the subject possesses a mutated IL-2Rγ gene.

In this regard, the method comprises contacting nucleic acid from the subject with a labeled IL-2Rγ probe from a normal IL-2Rγ gene, wherein the probe is capable of hybridizing to the nucleic acid from the subject, detecting no hybridization of the IL-2Rγ probe to the nucleic acid, thereby determining that the subject possesses the mutated IL-2Rγ gene.

In the method above, if the nucleic acid is DNA or cDNA, it is contacted with a labeled IL-2Rγ probe complementary to the nucleic acid utilizing standard hybridizing conditions and procedures known in the art (Southern, E. M. *J. Mol. Biol.* 98:503 (1975); Sambrook, J., Fritsch, E. F., and Maniatis, T. "Molecular Cloning, A Laboratory Manual," second edition, Cold Spring Harbor Laboratory Press, pp. 9.31–9.62 (1989)).

If the nucleic acid is mRNA, it is contacted with a labeled IL-2Rγ probe complementary to the RNA under standard hybridizing conditions using known procedures (Chirgwin, J. M., et al. *Biochemistry* 18: 5294–5299 (1979); Sambrook, J., Fritsch, E. F., and Maniatis, T. "Molecular Cloning, A Laboratory Manual," second edition, Cold Spring Harbor Laboratory Press, pp. 7.30–7.87 (1989)).

The IL-2Rγ probe may be DNA, cDNA, or RNA depending upon the nucleic acid extracted and the method of hybridization chosen. The IL-2Rγ probe may be the full length sequence of IL-2Rγ including all coding and non-coding regions, a sequence including only the coding or non-coding regions, or any fragment(s) thereof. Preferably, the probe is IL-2Rγ cDNA. The probe may be synthesized using an oligonucleotide synthesizer such as Applied Biosystems Model 392 DNA/RNA synthesizer.

The probe is labeled with a detectable marker by known procedures such as phosphorylation with bacteriophage T4 polynucleotide kinase (Sambrook, J., Fritsch, E. F., and Maniatis, T. "Molecular Cloning, A Laboratory Manual," second edition, Cold Spring Harbor Laboratory Press, pp. 11.31–11.32 (1989)). Suitable markers include but are not limited to fluorescence, enzyme or radiolabeled markers such as $^{32}P$ and biotin. In the preferred embodiment, the marker is $^{32}P$. Hybridization is detected by known techniques.

The nucleic acid from the subject may be digested with one or more restriction enzymes and separated according to size by electrophoresis prior to contact with the probe. The digestion and separation by electrophoresis are accomplished by methods well known to those skilled in the art (Sambrook, J., Fritsch, E. F., and Maniatis, T "Molecular Cloning, A Laboratory Manual," second edition, Cold Spring Harbor Laboratory Press, pp. 6.3–6.6, 7.30–7.36 (1989)).

The nucleic acid also may be amplified using PCR or RT-PCR by the procedures above prior to contact with the probe.

Like PCR, hybridization also may be employed if the subject has a relative who has or had XSCID, or the relative is a carrier of XSCID, and the specific mutation in the IL-2Rγ gene has already been determined.

The method comprises contacting nucleic acid from the subject with a labeled IL-2Rγ probe which contains an IL-2Rγ mutation from a family relative of the subject who has or had XSCID, or who is a carrier of XSCID, wherein the probe is capable of hybridizing to the nucleic acid from the subject, detecting hybridization of the IL-2Rγ probe to the nucleic acid, thereby determining that the subject possesses the mutated IL-2Rγ gene.

In another embodiment, determining whether the subject possesses a mutated IL-2Rγ gene comprises measuring the level of IL-2Rγ mRNA from the subject and comparing the level of IL-2Rγ mRNA so measured with the level of IL-2Rγ mRNA expressed by a normal IL-2Rγ gene, the presence of a lower level of IL-2Rγ mRNA or an absence of mRNA expression from the subject being indicative of the mutated IL-2Rγ gene.

The level of IL-2Rγ mRNA may be determined by methods known to those skilled in the art such as Northern blotting, dot and slot hybridization, S1 nuclease assay, or ribonuclease protection assays by procedures well known in the art (Sambrook, J., Fritsch, E. F., and Maniatis, T. "Molecular Cloning, A Laboratory Manual," second edition, Cold Spring Harbor Laboratory Press, pp. 7.37–7.87 (1989)).

In Northern blotting, the RNA is separated according to size by electrophoresis by known techniques (Chirgwin, J. M., et al. *Biochemistry* 18: 5294 (1979)), and transferred to an activated cellulose, nitrocellulose, or glass or nylon membrane. The IL-2Rγ mRNA is then hybridized with a radiolabeled IL-2Rγ DNA or IL-2Rγ RNA probe followed by audioradiography. The probe may be the full length IL-2Rγ or fragment thereof. Preferably, the probe is the full length IL-2Rγ cDNA. The level of IL-2Rγ mRNA from the subject can then be compared to normal IL 2Rγ mRNA by using the normal IL-2Rγ mRNA as a marker. If the level of IL-2Rγ mRNA is lower than normal IL-2Rγ mRNA expression or nonexistent, then the subject has a mutated IL-2Rγ gene.

In dot and slot hybridization, the RNA is hybridized to an excess of a radiolabeled IL-2Rγ DNA or RNA probe (Kafatos, et al. *Nuc. Acids. Res.* 7: 1541 (1979); Thomas, P. S. *Proc. Natl. Acad. Sci.* 77: 5201 (1980); White, B. A. and F. C. Bancroft *J. Bio. Chem.* 257: 8569 (1982)). The amount of the IL-2Rγ mRNA can then be determined by densitometric tracing of the audioradiograph and compared to the amount of normal IL-2Rγ mRNA.

In S1 nuclease assay or ribonuclease protection assay, the RNA is hybridized with labeled DNA or RNA probes derived from genomic DNA (Berk, A. J. and P. A. Sharp *Cell* 12: 721 (1977); Casey, J. and N. Davidson *Nuc. Acids Res.* 4:1539 (1977)). The products of the hybridization are then digested with nuclease S1 or RNAase under conditions favoring digestion of single stranded nucleic acids. The size of IL-2Rγ mRNA fragments can then be measured by electrophoresis and compared to the size of normal IL-2Rγ mRNA fragments.

In another embodiment, whether the subject possesses a mutated IL-2Rγ gene may be determined using single stranded conformation polymorphism (SSCP) analyses as known in the art (Orita, M., et al. *Proc. Natl. Sci. USA* 86: 2766–2770 (1989)) and PCR. The primers for SSCP are provided below. However, the present invention is not limited to those primers listed. Other primers may be employed.

The present invention also provides a method for diagnosing XSCID in a subject which comprises determining whether the subject possesses a truncated IL-2Rγ protein, the presence of the truncated IL-2Rγ protein being indicative of XSCID.

The term "IL-2Rγ protein" as used herein refers to the protein which is encoded by the IL-2Rγ chain. The IL-2Rγ protein comprises a sequence of 369 amino acids in the open reading frame and 347 amino acids in the mature protein. The amino acid sequence is provided in Takeshita, et al. *Science* 257: 379–382 (1992). The term "truncated" refers to the absence of a portion of the protein that is normally present in IL-2Rγ protein. The truncation may occur throughout the protein and ranges from about a few to several hundred amino acids.

In the method above, the determining comprises isolating the IL-2Rγ protein from the subject, determining the molecular weight of the isolated IL-2Rγ protein, and comparing the molecular weight of the isolated IL-2Rγ protein to the molecular weight of a normal IL-2Rγ protein, a substantially lower molecular weight for the isolated IL-2Rγ protein is indicative that the protein is truncated.

The IL-2Rγ protein may be isolated by various procedures known in the art including immunoprecipitation, solid phase radioimmunoassay (RIA) (e.g. competition RIAs, immobilized antigen or antibody RIAs, or double antibody RIAs), enzyme-linked immunosorbent assay (ELISA), or Western blotting.

The assays above utilize one or more antibodies which are immunoreactive with the IL-2Rγ protein. The antibodies may be polyclonal or monoclonal and are produced by standard techniques. The polyclonal antibody may be produced by immunizing a rabbit, mouse, rat, hamster, or goat with the IL-2Rγ protein or fragment thereof as an immunogen and collecting the serum produced thereby. The protein or fragment thereof may be coupled to a protein such as keyhole limpet hemocyanin (KLH) or bovine serum albumin (BSA), with or without adjuvant. A booster injection should be given 2–6 weeks after the primary injection. Additional booster injections may be given at later periods if necessary. To produce monoclonal antibodies, the spleen cells from the mouse, rat, or hamster are removed and fused with a myeloma cell, grown in culture, or in an animal to produce the desired monoclonal antibody by standard procedures. The antibodies or the protein may be labeled with a detectable marker such as a fluorescence, enzyme or radiolabeled marker.

In the preferred embodiment, the protein is isolated using immunoprecipitation. Specifically, the cells are removed from the subject as described above. The cells are then radiolabeled with a marker such as $^{35}S$ (e.g. $^{35}S$-labeled methionine or $^{35}S$-labeled methionine and cysteine), $^{32}P$, or $^{125}I$ and subsequently lysed using standard techniques (Sambrook, J., Fritsch, E. F., and Maniatis, T. "Molecular Cloning, A Laboratory Manual," second edition, Cold Spring Harbor Laboratory Press, pp. 18.26–18.41 (1989)). The antibody (monoclonal or polyclonal) produced above is then added to the cell lysates. The protein antibody complexes are then collected by standard techniques.

Detailed experimental procedures for other assays which can be used to isolate the protein such as solid phase radioimmunoassay (RIA) (e.g. competition RIAs, immobilized antigen or antibody RIAs, or double antibody RIAs), enzyme-linked immunosorbent assay (ELISA), or Western blotting may be found in Sambrook, J., Fritsch, E. F., and Maniatis, T. "Molecular Cloning, A Laboratory Manual, " second edition, Cold Spring Harbor Laboratory Press, pp. 18.19–18.75 (1989).

The protein also may be isolated by affinity labeling (also referred to as chemical cross-linking) using $^{125}I$-labeled IL-2 as described in Sharon, et al. *Science* 234: 859–863 (1986); or coprecipitation using anti-IL-2Rβ antibodies as reported by Takeshita, et al. *Intern. Immun.* 2(5): 477–480 (1990); *Science* 257: 379–382 (1992).

The molecular weight of the isolated protein is analyzed by SDS-polyacrylamide gel electrophoresis (Sambrook, J., Fritsch, E. F., and Maniatis, T. "Molecular Cloning, A Laboratory Manual," second edition, Cold Spring Harbor Laboratory Press, pp. 18.47–18.59 (1989)). The molecular weight of the protein is determined using various known markers. This molecular weight is compared to the molecular weight for the normal IL-2Rγ protein which is about 64 KDa. If the molecular weight of the protein is substantially lower, the protein is truncated. "Substantially" is defined as at least about 10 percent lower, and preferably at least about 25 percent lower.

The present invention also provides a kit for diagnosing XSCID in a male subject or determining whether a female subject is a carrier of XSCID which comprises IL-2Rγ primers capable of amplifying a portion of genomic DNA, or a portion of cDNA synthesized by reverse transcription of mRNA from the subject; and a standard nucleotide base sequence for normal IL-2Rγ for determining at least one difference in nucleotide base sequence of corresponding regions of the subject's DNA, whereby a difference in the base sequence of the subject's DNA as compared with the standard sequence indicates that the male subject has XSCID or the female subject is a carrier of XSCID.

The primers above are IL-2Rγ sense and antisense primers and may be selected from the group of primers listed below or other primers synthesized from the IL-2Rγ gene. The primers may be produced using a commercially available oligonucleotide synthesizer such as Applied Biosystems Model 392 DNA/RNA synthesizer.

Either the sense or antisense primer may be labeled with a detectable marker by known procedures such as phosphorylation with bacteriophage T4 polynucleotide kinase (Sambrook, J., Fritsch, E. F., and Maniatis, T. "Molecular Cloning, A Laboratory Manual," second edition, Cold Spring Harbor Laboratory Press, pp. 11.31–11.32 (1989)). Suitable markers include but are not limited to fluorescence, enzyme or radiolabeled markers such as $^{32}P$ and biotin.

The present invention also provides a kit for diagnosing XSCID in a male subject or determining whether a female subject is a carrier of XSCID which comprises a labeled IL-2Rγ probe from a normal IL-2Rγ gene capable of hybridizing a portion of genomic DNA, or a portion of cDNA synthesized by reverse transcription of mRNA from the subject; and a standard nucleotide base sequence for normal IL-2Rγ for determining at least one difference in nucleotide base sequence of corresponding regions of the subject's DNA, whereby a difference in the base sequence of the DNA from the sample as compared with the standard sequence indicates that the male subject has XSCID or the female subject is a carrier of XSCID.

The IL-2Rγ probe may be DNA, cDNA, or RNA. The IL-2Rγ probe may be the full length sequence of IL-2Rγ including all coding and non-coding regions, a sequence including only the coding or non-coding regions, or any fragment(s) thereof. Preferably, the probe is IL-2Rγ cDNA. The probe may be synthesized using an oligonucleotide synthesizer such as Applied Biosystems Model 392 DNA/RNA synthesizer.

The probe is labeled with a detectable marker by known procedures such as phosphorylation with bacteriophage T4 Polynucleotide kinase (Sambrook, J., Fritsch, E. F., and Maniatis, T. "Molecular Cloning, A Laboratory Manual," second edition, Cold Spring Harbor Laboratory Press, pp. 11.31–11.32 (1989)). Suitable markers include but are not limited to fluorescence, enzyme or radiolabeled markers such as $^{32}P$ and biotin. In the preferred embodiment, the marker is $^{32}P$.

The present invention also provides a method for treating XSCID in a patient in need of such treatment which comprises removing cells from the patient, delivering a normal IL-2Rγ gene or IL-2Rγ cDNA into the cells so removed, and administering a therapeutically effective amount of the cells containing the normal IL-2Rγ gene or the IL-2Rγ cDNA to the patient so that the cells express the protein encoded by the normal IL-2Rγ gene, thereby treating XSCID in the patient. This method is generally performed as described (Ell Gilboa, "Retrovirus Vectors and Their Uses in Molecular Biology," *BioEssays* 5: 252–257 (1987)).

The cells removed from the patient are preferably bone marrow cells. These cells are removed from the patient by standard techniques. It is preferred that some of the cells so removed are stem cells and that the normal IL-2Rγ gene or the IL-2Rγ cDNA is delivered into some of these stem cells. As mentioned previously, the normal IL-2Rγ gene contains the promoter (including introns), which specifically regulates the expression of the IL-2Rγ gene. If the normal IL-2Rγ gene is delivered into the cells, it is preferred that this promoter also is delivered. If IL-2Rγ cDNA is delivered into the cells, the expression may be controlled by the IL-2Rγ promoter or by a different promotor.

The normal IL-2Rγ gene or IL-2Rγ cDNA may be delivered by one of the following techniques. The present invention, however, is not limited to the mode of delivery described and may consist of other modes both known and unknown.

In one embodiment, the normal IL-2Rγ DNA or IL-2Rγ cDNA may be delivered into the patient's cells by using a vector. Suitable vectors include retroviruses such as an adenoassociated virus (AAV), a Moloney murine leukemia virus (MoMLV) or DNA viruses such as the Epstein-Barr virus. The normal IL-2Rγ DNA or IL-2Rγ cDNA are introduced into the vector by standard techniques. The vectors may be double expression vectors, vectors with internal promoters, or self-inactivating vectors. The use of other vectors besides those specifically listed is also embodied by the present invention.

In another embodiment, the normal IL-2Rγ DNA may be delivered into the cell using transfection by chemical or physical techniques such as the calcium phosphate-mediated DNA uptake, microinjection, electroporation, or fusion techniques.

The cells containing the normal IL-2Rγ DNA are then administered by injection. The therapeutically effective amount of the cells administered is an amount effective to treat XSCID.

The present invention also provides a method for treating XSCID in a patient with a mutation in the IL-2Rγ gene which comprises removing cells from the patient, replacing the mutation in the IL-2Rγ gene contained within the cells with normal nucleic acid by homologous recombination, and administering a therapeutically effective amount of the cells to the patient so that the cells express the protein encoded by the normal IL-2Rγ gene, thereby treating XSCID.

The method is preformed essentially as described above except that the mutation is replaced with normal nucleic acid by homologous recombination. Homologous recombination is performed by known procedures (Mario R. Capecchi *Science* 244: 1288–1292 (1989)).

The present invention also provides a method for monitoring therapy in a patient receiving treatment for XSCID which comprises monitoring the level of normal IL-2Rγ mRNA at various stages of treatment, an increase in the level of mRNA being indicative of therapeutic efficacy.

Figure 6A:
FIGS. 6(a), and 6(b). Sequences 5' of the IL-2Rγ gene has promoter activity.
Figure 6B:
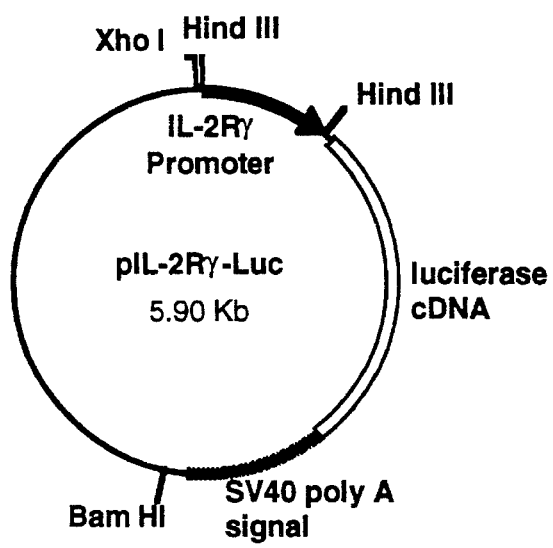
Figure 6C:
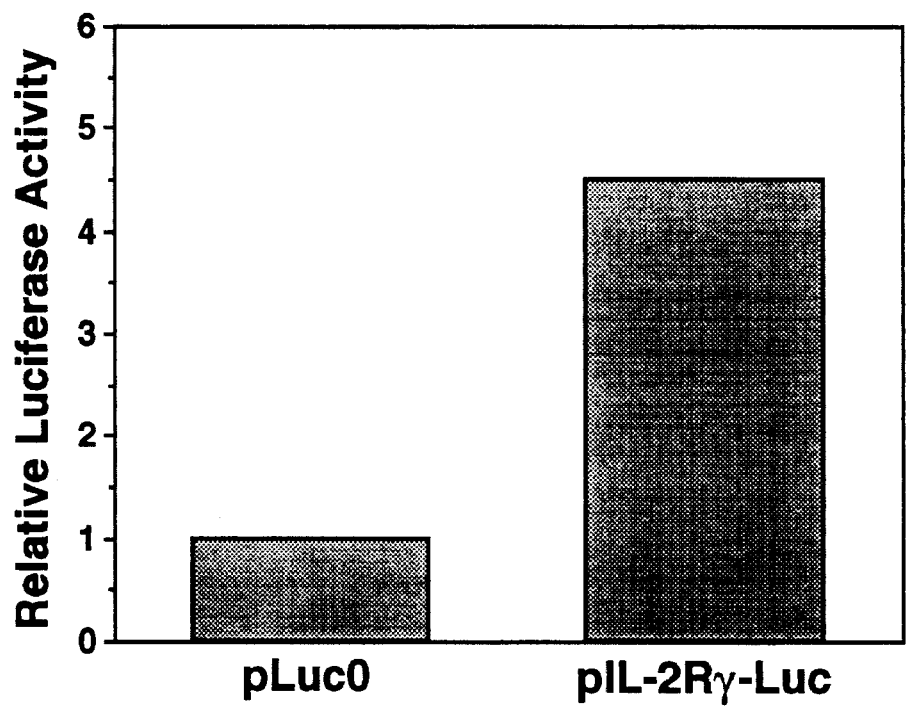
FIG. 6(c). The pIL-2Rγ-luciferase construct resulted in 3910 relative luciferase units (RLU) of activity (lane 2) which is 4.5 fold greater than that seen with the promoterless construct (890 RLU, lane 1). These data presented are the average of two simultaneously performed duplicate experiments. A second set of duplicate experiments yielded similar results.

The present invention further provides a promoter which regulates expression of IL-2Rγ. In the preferred embodiment, the promoter has the nucleotide sequence defined in FIG. 6 and most preferably nucleotides –606 to +35, or regulatory fragments thereof. Regulatory fragments thereof are defined as fragments which regulate expression of IL-2Rγ.

The present invention still further provides a vector comprising a DNA molecule operably linked to the promoter above. The vector may be a plasmid, bacteriophage, or cosmid vector. The promoter and the DNA molecule are inserted into the vector by known techniques (see U.S. Pat. Nos. 4,704,362, 4,366,246, 4,425,437, 4,356,270, and 4,571,421). Preferably, the DNA molecule is the IL-2Rγ gene.

The present invention also provides a prokaryotic or eukaryotic cell host stably transformed or transfected with the vector above. The host cells are stably transformed or transfected by known procedures (see U.S. Pat. Nos. 4,704,362, 4,366,246, 4,425,437, 4,356,270, and 4,571,421).

Lastly, the present invention provides a transgenic animal comprising a gene regulated by the promoter above. The transgenic animal is preferably a mouse. The transgenic animal is prepared by known procedures (Alberts, B., et al. *Molecular Biology of the Cell*, 2d. Garland Publ. Inc., New York and London, pp. 267–269 (1989)). The present invention also provides a transgenic animal comprising a mutated IL-2Rγ gene for use in studying XSCID.

The present invention is described in the following Experimental Details section, which sets forth specific examples to aid in an understanding of the invention, and should not be construed to limit in any way the invention as defined in the claims which follow thereafter.

Experimental Details Section

The IL-2Rγ gene.

Figure 4A:
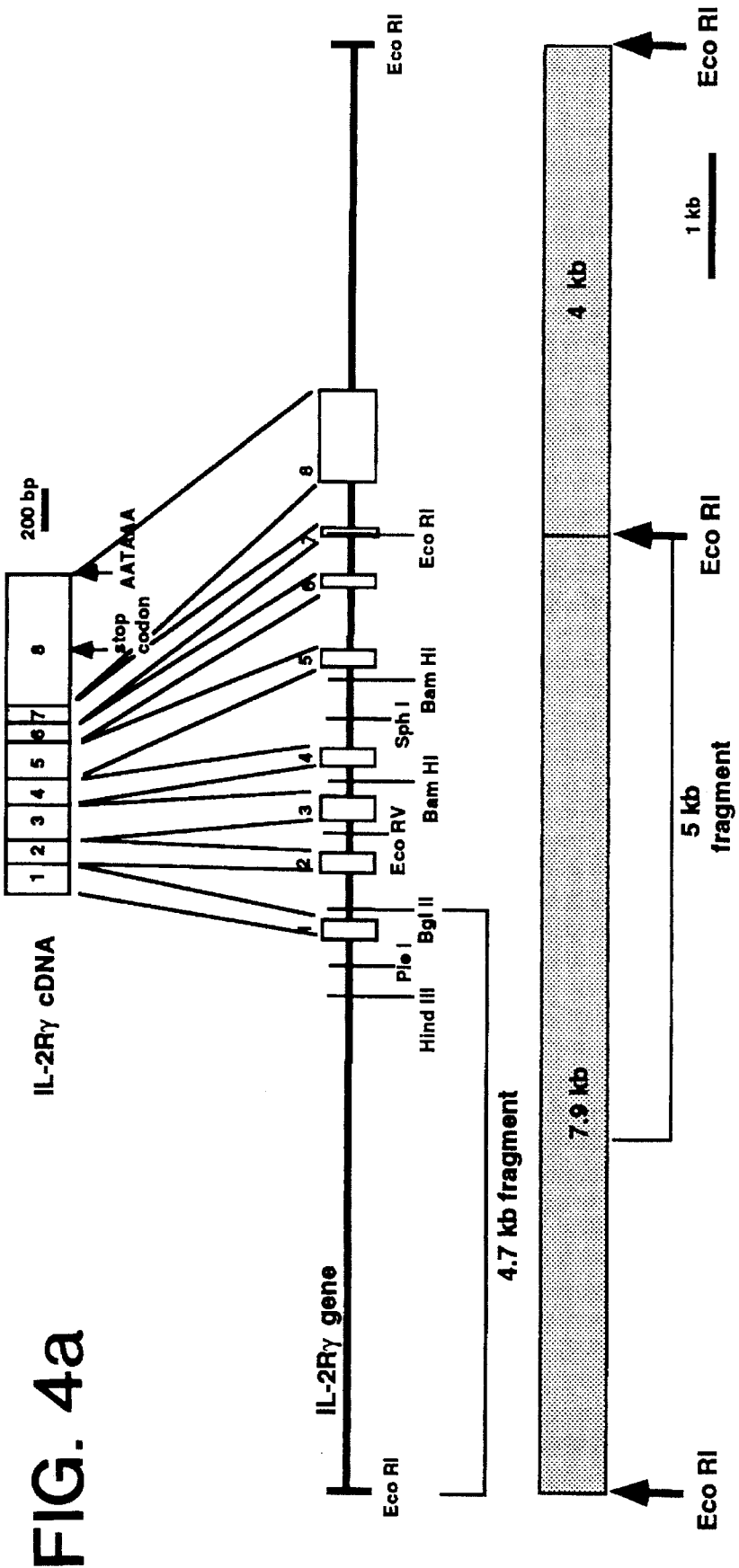
FIGS. 4(a) and 4(b). The organization of the human IL-2Rγ gene.
Figure 4B:
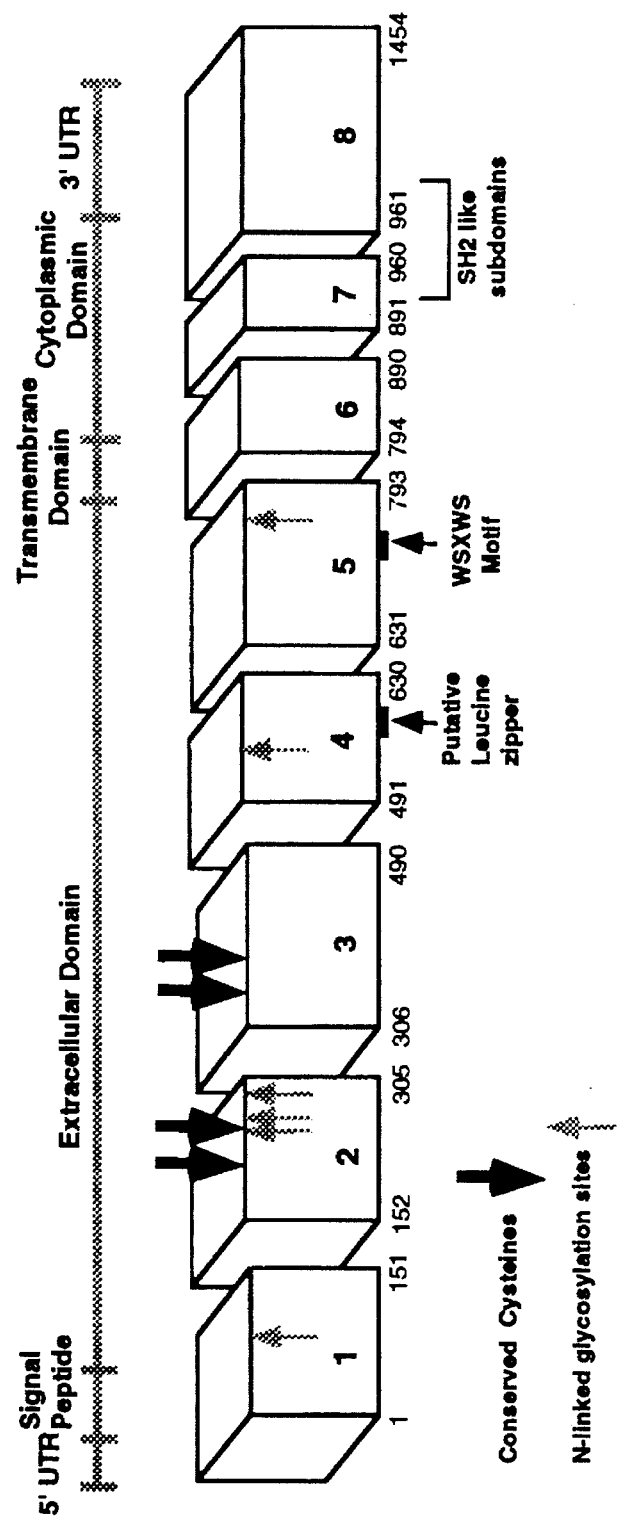

The nucleotide sequence of the IL-2Rγ cDNA has been deposited at DNA Data Bank of Japan and GenBank/European Molecular Biology Laboratory under accession number D11086 (Takeshita, et al. *Science* 257: 379–382 (1992)). The IL-2Rγ cDNA as well as the amino acid sequence encoded by the IL-2Rγ cDNA is also provided in Takeshita, supra. The organization of the IL-2Rγ gene with full map is shown in FIG. 4. The sequence of the promoter region is given in FIG. 5. The promoter sequence as well as the sequences of exons, exon/intron splice junctions, and partial intron sequences are available in GenBank under accession numbers L12176, L12177, L12178, L12179, L12180, L12181, L12182, and L12183. The nucleotide sequence of the IL-2Rγ cDNA which has been deposited at GenBank/European Molecular Biology Laboratory under accession number D11086 is listed herein as SEQ ID NO: 68, as follows:

| | | | | |
|---|---|---|---|---|
| gaagagcaag | cgccatgttg | aagccatcat | taccattcac | 40 |
| atccctctta | ttcctgcagc | tgcccctgct | gggagtgggg | 80 |
| ctgaacacga | caattctgac | gcccaatggg | aatgaagaca | 120 |
| ccacagctga | tttcttcctg | accactatgc | ccactgactc | 160 |
| cctcagtgtt | tccactctgc | ccctcccaga | ggttcagtgt | 200 |
| tttgtgttca | atgtcgagta | catgaattgc | acttggaaca | 240 |
| gcagctctga | gccccagcct | accaacctca | ctctgcatta | 280 |
| ttggtacaag | aactcggata | atgataaagt | ccagaagtgc | 320 |
| agccactatc | tattctctga | agaaatcact | tctggctgtc | 360 |
| agttgcaaaa | aaaggagatc | cacctctacc | aaacatttgt | 400 |
| tgttcagctc | caggacccac | gggaacccag | gagacagagcc | 440 |
| acacagatgc | taaaactgca | gaatctggtg | atccctggg | 480 |
| ctccagagaa | cctaacactt | cacaaactga | gtgaatccca | 520 |
| gctagaactg | aactggaaca | acagattctt | gaaccactgt | 560 |
| ttggagcact | tggtgcagta | ccggactgac | tgggaccaca | 600 |
| gctggactga | acaatcagtg | gattatagac | ataagttctc | 640 |
| cttgcctagt | gtggatgggc | agaaacgcta | cacgtttcgt | 680 |
| gttcggagcc | gctttaaccc | actctgtgga | agtgctcagc | 720 |
| atggagtga | atggagccac | ccaatccact | gggggagcaa | 760 |
| tacttcaaaa | gagaatcctt | tcctgtttgc | attggaagcc | 800 |
| gtggttatct | ctgttggctc | catgggattg | attatcagcc | 840 |
| ttctctgtgt | gtatttctgg | ctggaacgga | cgatgccccg | 880 |
| aattccacc | ctgaagaacc | tagaggatct | tgttactgaa | 920 |
| taccacggga | acttttcggc | ctggagtggt | gtgtctaagg | 960 |
| gactggctga | gagtctcag | ccagactaca | gtgaacgact | 1000 |
| ctgcctcgtc | agtgagattc | ccccaaaagg | aggggcccttt | 1040 |
| ggggagggc | ctggggcctc | cccatgcaac | cagcatagcc | 1080 |
| cctactgggc | cccccatgt | tacaccctaa | agcctgaaac | 1120 |
| ctgaacccca | atcctctgac | agaagaaccc | cagggtcctg | 1160 |
| tagccctaag | tggtactaac | tttccttcat | tcaacccacc | 1200 |
| tgcgtctcat | actcacctca | ccccactgtg | gctgatttgg | 1240 |
| aattttgtgc | cccatgtaa | gcacccccttc | atttggcatt | 1280 |
| ccccacttga | gaattaccct | tttgccccga | acatgttttt | 1320 |
| ctttctccctc | agtctggccc | ttccttttcg | caggattctt | 1360 |
| cctccctccc | tctttccctc | ccttcctctt | tccatctacc | 1400 |
| ctccgattgt | tcctgaaccg | atgagaaata | aagtttctgt | 1440 |
| tgataatcat | c | | | 1451 |
| (SEQ ID NO: 68). | | | | |

The promoter sequence as well as the sequences of exons, exon/intron splice junctions, and partial intron sequences listed in GenBank under accession numbers L12176, L12177, L12178, L12179, L12180, L12181, L12182, and L12183 are listed herein as SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, respectively, as follows:

| | | | | |
|---|---|---|---|---|
| caccaggatt | acagacatga | gccaccgtgc | ttggcctcct | 40 |
| ccttctcacc | atcatttctc | tttccctccc | tgccttcatt | 80 |
| ttctcccccaa | tctagatttc | ttcctgacca | ctatgcccac | 120 |
| tgactccctc | agtgttttca | ctctacccct | cccagaggtt | 160 |
| cagtgttttg | tgttcaatgt | cgagtacatg | aattgcactt | 200 |
| ggaacagcag | ctctgagccc | cagcctacca | acctcactct | 240 |
| gcattattgg | tatgagaagg | gacgaggggg | aggggatgaa | 280 |
| gaagaggtgg | gttggatcag | agaccaagag | agagggtagc | 320 |
| aagtct | | | | 326 |
| (SEQ ID NO: 69); | | | | |
| agagagaggg | tagcaagtct | cccaggtacc | ccactgtttt | 40 |
| ctcctgggga | agtcataagt | cggttgaggg | gagatgaggc | 80 |
| taggctctgg | atatctgcag | tacccagatt | ggccccactg | 120 |
| ttccttcttcc | ttccaaactt | tctcctctag | gtacaagaac | 160 |
| tcggataatg | ataaagtcca | gaagtgcagc | cactatctat | 200 |
| tctctgaaga | aatcacttct | ggctgtcagt | tgcaaaaaaa | 240 |
| ggagatccac | ctctaccaaa | catttgttgt | tcagctccag | 280 |
| gacccacggg | aacccaggag | acagagcc | cagatgctaa | 320 |
| aactgcagaa | tctgggtaat | ttggaaagaa | agggtcaaga | 360 |

| | | | | |
|---|---|---|---|---|
| gaccagggat | actgtgggac | attggagtct | acagagtagt | 400 |
| gttctttat | cataagggta | catgggcaga | aaagaggagg | 440 |
| taggggatca | tgatgggaag | ggaggaggta | ttagggggcac | 480 |
| taccttcagg | atcctgactt | gtcttaggcc | agg | 513 |
| (SEQ ID NO: 70); | | | | |
| aagcttgaag | ctagtattgt | tgttcctcca | tttctagaat | 40 |
| atttttgtat | tataagtcac | acttcctcgc | cagtctcaac | 80 |
| agggaccag | ctcaggcagc | agctaagggt | gggtattctg | 120 |
| gtttggatta | gatcagagga | aagacagctg | tatatgtgcc | 160 |
| cacaggagcc | aagacggtat | tttccatcct | cccaaaacag | 200 |
| gtatgagctt | tgacagagat | ttaagggtga | ccaagtcaag | 240 |
| gaagaggcat | ggcatagaac | ggtgatgtcg | gggtgggg | 280 |
| gttcagaact | tccattatag | aaggtaatga | tttagaggag | 320 |
| aaggtggttg | agaatggtgc | tagtggtagt | gaacagatcc | 360 |
| ttcccaggat | ctaggtgggc | tgaggatttt | tgagtctgtg | 400 |
| acactattgt | atatccagct | ttagtttctg | tttaccacct | 440 |
| tacagcagca | cctaatctcc | tagaggactt | agcccgtgtc | 480 |
| acacagcaca | tatttgccac | accctctgta | aagccctggt | 520 |
| tataaggttc | ttttccaccgg | aagctatgac | agaggaaacg | 560 |
| tgtgggtggg | gagggggtagt | ggggtgaggga | cccaggttcc | 600 |
| tgacacagac | agactacacc | cagggaatga | agagcaagcg | 640 |
| ccatgttgaa | gccatcatta | ccattcacat | ccctcttatt | 680 |
| cctgcagctg | ccccctgctgg | gagtgggggct | gaacacgaca | 720 |
| attctgacgc | ccaatgggaa | tgaagacacc | acagctggtg | 760 |
| ggaaatctgg | gactggaggg | ggctggtgag | aagggtggct | 800 |
| gtgggaaggg | gccgtacaga | gatctggtgc | ctgccactgg | 840 |
| ccattacaat | catgtgggca | gaattgaaaa | gtggagtggg | 880 |
| aagggcaagg | gggagggttc | cctccct | | 907 |
| (SEQ ID NO: 71); | | | | |
| ggaggtatta | ggggcactac | cttcaggatc | ctgacttgtc | 40 |
| taggccaggg | kaatgaccac | atatgcacac | atatctccag | 80 |
| tgatccctg | ggctccagag | aacctaacac | ttcacaaact | 120 |
| gagtgaatcc | cagctagaac | tgaactggaa | caacagattc | 160 |
| ttgaaccact | gtttggagca | cttggtgcag | taccggactg | 200 |
| actgggacca | cagctggact | gtgagtgact | agggacgtga | 240 |
| atgtagcagc | taaggccaag | aaagtagggc | taaaggattc | 280 |
| aaccagacag | atagaaggac | ctaatatcaa | gctcctgttc | 320 |
| tgcntcccag | cttctctgct | caccccctac | cctccctcct | 360 |
| ccaactcctt | nncccccctat | tttctccagt | gagttttctt | 400 |
| tttttctttt | cttttcttttc | ttt | | 423 |
| (SEQ ID NO: 72); | | | | |
| gtagtcaaga | gatgagagag | aaactgggca | gtagcagaga | 40 |
| tgacactggt | gggtgttcag | gagtatgttt | taattctccc | 80 |
| ttctctcata | gacacccact | ttccctcatc | ctctttctcc | 120 |
| tcaaggaaca | atcagtggat | tatagacata | agttctcctt | 160 |
| gcctagtgig | gatgggcaga | aacgctacac | gtttcgtgtt | 200 |
| cggagccgct | ttaacccact | ctgtggaagt | gctcagcatt | 240 |
| ggagtgaatg | gagccaccca | atccactggg | ggagcaatac | 280 |
| ttcaaaaggt | aaaatgggcc | cacatnaccc | aatccatgag | 320 |
| cccaacaccc | cagccttict | aacaccactg | tcttttgctc | 360 |
| cacttccctg | tcactaaagc | ccctaaactt | ggtgccccat | 400 |
| ctctccacac | tgtctaaccc | caacctctag | aaatcaaggt | 440 |
| ttttctgtgt | agggttgggt | tagcgtgttg | ttagagtagg | 480 |
| ggagtggatt | | | | 490 |
| (SEQ ID NO: 73); | | | | |
| ccacatccct | aactcttgga | ttatgttcc | taagatgtaa | 40 |
| gatgaggta | attgttcctg | cctcacagga | gctgtgtga | 80 |
| ggattaaaca | gagngtatgt | ctttagcgcg | gtgcctggca | 120 |
| ccagtgcctg | gcangtagta | ggggcacaac | aaatataagg | 160 |
| tccacttttgc | ttttcttttt | tctatagaga | atcctttect | 200 |
| gtttgcattg | gaagccgtgg | ttatctctgt | tggctccatg | 240 |
| ggattgatta | tcagccttct | ctgtgtgtat | ttctgctgg | 280 |
| aacggtgaga | ttttggaaag | cccagaaaaa | tgagggaac | 320 |
| ggtagctgac | aatagcagag | gaggggttttg | caggggtcttt | 360 |
| aggagtaaag | gatgagacag | taagtaatga | gagattaccc | 400 |
| aagaggggttt | ggtgatggaa | ggaagccaca | ggcacagaga | 440 |
| acacagaa | | | | 448 |
| (SEQ ID NO: 74); | | | | |
| atatggacaa | ctggagaagg | gtgataaaaa | agctttaacc | 40 |
| tatgtgctcc | tgctccctct | ttctccctg | tcaggacgat | 80 |
| gccccgaatt | cccaccctga | agaacctaga | ggatcttgtt | 120 |
| actgaatacc | acgggaactt | ttccggtgaga | acgctgtcat | 160 |
| aagcatgctg | cagtctatca | actgccaact | gcctgccagc | 200 |
| aagacagaca | gagtgt | | | 216 |
| (SEQ ID NO: 75); | | | | |
| gtactccttt | ggacagagct | cggtcttttta | cttcctgccc | 40 |
| ctaattgacc | cctgacctgg | acatatctgt | ctttaggcct | 80 |
| ggagtggtgt | gtctaaggga | ctggctgaga | gtctgcagcc | 120 |
| agactacagt | gaacgactct | gcctcgtcag | tgagattccc | 160 |
| ccaaaaggag | gggcccttgg | ggaggggcct | ggggcctccc | 200 |

|         |            |            |            |     |
|---------|------------|------------|------------|-----|
| catgcaacca | gcatagcccc | tactgggccc | ccccatgtta | 240 |
| caccctaaag | cctgaaacct | gaaccccaat | cctctgacag | 280 |
| aagaacccca | gggtcctgta | g          |            | 301 |

(SEQ ID NO: 76).

Preparation of Probes.

All oligonucleotides were made using an Applied Biosystems Model 392 DNA/RNA synthesizer.

(a) PCR primers for SSCP. Sense and antisense PCR primers were prepared to analyze each intron for SSCPs. Two different pairs of oligonucleotides were used for intron 4. Although the following primers were used for SSCP, the present invention is not limited to the following primers and other primers may be used:

| Intron 1 | Sense     | GAATGAAGACACCACAGCTG | (SEQ ID NO. 3)  |
|          | Antisense | GGGCATAGTGGTCAGGAAG  | (SEQ ID NO. 4)  |
| Intron 2 | Sense     | GATGAAGAAGAGGTGGGTTG | (SEQ ID NO. 5)  |
|          | Antisense | GTTGGAAGGAAGAGGAACAG | (SEQ ID NO. 6)  |
| Intron 3 | Sense     | AGGGATACTGTGGGACATTG | (SEQ ID NO. 7)  |
|          | Antisense | AGTCAGGATCCTGAAGGTAG | (SEQ ID NO. 8)  |
| Intron 4 | Sense     | AGTGACTAGGGACGTGAATG | (SEQ ID NO. 9)  |
|          | Antisense | GTGGGTGTCTATGAGAGAAG | (SEQ ID NO. 10) |
|          | Sense     | GACCTAATATCAAGCTCCTG | (SEQ ID NO. 11) |
|          | Antisense | GTCTATCTGGTATCAGGAAG | (SEQ ID NO. 12) |
| Intron 5 | Sense     | TGTCTTTTGCTCCACTTCCC | (SEQ ID NO. 13) |
|          | Antisense | AGGCAGGAACAATTACCTCC | (SEQ ID NO. 14) |
| Intron 6 | Sense     | AGCTGACAATAGCAGAGGAG | (SEQ ID NO. 15) |
|          | Antisense | TCACCCTTCTCCAGTTGTC  | (SEQ ID NO. 16) |
| Intron 7 | Sense     | GCAGTCTATCAACTGCCAAC | (SEQ ID NO. 17) |
|          | Antisense | GACAGATATGTCCAGGTCAG | (SEQ ID NO. 18) |

(b) Primers for nested PCR amplification of exons and genomic sequencing. The following represent the primers used for nested PCR amplification of exons and genomic sequencing. However, the present invention is not limited to the following primers:

| Exon 1 |  |  |  |
|--------|--|--|--|
| Sense          | AAGGTTCTTTCCACCGGAAG  | (SEQ ID NO. 19) |
| Antisense      | TGATTGTAATTGGCCAGTGGC | (SEQ ID NO. 20) |
| NSense Biotin- | ATGACAGAGGAAACGTGTGG  | (SEQ ID NO. 21) |
| NAntisense     | CAGGCACCAGATCTCTGTAG  | (SEQ ID NO. 22) |
| Seq1           | ACAGCCACCCTTCTCACCAG  | (SEQ ID NO. 23) |
| Seq2           | GCAGCTGCAGGAATAAGAGG  | (SEQ ID NO. 24) |

| Exon 2 |  |  |
|--------|--|--|
| Sense          | ATTACAGACATGAGCCACCG | (SEQ ID NO. 25) |
| Antisense      | CCCTCTCTCTTGGTCTCTG  | (SEQ ID NO. 26) |
| NSense Biotin- | CTCCTTCTCACCATCATTTC | (SEQ ID NO. 27) |
| NAntisense     | CTTGGTCTCTGATCCAACCC | (SEQ ID NO. 28) |
| Seq1           | TCTGATCCAACCCACCTCTTC | (SEQ ID NO. 29) |
| Seq2           | CAAAACACTGAACCTCTGGG | (SEQ ID NO. 30) |

| Exon 3 |  |  |
|--------|--|--|
| Sense          | TAGGCTCTGGATATCTGCAG  | (SEQ ID NO. 31) |
| Antisense      | CTCTGTAGACTCCAATGTCC  | (SEQ ID NO. 32) |
| NSense Biotin- | CTGTTCCTCTTCCTTCCAAC  | (SEQ ID NO. 33) |
| NAntisense     | GACTCCAATGTCCCACAG    | (SEQ ID NO. 34) |
| Seq1           | AATGTCCCACAGTATCCCTG  | (SEQ ID NO. 35) |
| Seq2           | TTTGGTAGAGGTGGATCTC   | (SEQ ID NO. 36) |

| Exon 4 |  |  |
|--------|--|--|
| Sense          | ATTAGGGGCACTACCTTCAG  | (SEQ ID NO. 37) |
| Antisense      | AGGTCCTTCTATCTGTCTGG  | (SEQ ID NO. 38) |
| NSense Biotin- | ACCTTCAGGATCCTGACTTG  | (SEQ ID NO. 39) |
| NAntisense     | GTTGAATCCTTTAGCCCTAC  | (SEQ ID NO. 40) |
| Seq1           | ACTTTCTTGGCCTTAGCTGC  | (SEQ ID NO. 41) |
| Seq2           | AGAATCTGTTGTTCCAGTTC  | (SEQ ID NO. 42) |

Exon 5

| | -continued | |
|---|---|---|
| Sense | CAGTAGCAGAGATGACACTG | (SEQ ID NO. 43) |
| Antisense | TAGACAGTGTGGAGAGATGG | (SEQ ID NO. 44) |
| NSense Biotin- | CTTCTCTCATAGACACCCAC | (SEQ ID NO. 45) |
| NAntisense | AGGGAAGTGGAGCAAAAGAC | (SEQ ID NO. 46) |
| Seq1 | AGCAAAAGACAGTGGTGTTAG | (SEQ ID NO. 47) |
| Seq2 | TCCGAACACGAAACGTGTAG | (SEQ ID NO. 48) |
| Exon 6 | | |
| Sense | TGGAGGTAATTGTTCCTGCC | (SEQ ID NO. 49) |
| Antisense | CCAAACCCTCTTGGGTAATC | (SEQ ID NO. 50) |
| NSense Biotin- | TCACAGGAGCTGTTGTGAGG | (SEQ ID NO. 51) |
| NAntisense | TACTGTCTCATCCTTTACTCC | (SEQ ID NO. 52) |
| Seq1 | CTATTGTCAGCTACCGTTCC | (SEQ ID NO. 53) |
| Seq2 | GCTGATAATCAATCCCATGG | (SEQ ID NO. 54) |
| Exon 7 | | |
| Sense | TATGGACAACTGGAGAAGGG | (SEQ ID NO. 55) |
| Antisense | ACACTCTGTCTGTCTTGCTG | (SEQ ID NO. 56) |
| NSense Biotin- | TAACCTATGTGCTCCTGCTC | (SEQ ID NO. 57) |
| NAntisense | TCTTGCTGGCAGGCAGTTG | (SEQ ID NO. 58) |
| Seq1 | GTTGGCAGTTGATAGACTGC | (SEQ ID NO. 59) |
| Exon 8 | | |
| Sense | TACTCCTTTGGACAGAGCTC | (SEQ ID NO. 60) |
| Antisense | TTCCAAATCAGCCACAGTGG | (SEQ ID NO. 61) |
| NSense Biotin- | CTGACCTGGACATATCTGTC | (SEQ ID NO. 62) |
| NAntisense | TATGAGACGCAGGTGGGTTG | (SEQ ID NO. 63) |
| Seq1 | GGAAAGTTAGTACCACTTAGGG | (SEQ ID NO. 64) |
| Seq2 | AATCTCACTGACGAGGCAG | (SEQ ID NO. 65) |

Localization of the IL-2Rγ gene on chromosome Xq13.

Southern Blot Hybridization. The human and rodent parental cells, fusion procedure, and isolation and characterization of hybrids which were used have been described previously (McBride, O. W., et al. *Nucl. Acids Res.* 10: 8155–8170 (1982); McBride, O. W., et al. *J. Exp. Med.* 155: 1480–1490 (1982)). Most hybrid cells were analyzed for the presence of all human chromosomes except Y by standard isoenzyme analyses, by Southern analysis with probes from previously localized genes, and in many cases by cytogenetic analysis. DNA (10 µg) was digested with EcoRI, separated by 0.7% agarose gel electrophoresis, transferred to a nylon membrane and hybridized with a full length IL-2Rγ cDNA insert derived from pIL-2Rγ7. The hybridizations and washings were performed under high stringency conditions to allow less than 10% sequence divergence (Gnarra, et al. *Proc. Natl. Acad. Soc. USA.* 87: 3440–3444 (1990)). The IL-2Rγ gene was detected as 4.0 and 7.9 kb hybridizing EcoRI bands. Cross-hybridizing 5.9 and 4.2 kb bands were detected in Chinese hamster and mouse DNAs, respectively. The 42 human-hamster hybrids consisted of 29 Primary hybrids and 13 subclones and the 53 human-mouse hybrids represented 19 Primary hybrids and 34 subclones. Twenty of the human-hamster and 25 of the human-mouse hybrids contained the human IL-2Rγ gene. Detection of the gene was correlated with the presence or absence of each human chromosome in the group of somatic cell hybrids (Table 1).

Probes cpX289 (DXS159), pX65H7 (DXS72), and pHPGK-7e (PGK1) were obtained from the ATCC and used for Southern blot analysis of the somatic cell hybrid DNAs to permit localization of the X-chromosomal translocation breakpoint in parental cell line GM0073 to Xq13. 1–q13. 2. The pHPGK- 7e probe also identified a processed pseudogene locus (PGK1P1) for PGK1 at Xq12 (Lafreniere, et al. *Genomics* 11:352–363 (1991)).

In situ hybridization. In situ hybridization experiments were performed using peripheral blood lymphocytes from a normal male (Petrie, H. T., et al. *Eur. J. Immunol.* 20: 2813–2815 (1990); XY), as previously reported (Tory, K. F., et al. *Genomics* 13: 275–286 (1992)) (see FIG. 1(b)). Briefly, the biotinylated probe (20 ng/µg) was hybridized overnight at 37° C. in 2× SSC containing 50% formamide and 10% dextran sulfate. Washes were in 2× SSC/50% formamide, and then in 2× SSC, both at 40° C. Detection was carried out using avid in fluorescein isothiocyanate (FITC). Chromosome identification was performed following simultaneous staining with Hoechst 33258 and subsequent QFH-banding (not shown).

Linking the IL-2Rγ gene to the XSCID locus.

Mendelian Inheritance of the IL-2Rγ gene in three-generation CEPH family 1331. The pedigree of the family is shown (squares, males; circles, females) above the lanes and the alleles in each lane are indicated below the lanes (see FIG. 2(a)). Aliquots (200 ng) of genomic DNA from each individual was used as template for PCR amplification using oligonucleotide primers flanking intron 2 of the human IL-2Rγ gene and the DNA product was labeled with $^{32}$P-dCTP. Aliquots of the $^{32}$P-labeled products were diluted 1:5 in 95% formamide, denatured at 90° C., and quenched in ice water. The $^{32}$P-labeled single strand DNA was subjected to high voltage non-denaturing (5%) polyacrylamide gel electrophoreses at 23° C., dried, and autoradiographed for 30 minutes. Bands 1 and 3 were present in all DNAs in this family. Bands 2 and 4 represent allele 1 and band 5 represents allele 2. In genotypes, the designation "0" indicates hemizygosity, as inferred from the male sex and X chromosomal location of the gene.

PCR was performed in a total volume of 15 µl containing 200 ng genomic DNA, 1×PCR buffer (Promega), 1 µM of each primer, 200 µM each of dATP, dGTP, and dTTP, 25 µM dCTP with 1 µCi $^{32}$P-dCTP, and 0.45 units Taq polymerase (Promega). Initial denaturation was for 5 min at 94° C. followed by 30 cycles of 1 min each at 94° C., 55° C., and 72° C. The final extension was for 7 min at 72° C. The oligonucleotide primers used for amplification of each intron are listed above. Single stranded conformation polymorphism (SSCP) analyses were performed essentially as previously described (Orita, M., et al. *Proc. Natl. Sci. USA* 86: 2766–2770 (1989)). A 2. 5 µl aliquot of the $^{32}$P-labeled PCR product was diluted with 10 µl 95% formamide 20 µM EDTA-0.05% bromphenol blue-0.05% xylene cyanol, denatured 10 min. at 95° C., and quenched in an ice bath. Aliquots (4 μl) of the $^{32}$P-labeled single strand DNA were applied to the wells of a 30×40 cm×0.4 mm gel containing 5% polyacrylamide gel in 1×TBE pH 8.0 buffer. Electrophoresis was performed at constant power (25 watts) at room temperature with cooling from a fan blowing over a tray of ice in front of the gel, until the bands had migrated to within approximately 10 cm from the bottom of the gel. Gels were dried and band locations were determined by autoradiography; 30 minute exposures were generally sufficient.

Multipoint Linkage Analysis of IL-2Rγ With Other Loci Spanning Xcen-q22. The five loci (upper part of panel) were ordered using the CILINK program and all possible orders were considered (see FIG. 2(b)). The most likely recombination fractions between loci and the odds against reversing the order of adjacent loci (parentheses) are shown. Although DXS3 is telomeric of DXYS1, in the linkage analysis the odds (9.4×) for ordering DXYS1 and DXS3 are not significant, and the odds against reversing DXS132 and IL-2Rγ are only 7.7×10$^2$; the odds against all other orders exceeds 3×10$^3$. Lower part of panel: Two more loci (DXS159 and PGK1) were then added to this cluster, and the order and most likely recombination fractions were determined by sequential use of the programs CMAP and CILINK considering all 8 possible orders; all other orders were excluded by CMAP with odds >1000: 1. The three pairs of loci within parentheses could not be ordered with odds of even 10$^2$. The most likely recombination fractions between adjacent loci are shown including those between loci in parentheses. The total interval spanned is approximately 15 centimorgans.

Recombinants between the IL-2Rγ gene and other loci within the region Xcen-q13. Only meioses which are informative for at least two loci in addition to IL-2Rγ are shown (see FIG. 2(c)). Circles indicate informative loci which are recombinant with IL-2Rγ in a meiosis and these circles are joined by solid lines. Squares indicate loci which are non-recombinant with IL-2Rγ in a meiosis and these points are joined by dashed lines. Hatched lines join adjacent circles to squares, and indicate the regions containing a recombination breakpoint in each meiosis. The absence of circles or squares at loci indicates maternal homozygosity at those loci. The order of loci is according to previous linkage studies (de Saint Basile, et al. *Proc. Natl. Sci. USA* 84: 7576–7579 (1987); Puck, J. M., et al. *J. Clin. Invest.* 79: 1395–1400 (1987); Puck, J. M., et al. *Cytogenet. and Cell Genet.* 58: 2082 (1992); Mahtani, M. M., et al. *Genomics* 10: 849–857 (1991)) and physical mapping studies (Cremers, et al. *Am. J. Hum. Genet.* 43: 452–461 (1988); Lafreniere, et al. *Genomics* 11: 352–363 (1991)), but the distances between these loci are not proportional to genetic distance. The IL-2Rγ gene must be telomeric to DXS132 based upon individuals 134013, 134106, 134707, and 1329207. Recombinants of DXYS1 and/or DXS3 in individuals 133106, 134703, 134707, and 140806 indicate that the gene must be centromeric to these loci. Thus, the shaded area between DSX132 and DXYS1 indicates the region containing the IL-2Rγ gene. Double recombinants in proximal Xq were found in individuals 1708 and 133108.

The region delimiting the IL-2Rγ gene can be substantially further reduced by combining the results of physical mapping studies with the genetic linkage studies. Lafreniere, et al. demonstrated that the X-chromosome translocation breakpoint in parental cell line GM0073 is at the boundary of q13.1 and q13.2 (Genomics 11: 352–363 (1991)). PGK1, DXS72, DXYS1, and DXS3 are all telomeric to this breakpoint whereas DXS159/DXS467, DXS153, DXS106, and DXS132 are all centromeric to the breakpoint (indicated by the arrow in the legend in FIG. 2(c)). The locus for IL-2Rγ lies between DXS132 and the 0073 breakpoint. These results were confirmed by Southern blot analysis of the somatic cell hybrid DNAs with probes pHPGK-7e identifying the PGK1 gene and PGKP1 pseudogene loci, cpX289 (DXS159), and pX65H7 (DXS72).

XSCID patients have mutations in the IL-2Rγ chain gene.

Pedigrees and histories of the XSCID patients studied (see FIG. 3 (a)). Patient 1 was diagnosed at 11 weeks of age when he presented with failure to thrive, treatment resistant oral candidiasis and disseminated adenoviral infection. Recurrent pneumonias began at 4 mos. of age. At diagnosis, his IgG level was 18 mg/dl (normal range, 294–2069), IgM was 14 (normal range, 41–149), IgA and IgE were undetectable. Peripheral absolute lymphocyte counts range from 100–1000/mm$^3$ with 65–83% CD19+ B cells, and consistently <10% CD3+ T cells. There was no proliferation to phytohemagglutinin (PHA), nor detectable T-cell or natural killer (NK) cell cytotoxicity. No maternal engraftment was detected by RFLP analysis. Patient 1 died 43 days after a T-depleted bone marrow transplant from his mother, of progressive adenoviral infection and scopulariopsis pneumonia and fungemia.

Patent 2 was diagnosed with Penumocystis carinii pneumonitis at 3 months of age. At 5 months of age, his IgM level was 6 mg/dl (normal range, 33–108), IgA and IgE were undetectable, IgG was 162 mg/dl (normal range, 172–814), while receiving intravenous IgG. Absolute lymphocyte counts varied from 900–1600/mm$^3$, with 62–78% IgM+ B cells expressing either κ or α and 23–28% CD3+ T cells, approximately half of which expressed α/β T-cell receptors. Engraftment of maternal T cells was confirmed by RFLP analysis. Proliferation to PHA was 4% of control. The patient's cells did not generate T cell cytotoxicity in vitro and NK cytotoxicity, while measurable, was below the normal range. Patient 2 underwent a T-depleted haploidentical transplant from his father. Two months post-transplant, he developed disseminated EBV lymphoproliferative syndrome (with markedly elevated oligoclonal IgG and IgM). This condition was successfully treated with α-interferon. One year post-transplant, he shows evidence of donor T cells and has normal serum levels of IgA, IgM and IgE. She had one brother who died of SCID. The small squares and triangle indicate miscarriages (two male and One of undetermined sex) (FIG. 3 (a)).

Patent 3's early clinical course and immune function have been reported (South, M. A., et al. *Pediatric Res.* 11: 71–78 (1977); Shearer, W. T., et al. *N. Eng. J. Med.* 312: 1151–1159 (1985)). Diagnosis was made based upon clinical course and family history of a male sibling with SCID. A male cousin who died had normal immune function and did not have SCID. Patient 3's immunodeficiency was characterized by panhypogammaglobulinemia, lymphopenia with diminished T cells (10–40% varying over 12 years), elevated B-cells (30–80%), and essentially absent proliferation to mitogens or antigens. Following T-depleted hapoidentical bone marrow transplantation from his sister, there was no improvement in immune function. He died 124 days post-transplant from an EBV associated lymphoproliferative syndrome.

Sequencing of XSCID IL-2Rγ gene sequences.

B lymphocytes from patients 1 and 2 were immortalized by Epstein-Barr virus (EBV) as described previously (Tosato, G. *In Current Protocols in Immunology* (J. E. Coligan, et al., editors) 2: 7.22.1–7.22.3 (1991)). For patient 3, an autologous B cell line, DV-1, was established from bone marrow obtained post mortem (Rosenblatt, et al. *Pediatric Res.* 21: 331–337 (1987)). DNA was isolated from approximately $10^8$ cells using the Oncor genomic DNA isolation kit. To obtain genomic sequences, 2-step PCR reactions were performed using a DNA Thermal Cycler (Perkin Elmer Cetus 9600) and oligonucleotides shown above. For each exon, a first PCR reaction was performed with the appropriate Sense and Antisense oligonucleotides. The second nested PCR was performed with NSense (nested, sense) and NAntisense (nested, antisense) oligonucleotides. Each NSense oligonucleotide was biotinylated at its 5' end. 100 μl PCR reactions contained 350 ng of template genomic DNA in 50 mM KCl, 10 mM Tris-HCl PH 8.3, 1.5 mM $MgCl_2$, 0.01% gelatin, 1 μM of each oligonucleotide primer, 200 μM of each dNTP, and 2.5 units of Pfu DNA polymerase (Stratagene). Samples were denatured for 4 min at 94° C., and then amplified for 35 cycles of 1 min each at 94° C., 55° C. or 62° C., and 72° C. First PCR products were subsequently purified and 5 μl of purified PCR product was used as a template for a second, nested, PCR reaction. Second PCR reactions were performed using 4 minutes of initial denaturation, then 30 cycles of 30 seconds each at 94° C., 55° C., and 72° C. and final extension for 10 minutes. PCR products were purified by gel filtration and the biotinylated strand was isolated using Dynabeads M280 Streptavidin (DYNAL) and sequenced on the beads by the dideoxy method using Sequenase 2.0 (U.S. Biochemical Corporation). For each exon, genomic sequencing was performed with oligonucleotide primers Seq1 (each seq1 annealed near the end of the nested PCR fragment) and Seq2 (located approximately in the middle of the exon, except in the case of exon 7 where a second sequencing oligonucleotide was not needed). The Sense, Antisense, Nsense, NAntisense, and Seq1 sequences were located within noncoding regions.

Luciferase Assays Using Promoter.

A 641 bp promoter fragment (−606 to +35) was generated by PCR as described above using oligonucleotides γPro1 and γPro2 having sequences 5'-GATGGGAAGCT-TGAAGC TAGTA-3' (SEQ ID NO. 66) and 5'-GTAC-TAAAGC TTGGCGCTTGCTCTTC ATTCC-3' (SEQ ID NO. 67), respectively. The naturally occurring Hind III site is underlined. The PCR product was digested with Hind III and cloned into pLucO, a promoterless negative control vector which contains the luciferase cDNA downstream of a Hind III cloning site. pLucO was derived from pCMV-Luc (Liu, J. M., et al. *Virology* 182: 361–364 (1991)) by replacement of the CMV promoter with the Xho I to Hind III fragment derived from the multiple cloning site of pBluescript II. Transient transfection of Jurkat T cells was performed using 5 μg of DNA, 500 μg/ml of DEAE dextran, and a 30 minute incubation with cells, as previously described (Cross, S. L., et al. *Cell* 49: 47–56 (1987)). Forty eight hours following transfection, cells were harvested and lysed by sequential freezing and thawing, and luciferase activity (relative luciferase units, RLU) was determined using a Monolite 2010 Model Luminometer (Analytical Luminescence) and the Promega Luciferase Assay System Kit.

Results.

IL-2Rγ is located on Chromosome Xq13.

The chromosomal location of the IL-2Rγ gene was determined using a full length IL-2Rγ cDNA probe and Southern blot analysis of EcoR I digested DNAs from a panel of human-rodent somatic cell hybrids. An examination of the entire panel of hybrids revealed a perfect correlation between the presence of the IL-2Rγ gene and the presence of the human X chromosome (Table 1). The IL-2Rγ gene could therefore be unambiguously assigned to the human X-chromosome, and it segregated discordantly (greater than or equal to 34%) with all other human chromosomes (Table 1). Discordancy represents the presence of the gene in the absence of the chromosome (±) or the absence of the gene despite the presence of the chromosome (±), and the sum of these numbers divided by total hybrids examined (×100) represents % discordancy.

Analysis of hybrids containing specific translocations and breaks involving the X-chromosome permitted regional localization of the gene. One humanmouse hybrid containing the human IL-2Rγ gene retained only the long arm of the human X chromosome translocated to a mouse chromosome, indicating that the gene must be located on the long arm of X. Hybrids isolated after fusing human fibroblasts (GM0073) containing a well characterized X;14 reciprocal chromosome translocation with Chinese hamster cells (McBride, et al. *Nuc. Acids. Res.* 10: 8155–8170 (5982)) provided additional information. Nine independent hybrids retained the Xq13-qter translocation chromosome in the absence of the reciprocal translocation chromosome and normal X, and the human IL-2Rγ gene was absent in all these hybrids. In contrast, the human IL-2Rγ gene was present in each of four independent hybrids that retained only the Xpter-q13

TABLE 1

Segregation of the IL-2Rγ gene with the human X chromosome.

| Human Chromosome | Gene/Chromosome | | | | % Discordancy |
|---|---|---|---|---|---|
| | +/+ | +/− | −/+ | −/− | |
| 1 | 18 | 27 | 16 | 34 | 45 |
| 2 | 13 | 32 | 14 | 36 | 48 |
| 3 | 21 | 24 | 14 | 36 | 40 |
| 4 | 31 | 14 | 29 | 21 | 45 |
| 5 | 16 | 29 | 9 | 41 | 40 |
| 6 | 25 | 20 | 23 | 27 | 45 |
| 7 | 18 | 27 | 21 | 29 | 51 |
| 8 | 13 | 32 | 13 | 37 | 47 |
| 9 | 16 | 29 | 16 | 34 | 47 |
| 10 | 12 | 33 | 7 | 43 | 42 |
| 11 | 17 | 28 | 15 | 35 | 45 |
| 12 | 20 | 25 | 17 | 33 | 44 |
| 13 | 17 | 28 | 17 | 33 | 47 |
| 14 | 24 | 21 | 18 | 32 | 41 |
| 15 | 23 | 22 | 24 | 26 | 48 |
| 16 | 19 | 26 | 18 | 32 | 46 |
| 17 | 27 | 18 | 29 | 21 | 49 |
| 18 | 29 | 16 | 20 | 30 | 38 |
| 19 | 15 | 30 | 14 | 36 | 46 |
| 20 | 21 | 24 | 19 | 31 | 45 |
| 21 | 36 | 9 | 26 | 24 | 37 |
| 22 | 16 | 29 | 12 | 38 | 43 |
| X | 45 | 0 | 0 | 50 | 0 | translocation chromosome. These results permit localization of the gene to Xcen-q13. Results with several other hybrids containing spontaneous breaks involving human X supported this interpretation. In order to confirm this assignment, in situ chromosomal hybridization was performed utilizing plasmids containing the 7.9 and 4 kb genomic EcoR I IL-2Rγ fragments as biotinylated probes. A total of 50 metaphase spreads from one male were examined. Twenty four of the cells revealed hybridization of the IL-2Rγ probe at one or both chromatids at Xq13 (FIG. 1). Hybridization was not consistently noted at any other site.

The IL-2Rγ Gene is Tightly Linked to the Locus for XSCID.

Since IL-2Rγ is a critical T-cell signaling molecule, it was striking that this locus was in the general region previously determined to be the locus for X-linked severe combined immunodeficiency (XSCID) (de Saint Basille, G. D., et al. *Proc. Natl. Sci. USA* 84: 7576–7579 (1987); Puck, J. M., et al. *Am. J. Hum. Genet.* 44: 724–730 (1989)). Since the XSCID locus has been mapped by linkage analysis, genetic linkage analysis was therefore used to further localize the IL-2Rγ gene. Polymorphisms at the IL-2Rγ locus were sought for this purpose. No RFLPs were detected on hybridization of the IL-2Rγ cDNA to DNAs from ten unrelated individuals digested with twelve different restriction endonucleases (data not shown). The IL-2Rγ gene intron sequences were examined for di- or tri-nucleotide repeats which would facilitate the detection of microsatellite length polymorphisms but none were found. However, examination of DNAs from parents in the CEPH pedigrees (Dausset, et al. *Genomics* 6: 575–577 (1990)) demonstrated the presence of single-strand conformational polymorphisms (SSCPs) (Orita, K., et al. *Proc. Natl. Sci. USA* 86: 2766–2770 (1989)) within both introns 1 and 2 of the IL-2Rγ gene.

Figure 2A:
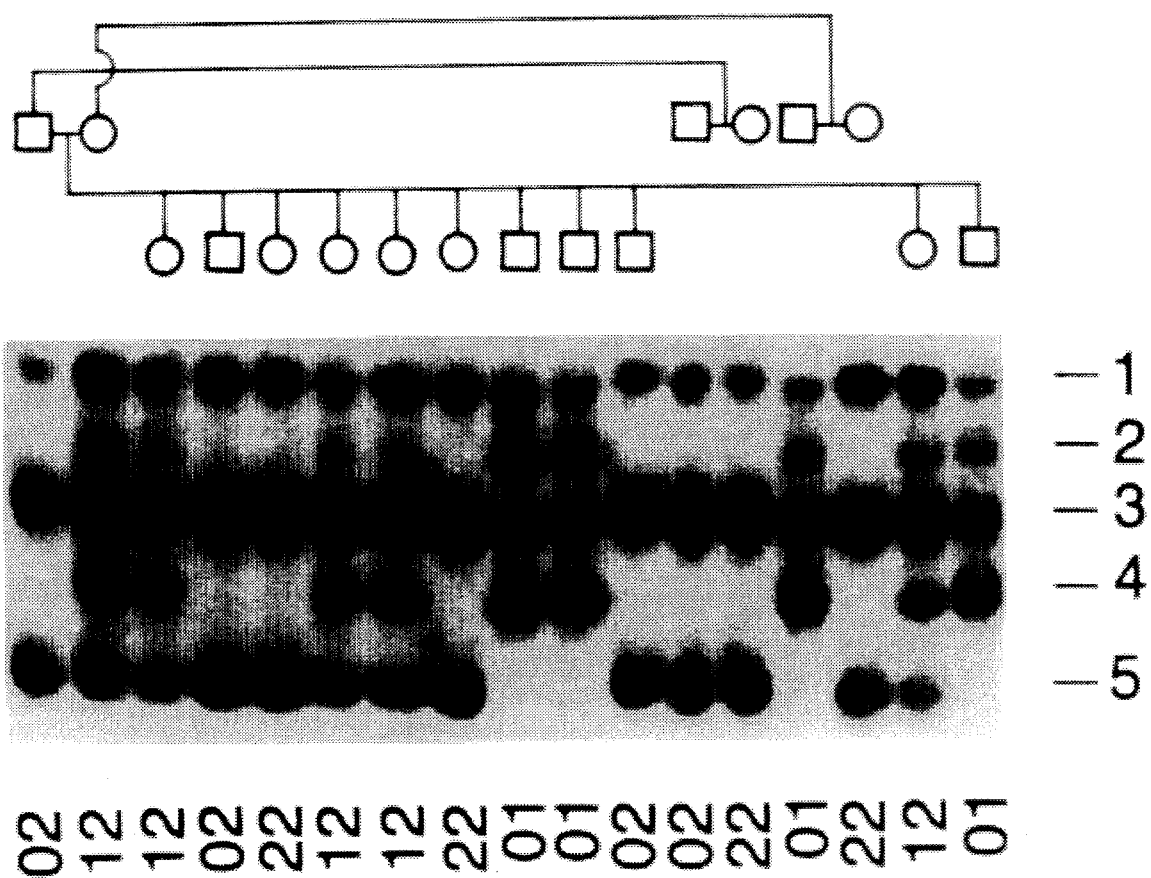
FIGS. 2(a), 2(b) and 2(c) The IL-2Rγ gene is linked to the XSCID locus.
Figure 2B:
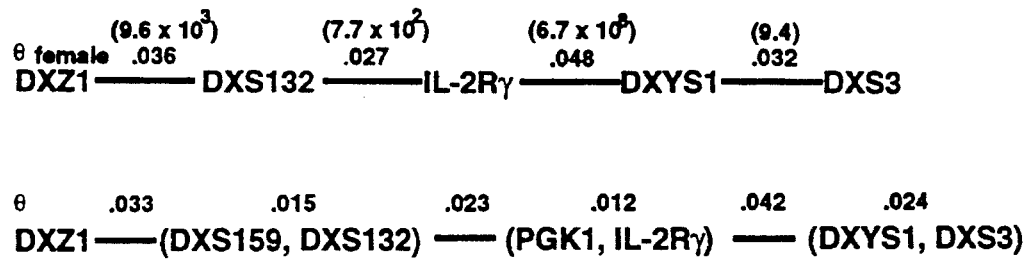

A representative SSCP analysis of intron 2 using CEPH family 1331 is shown in FIG. 2a. The segregation of band patterns within members of this family follows typical Mendelian genetics, with bands 2 and 4 representing allele 1 and band 5 representing allele 2. Bands 1 and 3 were present in all of the DNAs. The parents from each of the 40 CEPH families were examined and all members of the ten families informative for the SSCP in intron 2 were subsequently analyzed. Nineteen mothers in the CEPH pedigrees were heterozygous for the SSCP involving intron 1, and 24 of the 40 CEPH families were informative for SSCPs involving one or both of these introns. All 24 families were examined at one or both of the SSCP loci, and these results were combined as a haplotype. The data were then analyzed versus all relevant published loci in CEPH database version 5 by two-point and multipoint linkage analysis using LINKAGE version 5.10 for PC compatibles (Lathrop, et al. *Proc. Natl. Acad. Sci. USA* 81: 3443–3446 (1984)). Two point linkage analysis with other loci in the region from the centromere to band q22 on human X (Table 2) shows close linkage of IL-2Rγ to all these loci with highly significant Lod scores (Zmax scores greater than or equal to 3). The IL-2Rγ gene is most closely linked to PGK1, DXS106, and DXS132 in the Xq12-q13 region. Multipoint linkage analysis (FIG. 2(b)) was used to order the IL-2Rγ gene with respect to other loci in this region. IL-2Rγ is located very near the PGK1 gene and is distal to the DXS159 and DXS132 loci but proximal to DXYS1 and DXS3. This represents the same region to which XSCID has previously been mapped by linkage analysis in families segregating this locus (de Saint Basile, et al. *Proc. Natl. Sci. USA* 84: 7576–7579 (1987); Puck, J. M., et al. *Am. J. Hum. Genet.* 44: 724–730 (1989); Puck, J. M., et al. *Cytogenet. and Cell Genet.* 58: 2082 (1992)

Figure 2C:
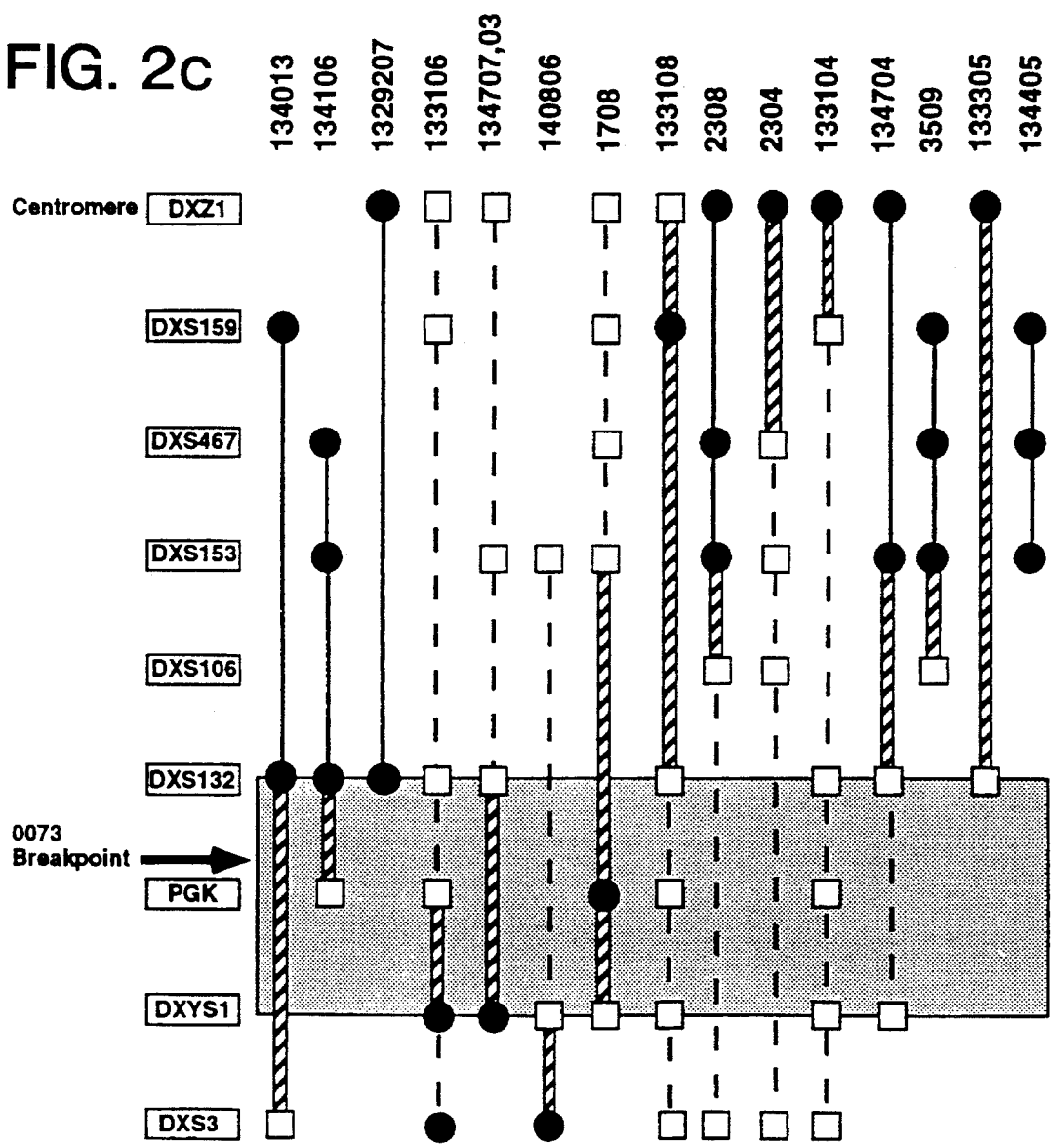

Analysis of recombination breakpoints in individual meioses (FIG. 2(c)) supports IL-2Rγ gene localization between DXS132 and DXYS1 (shaded region). Physical mapping allowed more refined mapping to the region between DXS132 and the X chromosome breakpoint location in GM0073 cells. The close linkage of the XSCID and IL-2Rγ loci

TABLE 2

Two Point Lod Scores between IL-2Rγ and other X chromosomal loci

| Loci[a] | $z_{max}$ | $\theta_{max}$[b] | |
|---|---|---|---|
| DXZ1 | 13.3 | 0.075 | (.028–.154) |
| DXS159 | 16.8 | 0.048 | (.014–.115) |
| DXS467 | 8.9 | 0.075 | (.023–.180) |
| DXS153 | 13.2 | 0.068 | (.023–.150) |
| DXS106 | 18.1 | 0.00 | (0.00–.036) |
| DXS132 | 15.1 | 0.043 | (.010–.115) |
| PGK1 | 13.8 | 0.018 | (.001–.087) |
| DXYS1X | 14.2 | 0.074 | (.028–.250) |
| DXS3 | 9.8 | 0.060 | (.025–.158) |

[a]Probe-Enzyme combinations at the various loci were: DXZ1 is pBamX-E/Xba I; DXS159 is cpX289/Pst I; DXS467 is cpX12/Rsa I; DXS153 is cX37.1/BstE II; DXS106 is cpX203/Bgl II; DXS132 is cpX23/Dra I; PGK1 is PSPT-PGK/Bgl I; DXYS1X is pDP34/Taq I; DXS3 is p19-2/Taq I.
[b]Confidence interval for $\theta_{max}$ is in parentheses.

suggests that IL-2Rγ is the XSCID gene. However, since mapping of XSCID and IL-2Rγ was performed in different sets of families, the linkage analysis could not prove their identity.

XSCID patients have mutant IL-2Rγ genes.

Figure 3A:
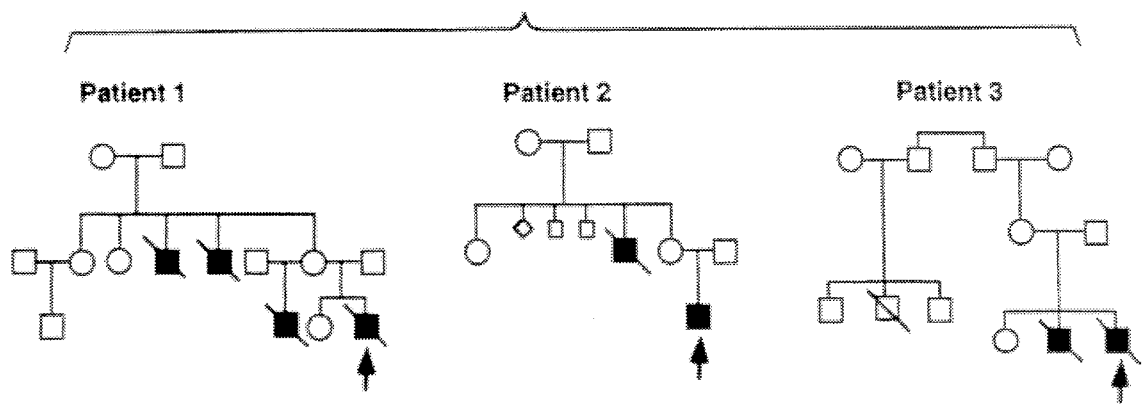
FIG. 3(a), 3(b), and 3(c). XSCID patients have mutations in the IL-2Rγ chain gene.
Figure 3B:
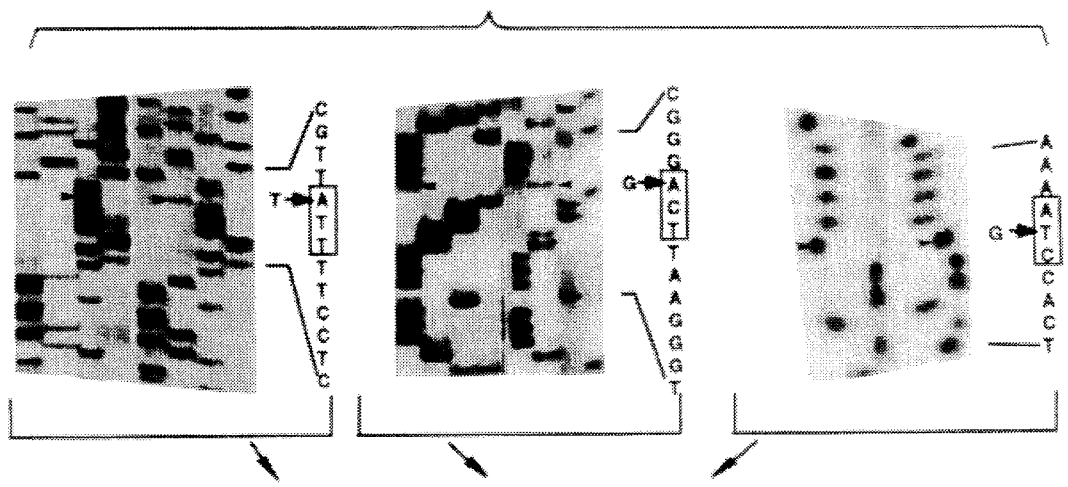
Figure 3C:
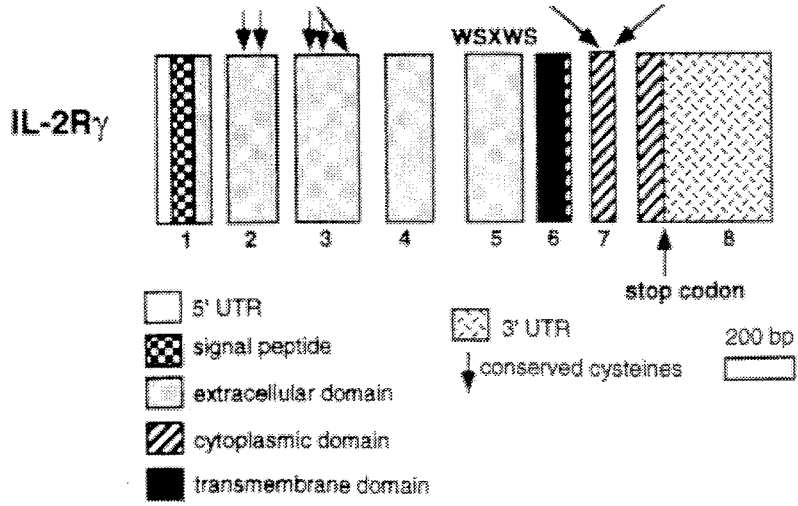

DNA was isolated from EBV lines derived from B cells from three XSCID patients. The pedigrees for these families are shown in FIG. 3(a). All were typical of XSCID both in their clinical presentations and family histories. To determine whether these individuals had large deletions or insertions in their IL-2Rγ genes, genomic Southern blot analysis was performed with multiple enzymes. All patients had normal sized fragments for each enzyme (data not shown). All eight exons for each patient were then amplified by PCR and it was found that each was normal in size by agarose gel analysis (data not shown). Having found no gross abnormality in the gene, each exon and exon/intron splice junctions were sequenced for each patient. As shown in FIG. 3b, all three patients had different point mutations resulting in premature stop codons. For each patient, the relevant area of sequencing gel containing the mutation is shown adjacent to the same area from a normal individual. In each case the normal and mutated nucleotides are identified by arrowheads; adjacent to the gel for each patient, the relevant stop codon, shown on the noncoding strand, is boxed. These occurred at lys 97, arg 267, and ser 286, in patients 1, 2, and 3, respectively, with predicted truncations of 251, 81, and 62 amino acids (FIG. 3(c)). The diagonal arrows (connecting FIG. 3(b) and 3(c)) show the positions of the predicted stop codons on a map of the exons of the IL-2Rγ gene.

Based upon the positions of the stop codons, patients 2 and 3 might be expected to express a cell surface form of IL-2Rγ. However, even if stably synthesized, the sequences predict proteins lacking the majority of the cytoplasmic domain, including substantial parts of the SH2 subdomain homology regions contained in IL-2Rγ (Takeshita, et al. *Science* 257: 379–382 (1992)). In patient 1, 251 amino acids are deleted, including the entire cytoplasmic domain, transmembrane region, and much of the extracellular domain. In contrast, no mutations were found in the normal individual. Moreover, the three patients showed no abnormalities except for their respective premature stop codons. The only variation between their sequences was that leu 33 was encoded either by CTA or CTG, a variation noted previously in IL-2Rγ cDNA and genomic clones which presumably represents a polymorphism. These data establish that XSCID is associated with mutations of the IL-2Rγ gene product. It is noteworthy that the same results were obtained for each patient when DNA was independently amplified by PCR and sequenced again. Compared to the published IL-2Rγ sequence (Takeshita, et al. *Science* 257: 379–382 (1992)), genomic DNA from a normal donor contained no mutations, nor did two IL-2Rγ cDNA clones, nor one IL-2Rγ genomic clone derived from non-XSCID sources. These data indicate that only XSCID derived DNA has been found to have mutations in the IL-2Rγ gene.

Determination of Promoter.

It was noted that the sequence of the IL-2Rγ gene upstream of the transcription initiation sites did not have canonical TATA or CAAT boxes at typical distances upstream of +1 (see FIG. 5). However, the region upstream of the initiation sites is GC rich and thus has features of a housekeeping gene. In order to determine if the 5'-flanking sequences had promoter activity, the −606 to +35 fragment was subcloned (FIG. 6(a)) upstream of the luciferase reporter gene in pLucO to generate pIL-2Rγ-Luc (see FIG. 6(b)). When transfected into Jurkat cells, pIL-2Rγ-Luc resulted in a 4.5 fold higher levels of luciferase activity than the promoterless parental vector pLucO (3910 RLU vs. 890 RLU), demonstrating that these IL-2Rγ sequences contained a functional promoter. When cloned in antisense orientation, luciferase activity was not increased, and in fact was even lower than in the promoterless control.

Discussion.

It has now been demonstrated that three out of three XSCID patients studied have mutations which truncate the IL-2 receptor γ chain. This striking result has a number of important implications:

(1) It suggests that IL-2Rγ plays a critical role in thymic maturation of bone marrow derived precursor human T-cells. A number of reports have discussed the potential role of IL-2 receptors in thymocytes. Immature (L3T4-, Lyt2-) murine thymocytes express receptors for IL-2 and can proliferate vigorously in response to IL-2 if provided with a costimulatory mitogen; more mature thymocytes express far lower levels of IL-2Rα (Raulet, D. H. *Nature* 314: 101–107 (1985); von Boehmer, H., et al. *Nature* 314: 539–540 (1985)). In fact, the initiation of CD3, CD4, and CD8 acquisition parallels down-regulation of the IL-2Rα (Petrie, H.T., et al. *Eur. J. Immunol.* 20: 2813–2815 (1990)). The levels of IL-2Rβ and IL-2Rγ have not been examined. These data regarding murine thymocytes are consistent with a role for IL-2 receptors in early thymic maturation as suggested by Tentori, et al. (*J. Exp. Med.* 168: 1741–1747 (1988)). Interestingly, however, mice made deficient of IL-2 by gene targeting are grossly normal in terms of thymocyte and peripheral T-cell subset composition (Schorle, H., et al. *Nature* 352: 621–624 (1991)), even though they have dysregulated in vitro T-cell responses and altered serum isotype levels of immunoglobulins. It is possible that IL-2 and IL-2Rγ deficiencies result in different phenotypes (i.e. IL-2Rγ mutation appears to result in a more profound loss of T cells), perhaps suggesting that IL-2Rγ may have an additional role beyond the IL-2 system (see below). Alternatively, it is possible that thymic maturation in humans and mice may differ in the degree of dependence on the IL-2/IL-2 receptor system.

(2) The critical role of IL-2Rγ in XSCID suggests that mutation of other components of the IL-2 receptor, perhaps the IL-2Rβ chain, could be responsible for certain autosomal recessive forms of SCID or less severe forms of immunodeficiency. In this regard, it is noteworthy that SCID has been associated with defective IL-2 Production (Pahwa, R., et al. *Proc. Natl. Sci. USA* 86: 5069–5073 (1989); Weinberg, K. and Parkman, R. *N. Eng. J. Med.* 24: 1718–1723 (1990)), which in one case resulted from defective production of NF-AT, a nuclear factor required for IL-2 gene transcription (Chatila, T., et al. *Proc. Natl. Acad. Sci. USA* 87: 10033–10037 (1990)). However, the patient's cells were capable of producing low levels of IL-2 mRNA (Chatila, T., et al., supra), perhaps explaining why this SCID patient had T-cells, and consistent with the possibility that the amount of IL-2 produced was sufficient for a degree of thymic maturation but not for normal mature T-cell immune function in the periphery.

Weinberg and Parkman described a phenotypically similar patient. In that case, however, no IL-2 mRNA was detectable in peripheral blood T cells activated with mitogens (Weinberg, K. and Parkman, R., supra). Although peripheral T cells were present, some circulating cells appeared to be thymocytes, consistent with a thymic maturation defect. The basis for the lack of IL-2 mRNA production in this patient is unknown, particularly since genomic Southern blot analysis revealed that the IL-2 gene was grossly intact. It is therefore unknown whether some IL-2 could have been produced within the thymus, allowing the degree of maturation seen.

These two cases of IL-2 deficient SCID suggest that in humans early T cell maturation can proceed in the absence of IL-2. The apparent differences in phenotypes of SCID with deficiencies in IL-2 versus IL-2Rγ is consistent with IL-2Rγ being a critical component of more than one cytokine receptor. Although there is no evidence yet in support of this possibility, such a system would be analogous to the IL-3, IL-5, and GM-CSF receptors which share a common β chain (Kitamura, et al. *Cell* 66: 1165–1174 (1991); Tavernier, et al. *Cell* 66: 1174–1184 (1991)) and to the IL-6, LIF, oncostatin M, and CNTF receptors, which all used gp130 as a signaling molecule (Gearing, et al. *Science* 255: 1434–1437 (1992); Taga, et al. *Proc. Natl. Sci. USA* 89: 10998–11001 (1992)). Such a model could explain why defects in IL-2Rγ, as compared to defects in IL-2, appear to have a profound impact on the degree of T-cell maturation.

(3) Because XSCID individuals can recover B-cell function following T-cell engraftment, the data suggest that the absence of IL-2Rγ expression in B-cells can be significantly compensated for by the presence of normal T-cells during terminal B cell activation and differentiation.

(4) It is noteworthy that three distinct mutations were found in examining three patients. This may suggest that there is no single dominant mutation as is found for example, in cystic fibrosis (reviewed in Fanen, et al. *Genomics* 13: 770–776 (1992)). In a severe X-linked disease, assuming constant prevalence of the disease, new mutations must constantly arise to replace the mutant X chromosomes (in males) which are not passed on to the next generation, so that a variety of mutations would be expected. All three mutations are predicted to result in large truncations of IL-2Rγ protein. Other types of point mutations such as those which affect residues required for IL-2 binding, would also be expected to be found if DNA from enough XSCID patients were sequenced. It also is reasonable to speculate that less severe phenotypes will also be found, resulting from mutations which diminish but do not abrogate IL-2Rγ chain function.

(5) Finally, these findings have important implications for prenatal and post-natal diagnosis, carrier female identification, and gene therapy of XSCID.

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

---

What is claimed is:

1. A method for diagnosing XSCID in a human male subject or determining whether a human female subject is a carrier of XSCID comprising determining whether the subject possesses a mutated IL-2Rγ gene, the presence of the mutated IL-?Rγ gene being indicative that the male subject has XSCID or the female subject is a carrier of XSCID.

2. The method of claim 1, wherein the mutated IL-2Rγ gene has a mutation in a coding region.

3. The method of claim 1, wherein the mutated IL-2Rγ gene has a mutation in a noncoding region.

4. The method of claim 1, wherein the mutated IL-2Rγ gene has one or more point mutations.

5. The method of claim 1, wherein the mutated IL-2Rγ gene has one or more deletion, insertion, or rearrangement mutations.

6. The method of claim 1, wherein the determining comprises sequencing nucleic acid from the subject and comparing the sequenced nucleic acid with the sequence of a normal IL-2Rγ gene, any difference in sequences being indicative of the mutated IL-2Rγ gene.

7. The method of claim 6, wherein the nucleic acid from the subject is amplified using PCR prior to sequencing.

8. The method of claim 6, wherein the nucleic acid from the subject is hybridized with a probe from a normal IL-2Rγ gene prior to sequencing.

9. The method of claim 1, wherein the determining comprises contacting genomic DNA from the subject or cDNA synthesized by reverse transcription of mRNA from the subject with IL-2Rγ primers from a normal IL-2Rγ gene, wherein the primers are capable of amplifying a portion of the genomic DNA or cDNA, detecting no amplification of genomic DNA or cDNA, thereby determining that the subject possesses the mutated IL-2Rγ gene.

10. The method of claim 9, wherein the nucleic acid is digested with one or more restriction enzymes and separated according to size by electrophoresis prior to contact with the IL-2Rγ primers.

11. The method of claim 9, wherein one of the primers is labeled with a detectable marker.

12. The method of claim 9, wherein the primers are selected from the group consisting of:

| | |
|---|---|
| GAATGAAGACACCACAGCTG | (SEQ ID NO. 3); |
| GGGCATAGTGGTCAGGAAG | (SEQ ID NO. 4); |
| GATGAAGAAGAGGTGGGTTG | (SEQ ID NO. 5); |
| GTTGGAAGGAAGAGGAACAG | (SEQ ID NO. 6); |

-continued

| | |
|---|---|
| AGGGATACTGTGGGACATTG | (SEQ ID NO. 7); |
| AGTCAGGATCCTGAAGGTAG | (SEQ ID NO. 8); |
| AGTGACTAGGGACGTGAATG | (SEQ ID NO. 9); |
| GTGGGTGTCTATGAGAGAAG | (SEQ ID NO. 10); |
| GACCTAATATCAAGCTCCTG | (SEQ ID NO. 11); |
| GTCTATCTGGTATCAGGAAG | (SEQ ID NO. 12); |
| TGTCTTTTGCTCCACTTCCC | (SEQ ID NO. 13); |
| AGGCAGGAACAATTACCTCC | (SEQ ID NO. 14); |
| AGCTGACAATAGCAGAGGAG | (SEQ ID NO. 15); |
| TCACCCTTCTCCAGTTGTC | (SEQ ID NO. 16); |
| GCAGTCTATCAACTGCCAAC | (SEQ ID NO. 17); |
| GACAGATATGTCCAGGTCAG | (SEQ ID NO. 18); |
| AAGGTTCTTTCCACCGGAAG | (SEQ ID NO. 19); |
| TGATTGTAATTGGCCAGTGGC | (SEQ ID NO. 20); |
| ATGACAGAGGAAACGTGTGG | (SEQ ID NO. 21); |
| CAGGCACCAGATCTCTGTAG | (SEQ ID NO. 22); |
| ACAGCCACCCTTCTCACCAG | (SEQ ID NO. 23); |
| GCAGCTGCAGGAATAAGAGG | (SEQ ID NO. 24); |
| ATTACAGACATGAGCCACCG | (SEQ ID NO. 25); |
| CCCTCTCTCTTGGTCTCTG | (SEQ ID NO. 26); |
| CTCCTTCTCACCATCATTTC | (SEQ ID NO. 27); |
| CTTGGTCTCTGATCCAACCC | (SEQ ID NO. 28); |
| TCTGATCCAACCCACCTCTTC | (SEQ ID NO. 29); |
| CAAAACACTGAACCTCTGGG | (SEQ ID NO. 30); |
| TAGGCTCTGGATATCTGCAG | (SEQ ID NO. 31); |
| CTCTGTAGACTCCAATGTCC | (SEQ ID NO. 32); |
| CTGTTCCTCTTCCTTCCAAC | (SEQ ID NO. 33); |
| GACTCCAATGTCCCACAG | (SEQ ID NO. 34); |
| AATGTCCCACAGTATCCCTG | (SEQ ID NO. 35); |
| TTTGGTAGAGGTGGATCTC | (SEQ ID NO. 36); |
| ATTAGGGGCACTACCTTCAG | (SEQ ID NO. 37); |
| AGGTCCTTCTATCTGTCTGG | (SEQ ID NO. 38); |
| ACCTTCAGGATCCTGACTTG | (SEQ ID NO. 39); |
| GTTGAATCCTTTAGCCCTAC | (SEQ ID NO. 40); |
| ACTTTCTTGGCCTTAGCTGC | (SEQ ID NO. 41); |
| AGAATCTGTTGTTCCAGTTC | (SEQ ID NO. 42); |
| CAGTAGCAGAGATGACACTG | (SEQ ID NO. 43); |
| TAGACAGTGTGGAGAGATGG | (SEQ ID NO. 44); |
| CTTCTCTCATAGACACCCAC | (SEQ ID NO. 45); |
| AGGGAAGTGGAGCAAAAGAC | (SEQ ID NO. 46); |
| AGCAAAAGACAGTGGTGTTAG | (SEQ ID NO. 47); |
| TCCGAACACGAAACGTGTAG | (SEQ ID NO. 48); |
| TGGAGGTAATTGTTCCTGCC | (SEQ ID NO. 49); |
| CCAAACCCTCTTGGGTAATC | (SEQ ID NO. 50); |
| TCACAGGAGCTGTTGTGAGG | (SEQ ID NO. 51); |
| TACTGTCTCATCCTTTACTCC | (SEQ ID NO. 52); |
| CTATTGTCAGCTACCGTTCC | (SEQ ID NO. 53); |
| GCTGATAATCAATCCCATGG | (SEQ ID NO. 54); |
| TATGGACAACTGGAGAAGGG | (SEQ ID NO. 55); |
| ACACTCTGTCTGTCTTGCTG | (SEQ ID NO. 56); |
| TAACCTATGTGCTCCTGCTC | (SEQ ID NO. 57); |
| TCTTGCTGGCAGGCAGTTG | (SEQ ID NO. 58); |
| GTTGGCAGTTGATAGACTGC | (SEQ ID NO. 59); |
| TACTCCTTTGGACAGAGCTC | (SEQ ID NO. 60); |
| TTCCAAATCAGCCACAGTGG | (SEQ ID NO. 61); |
| CTGACCTGGACATATCTGTC | (SEQ ID NO. 62); |
| TATGAGACGCAGGTGGGTTG | (SEQ ID NO. 63); |
| GGAAAGTTAGTACCACTTAGGG | (SEQ ID NO. 64); |
| AATCTCACTGACGAGGCAG | (SEQ ID NO. 65); |
| GATGGGAAGCTTGAAGCTAGTA | (SEQ ID NO. 66); and |
| GTACTAAAGCTTGGCGCTTGCTCTTCATTCC | (SEQ ID NO. 67). |

13. The method of claim 1, wherein the determining comprises contacting genomic DNA from the subject or cDNA synthesized by reverse transcription of mRNA from the subject with IL-2Rγ primers, wherein at least one of the primers contains an IL-2Rγ mutation from a family relative of the subject who has or had XSCID, or who is a carrier of XSCID, and wherein the primers are capable of amplifying a portion of the genomic DNA or cDNA, detecting amplification of genomic DNA or cDNA, thereby determining that the subject possesses the mutated IL-2Rγ gene.

14. The method of claim 13, wherein the nucleic acid is digested with one or more restriction enzymes and separated according to size by electrophoresis prior to contact with the IL-2Rγ primers.

15. The method of claim 13, wherein one of the primers is labeled with a detectable marker.

16. The method of claim 1, wherein the determining comprises contacting nucleic acid from the subject with a labeled IL-2Rγ probe from a normal IL-2Rγ gene, wherein the probe is capable of hybridizing to the nucleic acid from the subject, detecting no hybridization of the IL-2Rγ probe to the nucleic acid, thereby determining that the subject possesses the mutated IL-2Rγ gene.

17. The method of claim 16, wherein the nucleic acid is digested with one or more restriction enzymes and separated according to size by electrophoresis prior to contact with the labeled IL-2Rγ probe.

18. The method of claim 16, wherein the nucleic acid is amplified using PCR prior to contact with the labeled IL-2Rγ probe.

19. The method of claim 16, wherein the IL-2Rγ probe is DNA, cDNA, or RNA.

20. The method of claim 1, wherein the determining comprises contacting nucleic acid from the subject with a labeled IL-2Rγ probe which contains an IL-2Rγ mutation from a family relative of the subject who has or had XSCID, or who is a carrier of XSCID, wherein the probe is capable of hybridizing to the nucleic acid from the subject, detecting hybridization of the IL-2Rγ probe to the nucleic acid, thereby determining that the subject possesses the mutated IL-2Rγ gene.

21. The method of claim 20, wherein the nucleic acid is digested with one or more restriction enzymes and separated according to size by electrophoresis prior to contact with the labeled IL-2Rγ probe.

22. The method of claim 20, wherein the nucleic acid is amplified using PCR prior to contact with the labeled IL-2Rγ probe.

23. The method of claim 20, wherein the IL-2Rγ probe is DNA, cDNA, or RNA.

24. The method of claim 1, wherein the determining comprises measuring the level of IL-2Rγ mRNA from the subject and comparing the level of IL-2Rγ mRNA so measured with the level of IL-2Rγ mRNA expressed by a normal IL-2Rγ gene, the presence of a lower level of IL-2Rγ mRNA or an absence of mRNA expression from the subject being indicative of the mutated IL-2Rγ gene.

25. The method of claim 24, wherein the IL-2Rγ mRNA is measured using Northern blotting, dot and slot hybridization, S1 nuclease assay, or ribonuclease assay.

26. The method of claim 1, wherein the determining comprises using single stranded conformational polymorphisms (SSCPs) to determine the mutation.

27. A kit for diagnosing XSCID in a human male subject or determining whether a human female subject is a carrier of XSCID comprising: IL-2Rγ primers capable of amplifying a portion of genomic DNA, or a portion of cDNA synthesized by reverse transcription of mRNA from the subject; and a standard nucleic acid having a nucleotide sequence selected from the normal I L-2Rγ nucleotide sequence in the region encompassed by said primers or said portion of cDNA, for determining at least one difference in nucleotide sequence of the subject's DNA, said difference in said subject's sequence compared with the standard sequence indicates that the male subject has XSCID or the female subject is a carrier of XSCID.

28. The kit of claim 32, wherein the primers are selected from the group consisting of:

| | |
|---|---|
| GAATGAAGACACCACAGCTG | (SEQ ID NO. 3); |
| GGGCATAGTGGTCAGGAAG | (SEQ ID NO. 4); |
| GATGAAGAAGAGGTGGGTTG | (SEQ ID NO. 5); |
| GTTGGAAGGAAGAGGAACAG | (SEQ ID NO. 6); |
| AGGGATACTGTGGGACATTG | (SEQ ID NO. 7); |
| AGTCAGGATCCTGAAGGTAG | (SEQ ID NO. 8); |
| AGTGACTAGGGACGTGAATG | (SEQ ID NO. 9); |
| GTGGGTGTCTATGAGAGAAG | (SEQ ID NO. 10); |
| GACCTAATATCAAGCTCCTG | (SEQ ID NO. 11); |
| GTCTATCTGGTATCAGGAAG | (SEQ ID NO. 12); |
| TGTCTTTTGCTCCACTTCCC | (SEQ ID NO. 13); |
| AGGCAGGAACAATTACCTCC | (SEQ ID NO. 14); |
| AGCTGACAATAGCAGAGGAG | (SEQ ID NO. 15); |
| TCACCCTTCTCCAGTTGTC | (SEQ ID NO. 16); |
| GCAGTCTATCAACTGCCAAC | (SEQ ID NO. 17); |
| GACAGATATGTCCAGGTCAG | (SEQ ID NO. 18); |
| AAGGTTCTTTCCACCGGAAG | (SEQ ID NO. 19); |
| TGATTGTAATTGGCCAGTGGC | (SEQ ID NO. 20); |
| ATGACAGAGGAAACGTGTGG | (SEQ ID NO. 21); |
| CAGGCACCAGATCTCTGTAG | (SEQ ID NO. 22); |
| ACAGCCACCCTTCTCACCAG | (SEQ ID NO. 23); |
| GCAGCTGCAGGAATAAGAGG | (SEQ ID NO. 24); |
| ATTACAGACATGAGCCACCG | (SEQ ID NO. 25); |
| CCCTCTCTCTTGGTCTCTG | (SEQ ID NO. 26); |
| CTCCTTCTCACCATCATTTC | (SEQ ID NO. 27); |
| CTTGGTCTCTGATCCAACCC | (SEQ ID NO. 28); |
| TCTGATCCAACCCACCTCTTC | (SEQ ID NO. 29); |
| CAAAACACTGAACCTCTGGG | (SEQ ID NO. 30); |
| TAGGCTCTGGATATCTGCAG | (SEQ ID NO. 31); |
| CTCTGTAGACTCCAATGTCC | (SEQ ID NO. 32); |
| CTGTTCCTCTTCCTTCCAAC | (SEQ ID NO. 33); |
| GACTCCAATGTCCCACAG | (SEQ ID NO. 34); |
| AATGTCCCACAGTATCCCTG | (SEQ ID NO. 35); |
| TTTGGTAGAGGTGGATCTC | (SEQ ID NO. 36); |
| ATTAGGGGCACTACCTTCAG | (SEQ ID NO. 37); |
| AGGTCCTTCTATCTGTCTGG | (SEQ ID NO. 38); |
| ACCTTCAGGATCCTGACTTG | (SEQ ID NO. 39); |
| GTTGAATCCTTTAGCCCTAC | (SEQ ID NO. 40); |
| ACTTTCTTGGCCTTAGCTGC | (SEQ ID NO. 41); |
| AGAATCTGTTGTTCCAGTTC | (SEQ ID NO. 42); |
| CAGTAGCAGAGATGACACTG | (SEQ ID NO. 43); |
| TAGACAGTGTGGAGAGATGG | (SEQ ID NO. 44); |
| CTTCTCTCATAGACACCCAC | (SEQ ID NO. 45); |
| AGGGAAGTGGAGCAAAAGAC | (SEQ ID NO. 46); |
| AGCAAAAGACAGTGGTGTTAG | (SEQ ID NO. 47); |
| TCCGAACACGAAACGTGTAG | (SEQ ID NO. 48); |

| | |
|---|---|
| TGGAGGTAATTGTTCCTGCC | (SEQ ID NO. 49); |
| CCAAACCCTCTTGGGTAATC | (SEQ ID NO. 50); |
| TCACAGGAGCTGTTGTGAGG | (SEQ ID NO. 51); |
| TACTGTCTCATCCTTTACTCC | (SEQ ID NO. 52); |
| CTATTGTCAGCTACCGTTCC | (SEQ ID NO. 53); |
| GCTGATAATCAATCCCATGG | (SEQ ID NO. 54); |
| TATGGACAACTGGAGAAGGG | (SEQ ID NO. 55); |
| ACACTCTGTCTGTCTTGCTG | (SEQ ID NO. 56); |
| TAACCTATGTGCTCCTGCTC | (SEQ ID NO. 57); |
| TCTTGCTGGCAGGCAGTTG | (SEQ ID NO. 58); |
| GTTGGCAGTTGATAGACTGC | (SEQ ID NO. 59); |
| TACTCCTTTGGACAGAGCTC | (SEQ ID NO. 60); |
| TTCCAAATCAGCCACAGTGG | (SEQ ID NO. 61); |
| CTGACCTGGACATATCTGTC | (SEQ ID NO. 62); |
| TATGAGACGCAGGTGGGTTG | (SEQ ID NO. 63); |
| GGAAAGTTAGTACCACTTAGGG | (SEQ ID NO. 64); |
| AATCTCACTGACGAGGCAG | (SEQ ID NO. 65); |
| GATGGGAAGCTTGAAGCTAGTA | (SEQ ID NO. 66); and |
| GTACTAAAGCTTGGCGCTTGCTCTTCATTCC | (SEQ ID NO. 67). |

29. A kit for diagnosing XSCID in a human male subject or determining whether a human female subject is a career of XSCID comprising: a labeled IL-2Rγ probe from a normal IL-2Rγ gene capable of hybridizing to a portion of genomic DNA, or a portion of cDNA synthesized by reverse transcription of mRNA from the subject; and a standard nucleic acid having nucleotide sequence selected from the normal IL-2Rγ nucleotide sequence, for determining at least one difference in nucleotide sequence of corresponding regions of the subject's DNA, said difference in said subject's sequence compared with the standard sequence indicates that the male subject has XSCID or the female subject is a carrier of XSCID.

30. A method for diagnosing XSCID in a human male subject or determining whether a human female subject is a carrier of XSCID comprising determining whether the subject possesses a mutated IL-2Rγ gene which encodes an IL-2Rγ protein truncated by at least 62 C-terminal amino acids, said mutated IL-2Rα, gene being indicative that the male subject has XSCID or the female subject is a carrier of XSCID.

31. The method of claim 30, wherein the mutation in the IL-2Rγ gene is a mutation in a coding region.

32. The method of claim 31, wherein the mutation is a point mutation.

33. The method of claim 32 wherein the point mutation is selected from the group consisting of an AAA to TAA transversion in exon 3, resulting in truncation of the C-terminal 251 amino acids; a CGA to TGA transition in exon 7, resulting in the truncation of the C-terminal 81 amino acids; and a TCG to TAG transversion in exon 7, resulting in the truncation of the C-terminal 62 amino acids.

34. A kit for diagnosing XSCID in a human male subject or determining whether a human female subject is a carrier of XSCID comprising: IL-2Rγ primers capable of amplifying a portion of genomic DNA, or a portion of cDNA synthesized by reverse transcription of mRNA from the subject; and a standard nucleic acid having a nucleotide sequence selected from the normal IL-2Rγ nucleotide sequence in the region encompassed by said primers or said portion of cDNA, for determining at least one difference in nucleotide sequence of the subject's DNA, which difference results in the subject's DNA encoding an IL- 2Rγ protein truncated by at least 62 C-terminal amino acids, said difference in said subject's sequence compared with the standard sequence being indicative that the male subject has XSCID or the female subject is a carrier of XSCID.

35. The kit of claim 34, wherein the difference in the nucleotide sequence of the subject's DNA is a mutation in a coding region.

36. The kit of claim 35, wherein the mutation is a point mutation.

37. The kit of claim 36 wherein the point mutation is selected from the group consisting of an AAA to TAA transversion in exon 3, resulting in truncation of the C-terminal 251 amino acids; a CGA to TGA transition in exon 7, resulting in the truncation of the C-terminal 81 amino acids; and a TCG to TAG transversion in exon 7, resulting in the truncation of the C-terminal 62 amino acids.

38. The kit of claim 34, wherein one of the primers is labeled with a detectable marker.

39. The kit of claim 34, wherein the primers are selected from the group consisting of:

| | |
|---|---|
| GAATGAAGACACCCACAGCTG | (SEQ ID NO. 3), |
| GGGCATAGTGGTCAGGAAG | (SEQ ID NO. 4); |
| GATGAAGAAGAGGTGGGTTG | (SEQ ID NO. 5); |
| GTTGGAAGGAAGAGGAACAG | (SEQ ID NO. 6); |
| AGGGATACTGTGGGACATTG | (SEQ ID NO. 7); |
| AGTCAGGATCCTGAAGOTAG | (SEQ ID NO. 8); |
| AGTGACTAGGGACGTGAATG | (SEQ ID NO. 9); |
| GTGGGTGTCTATGAGAGAAG | (SEQ ID NO. 10); |
| GACCTAATATCAAGCTCCTG | (SEQ ID NO. 11); |
| GTCTATCTGGTATCAGGAAG | (SEQ ID NO. 12); |
| TGTCTTTTGCTCCACTTCCC | (SEQ ID NO. 13); |
| AGGCAGGAACAATTACCTCC | (SEQ ID NO. 14); |
| AGCTGACAATAGCAGAGGAG | (SEQ ID NO. 15); |
| TCACCCTTCTCCAGTTGTC | (SEQ ID NO. 16); |
| GCAGTCTATCAACTGCCAAC | (SEQ ID NO. 17); |
| GACAGATATOTCCAGGTCAG | (SEQ ID NO. 18); |

| | |
|---|---|
| AAGGTTCTTTCCACCGGAAG | (SEQ ID NO. 19); |
| TGATTGTAATTGGCCAGTGGC | (SEQ ID NO. 20); |
| ATGACAGAGGAAACGTGTGG | (SEQ ID NO. 21); |
| CAGGCACCAGATCTCTGTAG | (SEQ ID NO. 22); |
| ACAGCCACCCTTCTCACCAG | (SEQ ID NO. 23); |
| GCAGCTGCAGGAATAAGAGG | (SEQ ID NO. 24); |
| ATTACAGACATGAGCCACCG | (SEQ ID NO. 25); |
| CCCTCTCTCTTGGTCTCTG | (SEQ ID NO. 26); |
| CTCCTTCTCACCATCATTTC | (SEQ ID NO. 27); |
| CTTGGTCTCTGATCCAACCC | (SEQ ID NO. 28); |
| TCTGATCCAACCCACCTCTTC | (SEQ ID NO. 29); |
| CAAAACACTGAACCTCTGGG | (SEQ ID NO. 30); |
| TAGGCTCTGGATATCTGCAG | (SEQ ID NO. 31); |
| CTCTGTAGACTCCAATGTCC | (SEQ ID NO. 32); |
| CTGTTCCTCTTCCTTCCAAC | (SEQ ID NO. 33); |
| GACTCCAATGTCCCACAG | (SEQ ID NO. 34); |
| AATGTCCCACAGTATCCCTG | (SEQ ID NO. 35); |
| TTTGGTAGAGGTGGATCTC | (SEQ ID NO. 36); |
| ATTAGGGGCACTACCTTCAG | (SEQ ID NO. 37); |
| AGGTCCTTCTATCTGTCTGG | (SEQ ID NO. 38), |
| ACCTTCAGGATCCTGACTTG | (SEQ ID NO. 39); |
| GTTGAATCCMAGCCCTAC | (SEQ ID NO. 40); |
| ACTTTCTTGGCCTTAGCTGC | (SEQ ID NO. 41); |
| AGAATCTGTTGTTCCAGTTC | (SEQ ID NO. 42); |
| CAGTAGCAGAGATGACACTG | (SEQ ID NO. 43); |
| TAGACAGTGTGGAGAGATGG | (SEQ ID NO. 44); |
| CTTCTCRCATAGACACCCAC | (SEQ ID NO. 45); |
| AGGGAAGTGGAGCAAAACAC | (SEQ ID NO. 46); |
| AGCAAAAGACAGTGGTGTTAG | (SEQ ID NO. 47); |
| TCCGAACACGAAACGTGTAG | (SEQ ID NO. 48); |
| TGGAGGTAATTGTTCCTGCC | (SEQ ID NO. 49); |
| CCAAACCCTCTTGGGTAATC | (SEQ ID NO. 50); |
| TCACAGGAGCTGTTGTGAGG | (SEQ ID NO. 51); |
| TACTGTCTCATCCTTTACTCC | (SEQ ID NO. 52); |
| CTATTGTCAGCTACCGTTCC | (SEQ ID NO. 53); |
| GCTGATAATCAATCCCATGG | (SEQ ID NO. 54); |
| TATGGACAACTGGAGAAGGG | (SEQ ID NO. 55); |
| ACACTCTGTCTGTCTTGCTG | (SEQ ID NO. 56); |
| TAACCTATGTGCTCCTGCTC | (SEQ ID NO. 57); |
| TCTRGCTGGCAGGCAGTTG | (SEQ ID NO. 58); |
| GTTGGCAGTTGATAGACTGC | (SEQ ID NO. 59); |
| TACTCCTTTGGACAGAGCTC | (SEQ ID NO. 60); |
| TTCCAAATCAGCCACAGTGG | (SEQ ID NO. 61); |
| CTGACCTG(3ACATATCTGTC | (SEQ ID NO. 62); |
| TATGAGACGCAGGTGGGTTG | (SEQ ID NO. 63); |
| GGAAAGTTAGTACCACTTAGGG | (SEQ ID NO. 64); |
| AATCTCACTGACGAGGCAG | (SEQ ID NO. 65); |
| GATGGGAAGCTTGAAGCTAGTA | (SEQ ID NO. 66); and |
| GTACTAAAGCTTGGCGCTTGCTCTRCATTCC | (SEQ ID NO. 67). |

40. The kit of claim 39, wherein one of the primers is labeled with a detectable marker.

41. A kit for diagnosing XSCID in a human male subject or determining whether a human female subject is a carrier of XSCID comprising: a labeled IL-2Rγ probe from a normal IL-2Rγ gene capable of hybridizing to a portion of genomic DNA, or a pertion of cDNA synthesized by reverse transcription of mRNA from the subject; and a standard nucleic acid having nucleotide sequence selected from the normal IL2Rγ nucleotide sequence, for determining at least one difference in nucleotide sequence of corresponding regions of the subject's DNA, which difference results in the subject 's DNA encoding an IL-2Rγ protein truncated by at least 62 C-terminal amino acids, said difference in said subject 's sequence compared with the standard sequence being indicative that the male subject has XSCID or the female subject is a carrier of XSCID.

42. The kit of claim 41, wherein the difference in the nucleotide sequence of the subject's DNA is a mutation in a coding region.

43. The kit of claim 42, wherein the mutation is a point mutation.

44. The kit of claim 43 wherein the point mutation is selected from the group consisting of an AAA to TAA transversion in exert 3, resulting in truncation of the C-terminal 251 amino acids; a CGA to TGA transition in exert 7, resulting in the truncation of the C-terminal 81 amino acids; and a TCG to TAG transversion in exon 7, resulting in the truncation of the C-terminal 62 amino acids.

* * * * *

UNITED STATES PATENT AND TRADEMARK OFFICE
CERTIFICATE OF CORRECTION

Page 1 of 4

PATENT NO. : 5,518,880
DATED : May 21, 1996
INVENTOR(S) : Leonard, Warren J., Noguchi, Masayuki, McBride, Wesley It is certified that error appears in the above-indentified patent and that said Letters Patent is hereby corrected as shown below:

On the cover page:
In the title, delete "THEREOF" and insert --THEREFOR--.

In col. 1, line 2, in the title, delete "THEREOF" and insert --THEREFOR--.

In col. 3, line 25, delete "nitogens" and insert --mitogens--.

In col. 10, line 45, delete "audioradiography" and insert --autoradiography--.

In col. 10, line 48, delete "IL 2R$\gamma$" and insert --IL-2R$\gamma$--

In col. 10, line 59, delete "audioradiograph" and insert --autoradiograph--.

In col. 12, lines 63-64, delete "hydrid-izing" and insert --hybrid-izing--.

In col. 13, line 55, delete "adenoassociated" and insert --adeno-associated--.

In col. 16, line 38 (actual line 48), in the fifth line of SEQ ID NO: 73, delete "i" and insert --t--.

In col. 16, line 50 (actual line 62), in the fifth line of the sequence for SEQ ID NO: 74, delete "e" and insert --c--.

In col. 19, line 44, delete "Soc." and insert --Sci.--.

In col. 21, line 45, insert --Acad.-- after "Natl." and before "Sci.".

UNITED STATES PATENT AND TRADEMARK OFFICE
CERTIFICATE OF CORRECTION

PATENT NO. : 5,518,880
DATED : May 21, 1996
INVENTOR(S) : Leonard, Warren J., Noguchi, Masayuki, McBride, Wesley It is certified that error appears in the above-indentified patent and that said Letters Patent is hereby corrected as shown below:

In col. 22, line 26, delete "Penumocystis" and insert --Pneumocystis--.

In col. 22, line 58, delete "hapoidentical" and insert --haploidentical--.

In col. 23, lines 39-40, delete GATGGGAAGCTTGAAGC TAGTA" and insert --GATGGGAAGCTTGAAGCTAGTA--.

In col. 23, lines 40-41, delete "GTACTAAAGC TTGGCGCTTGCTCTTC ATTCC" and insert --GTACTAAAGCTTGGCGCTTGCTCTTCATTCC--.

In col. 24, line 12, delete "humanmouse" and insert --human-mouse--.

In col. 25, line 3, insert --Acad.-- after "Natl." and before "Sci.".

In col. 25, line 56, insert --Acad.-- after "Natl." and before "Sci.".

In col. 27, line 65, insert --Acad.-- after "Natl." and before "Sci.".

In col. 28, line 34, insert --Acad.-- after "Natl." and before "Sci.".

In claim 1, line 5, (col. 81, line 46) delete "IL-?R$\gamma$" and insert --IL-2R$\gamma$--.

In claim 27, line 7, (col. 86, line 17) delete "I L2-R$\gamma$" and insert --IL-2R$\gamma$--.

In claim 27, line 10, (col. 86, line 21) delete "subjcct's" and insert --subject's--.

In claim 28, line 1, (col. 86, line 25) delete "32" and insert --27--.

UNITED STATES PATENT AND TRADEMARK OFFICE
CERTIFICATE OF CORRECTION

PATENT NO. : 5,518,880

DATED : May 21, 1996

INVENTOR(S) : Leonard, Warren J., Noguchi, Masayuki, McBride, Wesley

It is certified that error appears in the above-indentified patent and that said Letters Patent is hereby corrected as shown below:

In claim 39, line 18 (col. 88, concerning SEQ ID NO. 18), delete "O" and insert --G--.

In claim 39, line 40 (col. 89, concerning SEQ ID NO. 40), delete "M" and insert --TTT--.

In claim 39, line 45 (col. 89, concerning SEQ ID NO. 45), delete "R" and insert --T--.

In claim 39, line 46 (col. 89, concerning SEQ ID NO. 46), delete "AGGGAAGTGGAGCAAAACAC" and insert --AGGGAAGTGGAGCAAAAGAC--.

In claim 39, line 58 (col. 89, concerning SEQ ID NO. 58), delete "R" and insert --T--.

In claim 39, line 62 (col. 89, concerning SEQ ID NO. 62), delete "(3" and insert --G--.

In claim 39, line 67 (col. 89, concerning SEQ ID NO. 67), delete "R" and insert --T--.

In claim 41, line 5, delete "pertion" and insert --portion--.

In claim 41, lines 11 and 13, delete "subject 's" and insert --subject's--.

UNITED STATES PATENT AND TRADEMARK OFFICE
CERTIFICATE OF CORRECTION

PATENT NO. : 5,518,880             Page 4 of 4

DATED : May 21, 1996

INVENTOR(S) : Leonard, Warren J., Noguchi, Masayuki, McBride, Wesley

It is certified that error appears in the above-indentified patent and that said Letters Patent is hereby corrected as shown below:

In claim 44, line 3, delete "exert" and insert --exon--.

In claim 44, line 4, delete "exert" and insert --exon--.

Signed and Sealed this

Twenty-ninth Day of April, 1997

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 76

( 2 ) INFORMATION FOR SEQ ID NO:1:

( i ) SEQUENCE CHARACTERISTICS:
( A ) LENGTH: 907
( B ) TYPE: NUCLEIC ACID
( C ) STRANDEDNESS: SINGLE
( D ) TOPOLOGY: UNKNOWN ( i i ) MOLECULE TYPE:
( A ) DESCRIPTION: OLIGONUCLEOTIDE ( i i i ) HYPOTHETICAL: NO ( i v ) ANTI-SENSE: NO ( v i ) ORIGINAL SOURCE:
( A ) ORGANISM: HUMAN
( C ) INDIVIDUAL ISOLATE: IL-2R ( x i ) SEQUENCE DESCRIPTION:SEQ ID NO:1:

```
AAGCTTGAAG  CTAGTATTGT  TGTTCCTCCA  TTTCTAGAAT  ATTTTTGTAT            50

TATAAGTCAC  ACTTCCTCGC  CAGTCTCAAC  AGGGACCCAG  CTCAGGCAGC           100

AGCTAAGGGT  GGGTATTCTG  GTTTGGATTA  GATCAGAGGA  AAGACAGCTG           150

TATATGTGCC  CACAGGAGCC  AAGACGGTAT  TTTCCATCCT  CCCAAAACAG           200

GTATGAGCTT  TGACAGAGAT  TTAAGGGTGA  CCAAGTCAAG  GAAGAGGCAT           250

GGCATAGAAC  GGTGATGTCG  GGGGTGGGGG  GTTCAGAACT  TCCATTATAG           300

AAGGTAATGA  TTTAGAGGAG  AAGGTGGTTG  AGAATGGTGC  TAGTGGTAGT           350

GAACAGATCC  TTCCCAGGAT  CTAGGTGGGC  TGAGGATTTT  TGAGTCTGTG           400

ACACTATTGT  ATATCCAGCT  TTAGTTTCTG  TTTACCACCT  TACAGCAGCA           450

CCTAATCTCC  TAGAGGACTT  AGCCCGTGTC  ACACAGCACA  TATTTGCCAC           500

ACCCTCTGTA  AAGCCCTGGT  TATAAGGTTC  TTTCCACCGG  AAGCTATGAC           550

AGAGGAAACG  TGTGGGTGGG  GAGGGGTAGT  GGGTGAGGGA  CCCAGGTTCC           600

TGACACAGAC  AGACTACACC  CAGGGAATGA  AGAGCAAGCG  CC  ATG  TTG         648
                                                    Met  Leu
                                                      1
AAG  CCA  TCA  TTA  CCA  TTC  ACA  TCC  CTC  TTA  TTC  CTG  CAG  CTG  690
Lys  Pro  Ser  Leu  Pro  Phe  Thr  Ser  Leu  Leu  Phe  Leu  Gln  Leu
          5                        10                       15

CCC  CTG  CTG  GGA  GTG  GGG  CTG  AAC  ACG  ACA  ATT  CTG  ACG  CCC  732
Pro  Leu  Leu  Gly  Val  Gly  Leu  Asn  Thr  Thr  Ile  Leu  Thr  Pro
               20                       25                       30

AAT  GGG  AAT  GAA  GAC  ACC  ACA  GCT  GGTGGGAAAT  CTGGGACTGG        776
Asn  Gly  Asn  Glu  Asp  Thr  Thr  Ala
                    35

AGGGGGCTGG  TGAGAAGGGT  GGCTGTGGGA  AGGGGCCGTA  CAGAGATCTG           826

GTGCCTGCCA  CTGGCCATTA  CAATCATGTG  GGCAGAATTG  AAAAGTGGAG           876

TGGGAAGGGC  AAGGGGGAGG  GTTCCCTCCC  T                                907
```

( 2 ) INFORMATION FOR SEQ ID NO:2:

( i ) SEQUENCE CHARACTERISTICS:
        ( A ) LENGTH: 38
        ( B ) TYPE: AMINO ACID
        ( D ) TOPOLOGY: UNKNOWN ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:2:

| Met | Leu | Lys | Pro | Ser | Leu | Pro | Phe | Thr | Ser | Leu | Leu | Phe | Leu | Gln |
|---|---|---|---|---|---|---|---|---|---|---|---|---|---|---|
| 1 | | | | 5 | | | | | 10 | | | | | 15 |

| Leu | Pro | Leu | Leu | Gly | Val | Gly | Leu | Asn | Thr | Thr | Ile | Leu | Thr | Pro |
|---|---|---|---|---|---|---|---|---|---|---|---|---|---|---|
| 20 | | | | | 25 | | | | | 30 | | | | |

| Asn | Gly | Asn | Glu | Asp | Thr | Thr | Ala |
|---|---|---|---|---|---|---|---|
| 35 | | | | | | | |

( 2 ) INFORMATION FOR SEQ ID NO:3:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:3:

GAATGAAGAC ACCACAGCTG                                                                  20

( 2 ) INFORMATION FOR SEQ ID NO:4:

( i ) SEQUENCE CHARACTERISTICS:
        ( A ) LENGTH: 19
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:4:

GGGCATAGTG GTCAGGAAG                                                                   19

( 2 ) INFORMATION FOR SEQ ID NO:5:

( i ) SEQUENCE CHARACTERISTICS:
        ( A ) LENGTH: 20
        ( B ) TYPE: NUCLEIC ACID
        ( C ) STRANDEDNESS: SINGLE (D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: NO (v i) ORIGINAL SOURCE:
(A) ORGANISM: HUMAN
(C) INDIVIDUAL ISOLATE: IL-2R (x i) SEQUENCE DESCRIPTION:SEQ ID NO:5:

GATGAAGAAG AGGTGGGTTG 20

(2) INFORMATION FOR SEQ ID NO:6:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: YES (v i) ORIGINAL SOURCE:
(A) ORGANISM: HUMAN
(C) INDIVIDUAL ISOLATE: IL-2R (x i) SEQUENCE DESCRIPTION:SEQ ID NO:6:

GTTGGAAGGA AGAGGAACAG 20

(2) INFORMATION FOR SEQ ID NO:7:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: NO (v i) ORIGINAL SOURCE:
(A) ORGANISM: HUMAN
(C) INDIVIDUAL ISOLATE: IL-2R (x i) SEQUENCE DESCRIPTION:SEQ ID NO:7:

AGGGATACTG TGGGACATTG 20

(2) INFORMATION FOR SEQ ID NO:8:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: YES ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:8:

AGTCAGGATC CTGAAGGTAG                                                                                    20

( 2 ) INFORMATION FOR SEQ ID NO:9:

( i ) SEQUENCE CHARACTERISTICS:
                ( A ) LENGTH: 20
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: NO ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:9:

AGTGACTAGG GACGTGAATG                                                                                    20

( 2 ) INFORMATION FOR SEQ ID NO:10:

( i ) SEQUENCE CHARACTERISTICS:
                ( A ) LENGTH: 20
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: YES ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:10:

GTGGGTGTCT ATGAGAGAAG                                                                                    20

( 2 ) INFORMATION FOR SEQ ID NO:11:

( i ) SEQUENCE CHARACTERISTICS:
                ( A ) LENGTH: 20
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: NO ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:11:

GACCTAATAT CAAGCTCCTG                                                                                    20

( 2 ) INFORMATION FOR SEQ ID NO:12:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:12:

GTCTATCTGG TATCAGGAAG 20

( 2 ) INFORMATION FOR SEQ ID NO:13:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:13:

TGTCTTTTGC TCCACTTCCC 20

( 2 ) INFORMATION FOR SEQ ID NO:14:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:14:

AGGCAGGAAC AATTACCTCC 20

( 2 ) INFORMATION FOR SEQ ID NO:15:

( i ) SEQUENCE CHARACTERISTICS:
        ( A ) LENGTH: 20
        ( B ) TYPE: NUCLEIC ACID
        ( C ) STRANDEDNESS: SINGLE (D) TOPOLOGY: UNKNOWN (i i) MOLECULE TYPE:
        (A) DESCRIPTION: OLIGONUCLEOTIDE (i i i) HYPOTHETICAL: NO (i v) ANTI-SENSE: NO (v i) ORIGINAL SOURCE:
        (A) ORGANISM: HUMAN
        (C) INDIVIDUAL ISOLATE: IL-2R (x i) SEQUENCE DESCRIPTION:SEQ ID NO:15:

AGCTGACAAT AGCAGAGGAG 20

(2) INFORMATION FOR SEQ ID NO:16:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: UNKNOWN (i i) MOLECULE TYPE:
        (A) DESCRIPTION: OLIGONUCLEOTIDE (i i i) HYPOTHETICAL: NO (i v) ANTI-SENSE: YES (v i) ORIGINAL SOURCE:
        (A) ORGANISM: HUMAN
        (C) INDIVIDUAL ISOLATE: IL-2R (x i) SEQUENCE DESCRIPTION:SEQ ID NO:16:

TCACCCTTCT CCAGTTGTC 19

(2) INFORMATION FOR SEQ ID NO:17:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (i i) MOLECULE TYPE:
        (A) DESCRIPTION: OLIGONUCLEOTIDE (i i i) HYPOTHETICAL: NO (i v) ANTI-SENSE: NO (v i) ORIGINAL SOURCE:
        (A) ORGANISM: HUMAN
        (C) INDIVIDUAL ISOLATE: IL-2R (x i) SEQUENCE DESCRIPTION:SEQ ID NO:17:

GCAGTCTATC AACTGCCAAC 20

(2) INFORMATION FOR SEQ ID NO:18:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (i i) MOLECULE TYPE:
        (A) DESCRIPTION: OLIGONUCLEOTIDE (i i i) HYPOTHETICAL: NO (i v) ANTI-SENSE: YES ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:18:

GACAGATATG TCCAGGTCAG                                                                                           20

( 2 ) INFORMATION FOR SEQ ID NO:19:

( i ) SEQUENCE CHARACTERISTICS:
                ( A ) LENGTH: 20
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: NO ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:19:

AAGGTTCTTT CCACCGGAAG                                                                                           20

( 2 ) INFORMATION FOR SEQ ID NO:20:

( i ) SEQUENCE CHARACTERISTICS:
                ( A ) LENGTH: 21
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: YES ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:20:

TGATTGTAAT TGGCCAGTGG C                                                                                         21

( 2 ) INFORMATION FOR SEQ ID NO:21:

( i ) SEQUENCE CHARACTERISTICS:
                ( A ) LENGTH: 20
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: NO ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:21:

ATGACAGAGG AAACGTGTGG                                                                                           20

( 2 ) INFORMATION FOR SEQ ID NO:22:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:22:

CAGGCACCAG ATCTCTGTAG        20

( 2 ) INFORMATION FOR SEQ ID NO:23:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:23:

ACAGCCACCC TTCTCACCAG        20

( 2 ) INFORMATION FOR SEQ ID NO:24:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:24:

GCAGCTGCAG GAATAAGAGG        20

( 2 ) INFORMATION FOR SEQ ID NO:25:

( i ) SEQUENCE CHARACTERISTICS:
        ( A ) LENGTH: 20
        ( B ) TYPE: NUCLEIC ACID
        ( C ) STRANDEDNESS: SINGLE ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: NO ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:25:

ATTACAGACA TGAGCCACCG                                               20

( 2 ) INFORMATION FOR SEQ ID NO:26:

( i ) SEQUENCE CHARACTERISTICS:
                ( A ) LENGTH: 19
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: YES ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:26:

CCCTCTCTCT TGGTCTCTG                                                19

( 2 ) INFORMATION FOR SEQ ID NO:27:

( i ) SEQUENCE CHARACTERISTICS:
                ( A ) LENGTH: 20
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: NO ( v i ) ORIGINAL SOURCE:
                ( A ) ORGANISM: HUMAN
                ( C ) INDIVIDUAL ISOLATE: IL-2R ( x i ) SEQUENCE DESCRIPTION:SEQ ID NO:27:

CTCCTTCTCA CCATCATTTC                                               20

( 2 ) INFORMATION FOR SEQ ID NO:28:

( i ) SEQUENCE CHARACTERISTICS:
                ( A ) LENGTH: 20
                ( B ) TYPE: NUCLEIC ACID
                ( C ) STRANDEDNESS: SINGLE
                ( D ) TOPOLOGY: UNKNOWN ( i i ) MOLECULE TYPE:
                ( A ) DESCRIPTION: OLIGONUCLEOTIDE ( i i i ) HYPOTHETICAL: NO ( i v ) ANTI-SENSE: YES (v i) ORIGINAL SOURCE:
        (A) ORGANISM: HUMAN
        (C) INDIVIDUAL ISOLATE: IL-2R (x i) SEQUENCE DESCRIPTION:SEQ ID NO:28:

CTTGGTCTCT GATCCAACCC                    20

(2) INFORMATION FOR SEQ ID NO:29:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: UNKNOWN (i i) MOLECULE TYPE:
        (A) DESCRIPTION: OLIGONUCLEOTIDE (i i i) HYPOTHETICAL: NO (i v) ANTI-SENSE: YES (v i) ORIGINAL SOURCE:
        (A) ORGANISM: HUMAN
        (C) INDIVIDUAL ISOLATE: IL-2R (x i) SEQUENCE DESCRIPTION:SEQ ID NO:29:

TCTGATCCAA CCCACCTCTT C                  21

(2) INFORMATION FOR SEQ ID NO:30:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (i i) MOLECULE TYPE:
        (A) DESCRIPTION: OLIGONUCLEOTIDE (i i i) HYPOTHETICAL: NO (i v) ANTI-SENSE: YES (v i) ORIGINAL SOURCE:
        (A) ORGANISM: HUMAN
        (C) INDIVIDUAL ISOLATE: IL-2R (x i) SEQUENCE DESCRIPTION:SEQ ID NO:30:

CAAAACACTG AACCTCTGGG                    20

(2) INFORMATION FOR SEQ ID NO:31:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (i i) MOLECULE TYPE:
        (A) DESCRIPTION: OLIGONUCLEOTIDE (i i i) HYPOTHETICAL: NO (i v) ANTI-SENSE: NO (v i) ORIGINAL SOURCE:
        (A) ORGANISM: HUMAN
        (C) INDIVIDUAL ISOLATE: IL-2R (x i) SEQUENCE DESCRIPTION:SEQ ID NO:31:

TAGGCTCTGG ATATCTGCAG                    20

( 2 ) INFORMATION FOR SEQ ID NO:32:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:32:

CTCTGTAGAC TCCAATGTCC        20

( 2 ) INFORMATION FOR SEQ ID NO:33:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:33:

CTGTTCCTCT TCCTTCCAAC        20

( 2 ) INFORMATION FOR SEQ ID NO:34:

( i ) SEQUENCE CHARACTERISTICS:
        ( A ) LENGTH: 18
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:34:

GACTCCAATG TCCCACAG        18

( 2 ) INFORMATION FOR SEQ ID NO:35:

( i ) SEQUENCE CHARACTERISTICS:
        ( A ) LENGTH: 20
        ( B ) TYPE: NUCLEIC ACID
        ( C ) STRANDEDNESS: SINGLE (D) TOPOLOGY: UNKNOWN (ii) MOLECULE TYPE:
                (A) DESCRIPTION: OLIGONUCLEOTIDE (iii) HYPOTHETICAL: NO (iv) ANTI-SENSE: YES (vi) ORIGINAL SOURCE:
                (A) ORGANISM: HUMAN
                (C) INDIVIDUAL ISOLATE: IL-2R (xi) SEQUENCE DESCRIPTION:SEQ ID NO:35:

AATGTCCCAC AGTATCCCTG                                                      20

(2) INFORMATION FOR SEQ ID NO:36:

(i) SEQUENCE CHARACTERISTICS:
                (A) LENGTH: 19
                (B) TYPE: NUCLEIC ACID
                (C) STRANDEDNESS: SINGLE
                (D) TOPOLOGY: UNKNOWN (ii) MOLECULE TYPE:
                (A) DESCRIPTION: OLIGONUCLEOTIDE (iii) HYPOTHETICAL: NO (iv) ANTI-SENSE: YES (vi) ORIGINAL SOURCE:
                (A) ORGANISM: HUMAN
                (C) INDIVIDUAL ISOLATE: IL-2R (xi) SEQUENCE DESCRIPTION:SEQ ID NO:36:

TTTGGTAGAG GTGGATCTC                                                       19

(2) INFORMATION FOR SEQ ID NO:37:

(i) SEQUENCE CHARACTERISTICS:
                (A) LENGTH: 20
                (B) TYPE: NUCLEIC ACID
                (C) STRANDEDNESS: SINGLE
                (D) TOPOLOGY: UNKNOWN (ii) MOLECULE TYPE:
                (A) DESCRIPTION: OLIGONUCLEOTIDE (iii) HYPOTHETICAL: NO (iv) ANTI-SENSE: NO (vi) ORIGINAL SOURCE:
                (A) ORGANISM: HUMAN
                (C) INDIVIDUAL ISOLATE: IL-2R (xi) SEQUENCE DESCRIPTION:SEQ ID NO:37:

ATTAGGGGCA CTACCTTCAG                                                      20

(2) INFORMATION FOR SEQ ID NO:38:

(i) SEQUENCE CHARACTERISTICS:
                (A) LENGTH: 20
                (B) TYPE: NUCLEIC ACID
                (C) STRANDEDNESS: SINGLE
                (D) TOPOLOGY: UNKNOWN (ii) MOLECULE TYPE:
                (A) DESCRIPTION: OLIGONUCLEOTIDE (iii) HYPOTHETICAL: NO (iv) ANTI-SENSE: YES ( v i ) ORIGINAL SOURCE:
   ( A ) ORGANISM: HUMAN
   ( C ) INDIVIDUAL ISOLATE: IL-2R ( x i ) SEQUENCE DESCRIPTION:SEQ ID NO:38:

AGGTCCTTCT ATCTGTCTGG                      20

( 2 ) INFORMATION FOR SEQ ID NO:39:

( i ) SEQUENCE CHARACTERISTICS:
   ( A ) LENGTH: 20
   ( B ) TYPE: NUCLEIC ACID
   ( C ) STRANDEDNESS: SINGLE
   ( D ) TOPOLOGY: UNKNOWN ( i i ) MOLECULE TYPE:
   ( A ) DESCRIPTION: OLIGONUCLEOTIDE ( i i i ) HYPOTHETICAL: NO ( i v ) ANTI-SENSE: NO ( v i ) ORIGINAL SOURCE:
   ( A ) ORGANISM: HUMAN
   ( C ) INDIVIDUAL ISOLATE: IL-2R ( x i ) SEQUENCE DESCRIPTION:SEQ ID NO:39:

ACCTTCAGGA TCCTGACTTG                      20

( 2 ) INFORMATION FOR SEQ ID NO:40:

( i ) SEQUENCE CHARACTERISTICS:
   ( A ) LENGTH: 20
   ( B ) TYPE: NUCLEIC ACID
   ( C ) STRANDEDNESS: SINGLE
   ( D ) TOPOLOGY: UNKNOWN ( i i ) MOLECULE TYPE:
   ( A ) DESCRIPTION: OLIGONUCLEOTIDE ( i i i ) HYPOTHETICAL: NO ( i v ) ANTI-SENSE: YES ( v i ) ORIGINAL SOURCE:
   ( A ) ORGANISM: HUMAN
   ( C ) INDIVIDUAL ISOLATE: IL-2R ( x i ) SEQUENCE DESCRIPTION:SEQ ID NO:40:

GTTGAATCCT TTAGCCCTAC                      20

( 2 ) INFORMATION FOR SEQ ID NO:41:

( i ) SEQUENCE CHARACTERISTICS:
   ( A ) LENGTH: 20
   ( B ) TYPE: NUCLEIC ACID
   ( C ) STRANDEDNESS: SINGLE
   ( D ) TOPOLOGY: UNKNOWN ( i i ) MOLECULE TYPE:
   ( A ) DESCRIPTION: OLIGONUCLEOTIDE ( i i i ) HYPOTHETICAL: NO ( i v ) ANTI-SENSE: YES ( v i ) ORIGINAL SOURCE:
   ( A ) ORGANISM: HUMAN
   ( C ) INDIVIDUAL ISOLATE: IL-2R ( x i ) SEQUENCE DESCRIPTION:SEQ ID NO:41:

ACTTTCTTGG CCTTAGCTGC                      20

( 2 ) INFORMATION FOR SEQ ID NO:42:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:42:

AGAATCTGTT GTTCCAGTTC                                                   20

( 2 ) INFORMATION FOR SEQ ID NO:43:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:43:

CAGTAGCAGA GATGACACTG                                                   20

( 2 ) INFORMATION FOR SEQ ID NO:44:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:44:

TAGACAGTGT GGAGAGATGG                                                   20

( 2 ) INFORMATION FOR SEQ ID NO:45:

( i ) SEQUENCE CHARACTERISTICS:
        ( A ) LENGTH: 20
        ( B ) TYPE: NUCLEIC ACID
        ( C ) STRANDEDNESS: SINGLE (D) TOPOLOGY: UNKNOWN (ii) MOLECULE TYPE:
(A) DESCRIPTION: OLIGONUCLEOTIDE (iii) HYPOTHETICAL: NO (iv) ANTI-SENSE: NO (vi) ORIGINAL SOURCE:
(A) ORGANISM: HUMAN
(C) INDIVIDUAL ISOLATE: IL-2R (xi) SEQUENCE DESCRIPTION:SEQ ID NO:45:

CTTCTCTCAT AGACACCCAC 20

(2) INFORMATION FOR SEQ ID NO:46:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (ii) MOLECULE TYPE:
(A) DESCRIPTION: OLIGONUCLEOTIDE (iii) HYPOTHETICAL: NO (iv) ANTI-SENSE: YES (vi) ORIGINAL SOURCE:
(A) ORGANISM: HUMAN
(C) INDIVIDUAL ISOLATE: IL-2R (xi) SEQUENCE DESCRIPTION:SEQ ID NO:46:

AGGGAAGTGG AGCAAAAGAC 20

(2) INFORMATION FOR SEQ ID NO:47:

(i) SEQUENCE CHARACTERISTICS:
(A) LENGTH: 21
(B) TYPE: NUCLEIC ACID
(C) STRANDEDNESS: SINGLE
(D) TOPOLOGY: UNKNOWN (ii) MOLECULE TYPE:
(A) DESCRIPTION: OLIGONUCLEOTIDE (iii) HYPOTHETICAL: NO (iv) ANTI-SENSE: YES (vi) ORIGINAL SOURCE:
(A) ORGANISM: HUMAN
(C) INDIVIDUAL ISOLATE: IL-2R (xi) SEQUENCE DESCRIPTION:SEQ ID NO:47:

AGCAAAAGAC AGTGGTGTTA G 21

(2) INFORMATION FOR SEQ ID NO:48:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (ii) MOLECULE TYPE:
(A) DESCRIPTION: OLIGONUCLEOTIDE (iii) HYPOTHETICAL: NO (iv) ANTI-SENSE: YES (v i) ORIGINAL SOURCE:
    (A) ORGANISM: HUMAN
    (C) INDIVIDUAL ISOLATE: IL-2R (x i) SEQUENCE DESCRIPTION:SEQ ID NO:48:

TCCGAACACG AAACGTGTAG    20

(2) INFORMATION FOR SEQ ID NO:49:

(i) SEQUENCE CHARACTERISTICS:
       (A) LENGTH: 20
       (B) TYPE: NUCLEIC ACID
       (C) STRANDEDNESS: SINGLE
       (D) TOPOLOGY: UNKNOWN (i i) MOLECULE TYPE:
       (A) DESCRIPTION: OLIGONUCLEOTIDE (i i i) HYPOTHETICAL: NO (i v) ANTI-SENSE: NO (v i) ORIGINAL SOURCE:
       (A) ORGANISM: HUMAN
       (C) INDIVIDUAL ISOLATE: IL-2R (x i) SEQUENCE DESCRIPTION:SEQ ID NO:49:

TGGAGGTAAT TGTTCCTGCC    20

(2) INFORMATION FOR SEQ ID NO:50:

(i) SEQUENCE CHARACTERISTICS:
       (A) LENGTH: 20
       (B) TYPE: NUCLEIC ACID
       (C) STRANDEDNESS: SINGLE
       (D) TOPOLOGY: UNKNOWN (i i) MOLECULE TYPE:
       (A) DESCRIPTION: OLIGONUCLEOTIDE (i i i) HYPOTHETICAL: NO (i v) ANTI-SENSE: YES (v i) ORIGINAL SOURCE:
       (A) ORGANISM: HUMAN
       (C) INDIVIDUAL ISOLATE: IL-2R (x i) SEQUENCE DESCRIPTION:SEQ ID NO:50:

CCAAACCCTC TTGGGTAATC    20

(2) INFORMATION FOR SEQ ID NO:51:

(i) SEQUENCE CHARACTERISTICS:
       (A) LENGTH: 20
       (B) TYPE: NUCLEIC ACID
       (C) STRANDEDNESS: SINGLE
       (D) TOPOLOGY: UNKNOWN (i i) MOLECULE TYPE:
       (A) DESCRIPTION: OLIGONUCLEOTIDE (i i i) HYPOTHETICAL: NO (i v) ANTI-SENSE: NO (v i) ORIGINAL SOURCE:
       (A) ORGANISM: HUMAN
       (C) INDIVIDUAL ISOLATE: IL-2R (x i) SEQUENCE DESCRIPTION:SEQ ID NO:51:

TCACAGGAGC TGTTGTGAGG    20

( 2 ) INFORMATION FOR SEQ ID NO:52:

( i ) SEQUENCE CHARACTERISTICS:
        ( A ) LENGTH: 21
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:52:

TACTGTCTCA TCCTTTACTC C         21

( 2 ) INFORMATION FOR SEQ ID NO:53:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:53:

CTATTGTCAG CTACCGTTCC         20

( 2 ) INFORMATION FOR SEQ ID NO:54:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:54:

GCTGATAATC AATCCCATGG         20

( 2 ) INFORMATION FOR SEQ ID NO:55:

( i ) SEQUENCE CHARACTERISTICS:
        ( A ) LENGTH: 20
        ( B ) TYPE: NUCLEIC ACID
        ( C ) STRANDEDNESS: SINGLE (D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: NO (v i) ORIGINAL SOURCE:
(A) ORGANISM: HUMAN
(C) INDIVIDUAL ISOLATE: IL-2R (x i) SEQUENCE DESCRIPTION:SEQ ID NO:55:

TATGGACAAC TGGAGAAGGG 20

(2) INFORMATION FOR SEQ ID NO:56:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: YES (v i) ORIGINAL SOURCE:
(A) ORGANISM: HUMAN
(C) INDIVIDUAL ISOLATE: IL-2R (x i) SEQUENCE DESCRIPTION:SEQ ID NO:56:

ACACTCTGTC TGTCTTGCTG 20

(2) INFORMATION FOR SEQ ID NO:57:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: NO (v i) ORIGINAL SOURCE:
(A) ORGANISM: HUMAN
(C) INDIVIDUAL ISOLATE: IL-2R (x i) SEQUENCE DESCRIPTION:SEQ ID NO:57:

TAACCTATGT GCTCCTGCTC 20

(2) INFORMATION FOR SEQ ID NO:58:

(i) SEQUENCE CHARACTERISTICS:
(A) LENGTH: 19
(B) TYPE: NUCLEIC ACID
(C) STRANDEDNESS: SINGLE
(D) TOPOLOGY: UNKNOWN (i i) MOLECULE TYPE:
(A) DESCRIPTION: OLIGONUCLEOTIDE (i i i) HYPOTHETICAL: NO (i v) ANTI-SENSE: YES ( v i ) ORIGINAL SOURCE:
    ( A ) ORGANISM: HUMAN
    ( C ) INDIVIDUAL ISOLATE: IL-2R ( x i ) SEQUENCE DESCRIPTION:SEQ ID NO:58:

TCTTGCTGGC AGGCAGTTG     19

( 2 ) INFORMATION FOR SEQ ID NO:59:

( i ) SEQUENCE CHARACTERISTICS:
    ( A ) LENGTH: 20
    ( B ) TYPE: NUCLEIC ACID
    ( C ) STRANDEDNESS: SINGLE
    ( D ) TOPOLOGY: UNKNOWN ( i i ) MOLECULE TYPE:
    ( A ) DESCRIPTION: OLIGONUCLEOTIDE ( i i i ) HYPOTHETICAL: NO ( i v ) ANTI-SENSE: YES ( v i ) ORIGINAL SOURCE:
    ( A ) ORGANISM: HUMAN
    ( C ) INDIVIDUAL ISOLATE: IL-2R ( x i ) SEQUENCE DESCRIPTION:SEQ ID NO:59:

GTTGGCAGTT GATAGACTGC     20

( 2 ) INFORMATION FOR SEQ ID NO:60:

( i ) SEQUENCE CHARACTERISTICS:
    ( A ) LENGTH: 20
    ( B ) TYPE: NUCLEIC ACID
    ( C ) STRANDEDNESS: SINGLE
    ( D ) TOPOLOGY: UNKNOWN ( i i ) MOLECULE TYPE:
    ( A ) DESCRIPTION: OLIGONUCLEOTIDE ( i i i ) HYPOTHETICAL: NO ( i v ) ANTI-SENSE: NO ( v i ) ORIGINAL SOURCE:
    ( A ) ORGANISM: HUMAN
    ( C ) INDIVIDUAL ISOLATE: IL-2R ( x i ) SEQUENCE DESCRIPTION:SEQ ID NO:60:

TACTCCTTTG GACAGAGCTC     20

( 2 ) INFORMATION FOR SEQ ID NO:61:

( i ) SEQUENCE CHARACTERISTICS:
    ( A ) LENGTH: 20
    ( B ) TYPE: NUCLEIC ACID
    ( C ) STRANDEDNESS: SINGLE
    ( D ) TOPOLOGY: UNKNOWN ( i i ) MOLECULE TYPE:
    ( A ) DESCRIPTION: OLIGONUCLEOTIDE ( i i i ) HYPOTHETICAL: NO ( i v ) ANTI-SENSE: YES ( v i ) ORIGINAL SOURCE:
    ( A ) ORGANISM: HUMAN
    ( C ) INDIVIDUAL ISOLATE: IL-2R ( x i ) SEQUENCE DESCRIPTION:SEQ ID NO:61:

TTCCAAATCA GCCACAGTGG     20

( 2 ) INFORMATION FOR SEQ ID NO:62:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:62:

CTGACCTGGA CATATCTGTC 20

( 2 ) INFORMATION FOR SEQ ID NO:63:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:63:

TATGAGACGC AGGTGGGTTG 20

( 2 ) INFORMATION FOR SEQ ID NO:64:

( i ) SEQUENCE CHARACTERISTICS:
        ( A ) LENGTH: 22
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: YES ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:64:

GGAAAGTTAG TACCACTTAG GG 22

( 2 ) INFORMATION FOR SEQ ID NO:65:

( i ) SEQUENCE CHARACTERISTICS:
        ( A ) LENGTH: 19
        ( B ) TYPE: NUCLEIC ACID
        ( C ) STRANDEDNESS: SINGLE ( D ) TOPOLOGY: UNKNOWN ( i i ) MOLECULE TYPE:
            ( A ) DESCRIPTION: OLIGONUCLEOTIDE ( i i i ) HYPOTHETICAL: NO ( i v ) ANTI-SENSE: YES ( v i ) ORIGINAL SOURCE:
            ( A ) ORGANISM: HUMAN
            ( C ) INDIVIDUAL ISOLATE: IL-2R ( x i ) SEQUENCE DESCRIPTION:SEQ ID NO:65:

AATCTCACTG ACGAGGCAG                                                19

( 2 ) INFORMATION FOR SEQ ID NO:66:

( i ) SEQUENCE CHARACTERISTICS:
            ( A ) LENGTH: 22
            ( B ) TYPE: NUCLEIC ACID
            ( C ) STRANDEDNESS: SINGLE
            ( D ) TOPOLOGY: UNKNOWN ( i i ) MOLECULE TYPE:
            ( A ) DESCRIPTION: OLIGONUCLEOTIDE ( i i i ) HYPOTHETICAL: NO ( i v ) ANTI-SENSE: YES ( v i ) ORIGINAL SOURCE:
            ( A ) ORGANISM: HUMAN
            ( C ) INDIVIDUAL ISOLATE: IL-2R ( x i ) SEQUENCE DESCRIPTION:SEQ ID NO:66:

GATGGGAAGC TTGAAGCTAG TA                                            22

( 2 ) INFORMATION FOR SEQ ID NO:67:

( i ) SEQUENCE CHARACTERISTICS:
            ( A ) LENGTH: 31
            ( B ) TYPE: NUCLEIC ACID
            ( C ) STRANDEDNESS: SINGLE
            ( D ) TOPOLOGY: UNKNOWN ( i i ) MOLECULE TYPE:
            ( A ) DESCRIPTION: OLIGONUCLEOTIDE ( i i i ) HYPOTHETICAL: NO ( i v ) ANTI-SENSE: YES ( v i ) ORIGINAL SOURCE:
            ( A ) ORGANISM: HUMAN
            ( C ) INDIVIDUAL ISOLATE: IL-2R ( x i ) SEQUENCE DESCRIPTION:SEQ ID NO:67:

GTACTAAAGC TTGGCGCTTG CTCTTCATTC C                                  31

( 2 ) INFORMATION FOR SEQ ID NO:68:

( i ) SEQUENCE CHARACTERISTICS:
            ( A ) LENGTH: 1451
            ( B ) TYPE: NUCLEIC ACID
            ( C ) STRANDEDNESS: SINGLE
            ( D ) TOPOLOGY: UNKNOWN ( i i ) MOLECULE TYPE:
            ( A ) DESCRIPTION: OLIGONUCLEOTIDE ( i i i ) HYPOTHETICAL: NO ( i v ) ANTI-SENSE: NO ( v i ) ORIGINAL SOURCE:
    ( A ) ORGANISM: HUMAN
    ( C ) INDIVIDUAL ISOLATE: IL-2R ( x i ) SEQUENCE DESCRIPTION:SEQ ID NO:68:

| | | | | |
|---|---|---|---|---|
| GAAGAGCAAG | CGCCATGTTG | AAGCCATCAT | TACCATTCAC | 40 |
| ATCCCTCTTA | TTCCTGCAGC | TGCCCCTGCT | GGGAGTGGGG | 80 |
| CTGAACACGA | CAATTCTGAC | GCCCAATGGG | AATGAAGACA | 120 |
| CCACAGCTGA | TTTCTTCCTG | ACCACTATGC | CCACTGACTC | 160 |
| CCTCAGTGTT | TCCACTCTGC | CCCTCCCAGA | GGTTCAGTGT | 200 |
| TTTGTGTTCA | ATGTCGAGTA | CATGAATTGC | ACTTGGAACA | 240 |
| GCAGCTCTGA | GCCCCAGCCT | ACCAACCTCA | CTCTGCATTA | 280 |
| TTGGTACAAG | AACTCGGATA | ATGATAAAGT | CCAGAAGTGC | 320 |
| AGCCACTATC | TATTCTCTGA | AGAAATCACT | TCTGGCTGTC | 360 |
| AGTTGCAAAA | AAAGGAGATC | CACCTCTACC | AAACATTTGT | 400 |
| TGTTCAGCTC | CAGGACCCAC | GGGAACCCAG | GAGACAGGCC | 440 |
| ACACAGATGC | TAAAACTGCA | GAATCTGGTG | ATCCCCTGGG | 480 |
| CTCCAGAGAA | CCTAACACTT | CACAAACTGA | GTGAATCCCA | 520 |
| GCTAGAACTG | AACTGGAACA | ACAGATTCTT | GAACCACTGT | 560 |
| TTGGAGCACT | TGGTGCAGTA | CCGGACTGAC | TGGGACCACA | 600 |
| GCTGGACTGA | ACAATCAGTG | GATTATAGAC | ATAAGTTCTC | 640 |
| CTTGCCTAGT | GTGGATGGGC | AGAAACGCTA | CACGTTTCGT | 680 |
| GTTCGGAGCC | GCTTTAACCC | ACTCTGTGGA | AGTGCTCAGC | 720 |
| ATTGGAGTGA | ATGGAGCCAC | CCAATCCACT | GGGGGAGCAA | 760 |
| TACTTCAAAA | GAGAATCCTT | TCCTGTTTGC | ATTGGAAGCC | 800 |
| GTGGTTATCT | CTGTTGGCTC | CATGGGATTG | ATTATCAGCC | 840 |
| TTCTCTGTGT | GTATTTCTGG | CTGGAACGGA | CGATGCCCCG | 880 |
| AATTCCCACC | CTGAAGAACC | TAGAGGATCT | TGTTACTGAA | 920 |
| TACCACGGGA | ACTTTTCGGC | CTGGAGTGGT | GTGTCTAAGG | 960 |
| GACTGGCTGA | GAGTCTGCAG | CCAGACTACA | GTGAACGACT | 1000 |
| CTGCCTCGTC | AGTGAGATTC | CCCCAAAAGG | AGGGGCCCTT | 1040 |
| GGGGAGGGGC | CTGGGGCCTC | CCCATGCAAC | CAGCATAGCC | 1080 |
| CCTACTGGGC | CCCCCCATGT | TACACCCTAA | AGCCTGAAAC | 1120 |
| CTGAACCCCA | ATCCTCTGAC | AGAAGAACCC | CAGGGTCCTG | 1160 |
| TAGCCCTAAG | TGGTACTAAC | TTTCCTTCAT | TCAACCCACC | 1200 |
| TGCGTCTCAT | ACTCACCTCA | CCCCACTGTG | GCTGATTTGG | 1240 |
| AATTTGTGC | CCCCATGTAA | GCACCCCTTC | ATTTGGCATT | 1280 |
| CCCCACTTGA | GAATTACCCT | TTTGCCCCGA | ACATGTTTTT | 1320 |
| CTTCTCCCTC | AGTCTGGCCC | TTCCTTTTCG | CAGGATTCTT | 1360 |
| CCTCCCTCCC | TCTTTCCCTC | CCTTCCTCTT | TCCATCTACC | 1400 |
| CTCCGATTGT | TCCTGAACCG | ATGAGAAATA | AAGTTTCTGT | 1440 |
| TGATAATCAT | C | | | 1451 |

( 2 ) INFORMATION FOR SEQ ID NO:69:

( i ) SEQUENCE CHARACTERISTICS:
        ( A ) LENGTH: 326
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:69:

| | | | | |
|---|---|---|---|---|
| CACCAGGATT | ACAGACATGA | GCCACCGTGC | TTGGCCTCCT | 40 |
| CCTTCTCACC | ATCATTTCTC | TTTCCCTCCC | TGCCTTCATT | 80 |
| TTCTCCCCAA | TCTAGATTTC | TTCCTGACCA | CTATGCCCAC | 120 |
| TGACTCCCTC | AGTGTTTCCA | CTCTACCCCT | CCCAGAGGTT | 160 |
| CAGTGTTTTG | TGTTCAATGT | CGAGTACATG | AATTGCACTT | 200 |
| GGAACAGCAG | CTCTGAGCCC | CAGCCTACCA | ACCTCACTCT | 240 |
| GCATTATTGG | TATGAGAAGG | GACGAGGGGG | AGGGGATGAA | 280 |
| GAAGAGGTGG | GTTGGATCAG | AGACCAAGAG | AGAGGGTAGC | 320 |
| AAGTCT | | | | 326 |

( 2 ) INFORMATION FOR SEQ ID NO:70:

( i ) SEQUENCE CHARACTERISTICS:
        ( A ) LENGTH: 513
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:70:

| | | | | |
|---|---|---|---|---|
| AGAGAGAGGG | TAGCAAGTCT | CCCAGGTACC | CCACTGTTTT | 40 |
| CTCCTGGGGA | AGTCATAAGT | CGGTTGAGGG | GAGATGAGGC | 80 |
| TAGGCTCTGG | ATATCTGCAG | TACCCAGATT | GGCCCCACTG | 120 |
| TTCCTCTTCC | TTCCAACCTT | TCTCCTCTAG | GTACAAGAAC | 160 |
| TCGGATAATG | ATAAAGTCCA | GAAGTGCAGC | CACTATCTAT | 200 |
| TCTCTGAAGA | AATCACTTCT | GGCTGTCAGT | TGCAAAAAAA | 240 |
| GGAGATCCAC | CTCTACCAAA | CATTTGTTGT | TCAGCTCCAG | 280 |
| GACCCACGGG | AACCCAGGAG | ACAGGCCACA | CAGATGCTAA | 320 |
| AACTGCAGAA | TCTGGGTAAT | TTGGAAAGAA | AGGGTCAAGA | 360 |

| | | | | |
|---|---|---|---|---|
| GACCAGGGAT | ACTGTGGGAC | ATTGGAGTCT | ACAGAGTAGT | 400 |
| GTTCTTTTAT | CATAAGGGTA | CATGGGCAGA | AAAGAGGAGG | 440 |
| TAGGGGATCA | TGATGGGAAG | GGAGGAGGTA | TTAGGGGCAC | 480 |
| TACCTTCAGG | ATCCTGACTT | GTCTTAGGCC | AGG | 513 |

( 2 ) INFORMATION FOR SEQ ID NO:71:

( i ) SEQUENCE CHARACTERISTICS:
        ( A ) LENGTH: 907
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:71:

| | | | | |
|---|---|---|---|---|
| AAGCTTGAAG | CTAGTATTGT | TGTTCCTCCA | TTTCTAGAAT | 40 |
| ATTTTTGTAT | TATAAGTCAC | ACTTCCTCGC | CAGTCTCAAC | 80 |
| AGGGACCCAG | CTCAGGCAGC | AGCTAAGGGT | GGGTATTCTG | 120 |
| GTTTGGATTA | GATCAGAGGA | AAGACAGCTG | TATATGTGCC | 160 |
| CACAGGAGCC | AAGACGGTAT | TTTCCATCCT | CCCAAAACAG | 200 |
| GTATGAGCTT | TGACAGAGAT | TTAAGGGTGA | CCAAGTCAAG | 240 |
| GAAGAGGCAT | GGCATAGAAC | GGTGATGTCG | GGGGTGGGGG | 280 |
| GTTCAGAACT | TCCATTATAG | AAGGTAATGA | TTTAGAGGAG | 320 |
| AAGGTGGTTG | AGAATGGTGC | TAGTGGTAGT | GAACAGATCC | 360 |
| TTCCCAGGAT | CTAGGTGGGC | TGAGGATTTT | TGAGTCTGTG | 400 |
| ACACTATTGT | ATATCCAGCT | TTAGTTTCTG | TTTACCACCT | 440 |
| TACAGCAGCA | CCTAATCTCC | TAGAGGACTT | AGCCCGTGTC | 480 |
| ACACAGCACA | TATTTGCCAC | ACCCTCTGTA | AAGCCCTGGT | 520 |
| TATAAGGTTC | TTTCCACCGG | AAGCTATGAC | AGAGGAAACG | 560 |
| TGTGGGTGGG | GAGGGGTAGT | GGGTGAGGGA | CCCAGGTTCC | 600 |
| TGACACAGAC | AGACTACACC | CAGGGAATGA | AGAGCAAGCG | 640 |
| CCATGTTGAA | GCCATCATTA | CCATTCACAT | CCCTCTTATT | 680 |
| CCTGCAGCTG | CCCCTGCTGG | GAGTGGGGCT | GAACACGACA | 720 |
| ATTCTGACGC | CCAATGGGAA | TGAAGACACC | ACAGCTGGTG | 760 |
| GGAAATCTGG | GACTGGAGGG | GGCTGGTGAG | AAGGGTGGCT | 800 |
| GTGGGAAGGG | GCCGTACAGA | GATCTGGTGC | CTGCCACTGG | 840 |
| CCATTACAAT | CATGTGGGCA | GAATTGAAAA | GTGGAGTGGG | 880 |
| AAGGGCAAGG | GGGAGGGTTC | CCTCCCT | | 907 |

( 2 ) INFORMATION FOR SEQ ID NO:72:

( i ) SEQUENCE CHARACTERISTICS:
  ( A ) LENGTH: 423
  ( B ) TYPE: NUCLEIC ACID
  ( C ) STRANDEDNESS: SINGLE
  ( D ) TOPOLOGY: UNKNOWN ( i i ) MOLECULE TYPE:
  ( A ) DESCRIPTION: OLIGONUCLEOTIDE ( i i i ) HYPOTHETICAL: NO ( i v ) ANTI-SENSE: NO ( v i ) ORIGINAL SOURCE:
  ( A ) ORGANISM: HUMAN
  ( C ) INDIVIDUAL ISOLATE: IL-2R ( x i ) SEQUENCE DESCRIPTION:SEQ ID NO:72:

| | | | | |
|---|---|---|---|---|
| GGAGGTATTA | GGGGCACTAC | CTTCAGGATC | CTGACTTGTC | 40 |
| TAGGCCAGGG | KAATGACCAC | ATATGCACAC | ATATCTCCAG | 80 |
| TGATCCCCTG | GGCTCCAGAG | AACCTAACAC | TTCACAAACT | 120 |
| GAGTGAATCC | CAGCTAGAAC | TGAACTGGAA | CAACAGATTC | 160 |
| TTGAACCACT | GTTTGGAGCA | CTTGGTGCAG | TACCGGACTG | 200 |
| ACTGGGACCA | CAGCTGGACT | GTGAGTGACT | AGGGACGTGA | 240 |
| ATGTAGCAGC | TAAGGCCAAG | AAAGTAGGGC | TAAAGGATTC | 280 |
| AACCAGACAG | ATAGAAGGAC | CTAATATCAA | GCTCCTGTTC | 320 |
| TGCNTCCCAG | CTTCTCTGCT | CACCCCCTAC | CCTCCCTCCT | 360 |
| CCAACTCCTT | NNCCCCCTAT | TTTCTCCAGT | GAGTTTCTT | 400 |
| TTTTTCTTTT | CTTTTCTTTC | TTT | | 423 |

( 2 ) INFORMATION FOR SEQ ID NO:73:

( i ) SEQUENCE CHARACTERISTICS:
    ( A ) LENGTH: 490
    ( B ) TYPE: NUCLEIC ACID
    ( C ) STRANDEDNESS: SINGLE
    ( D ) TOPOLOGY: UNKNOWN ( i i ) MOLECULE TYPE:
    ( A ) DESCRIPTION: OLIGONUCLEOTIDE ( i i i ) HYPOTHETICAL: NO ( i v ) ANTI-SENSE: NO ( v i ) ORIGINAL SOURCE:
    ( A ) ORGANISM: HUMAN
    ( C ) INDIVIDUAL ISOLATE: IL-2R ( x i ) SEQUENCE DESCRIPTION:SEQ ID NO:73:

| | | | | |
|---|---|---|---|---|
| GTAGTCAAGA | GATGAGAGAG | AAACTGGGCA | GTAGCAGAGA | 40 |
| TGACACTGGT | GGGTGTTCAG | GAGTATGTTT | TAATTCTCCC | 80 |
| TTCTCTCATA | GACACCCACT | TTCCCTCATC | CTCTTTCTCC | 120 |
| TCAAGGAACA | ATCAGTGGAT | TATAGACATA | AGTTCTCCTT | 160 |
| GCCTAGTGTG | GATGGGCAGA | AACGCTACAC | GTTTCGTGTT | 200 |
| CGGAGCCGCT | TTAACCCACT | CTGTGGAAGT | GCTCAGCATT | 240 |
| GGAGTGAATG | GAGCCACCCA | ATCCACTGGG | GGAGCAATAC | 280 |
| TTCAAAAGGT | AAAATGGGCC | CACATNACCC | AATCCATGAG | 320 |
| CCCAACACCC | CAGCCTTTCT | AACACCACTG | TCTTTTGCTC | 360 |

| CACTTCCCTG | TCACTAAAGC | CCCTAAACTT | GGTGCCCCAT | 400 |
| CTCTCCACAC | TGTCTAACCC | CAACCTCTAG | AAATCAAGGT | 440 |
| TTTTCTGTGT | AGGGTTGGGT | TAGCGTGTTG | TTAGAGTAGG | 480 |
| GGAGTGGATT | | | | 490 |

( 2 ) INFORMATION FOR SEQ ID NO:74:

( i ) SEQUENCE CHARACTERISTICS:
            ( A ) LENGTH: 448
            ( B ) TYPE: NUCLEIC ACID
            ( C ) STRANDEDNESS: SINGLE
            ( D ) TOPOLOGY: UNKNOWN ( i i ) MOLECULE TYPE:
            ( A ) DESCRIPTION: OLIGONUCLEOTIDE ( i i i ) HYPOTHETICAL: NO ( i v ) ANTI-SENSE: NO ( v i ) ORIGINAL SOURCE:
            ( A ) ORGANISM: HUMAN
            ( C ) INDIVIDUAL ISOLATE: IL-2R ( x i ) SEQUENCE DESCRIPTION:SEQ ID NO:74:

| CCACATCCCT | AACTCTTGGA | TTATGTTTCC | TAAGATGTAA | 40 |
| GATGGAGGTA | ATTGTTCCTG | CCTCACAGGA | GCTGTTGTGA | 80 |
| GGATTAAACA | GAGNGTATGT | CTTTAGCGCG | GTGCCTGGCA | 120 |
| CCAGTGCCTG | GCANGTAGTA | GGGGCACAAC | AAATATAAGG | 160 |
| TCCACTTTGC | TTTTCTTTTT | TCTATAGAGA | ATCCTTTCCT | 200 |
| GTTTGCATTG | GAAGCCGTGG | TTATCTCTGT | TGGCTCCATG | 240 |
| GGATTGATTA | TCAGCCTTCT | CTGTGTGTAT | TTCTGGCTGG | 280 |
| AACGGTGAGA | TTTGGAGAAG | CCCAGAAAAA | TGAGGGGAAC | 320 |
| GGTAGCTGAC | AATAGCAGAG | GAGGGTTTTG | CAGGGTCTTT | 360 |
| AGGAGTAAAG | GATGAGACAG | TAAGTAATGA | GAGATTACCC | 400 |
| AAGAGGGTTT | GGTGATGGAA | GGAAGCCACA | GGCACAGAGA | 440 |
| ACACAGAA | | | | 448 |

( 2 ) INFORMATION FOR SEQ ID NO:75:

( i ) SEQUENCE CHARACTERISTICS:
            ( A ) LENGTH: 216
            ( B ) TYPE: NUCLEIC ACID
            ( C ) STRANDEDNESS: SINGLE
            ( D ) TOPOLOGY: UNKNOWN ( i i ) MOLECULE TYPE:
            ( A ) DESCRIPTION: OLIGONUCLEOTIDE ( i i i ) HYPOTHETICAL: NO ( i v ) ANTI-SENSE: NO ( v i ) ORIGINAL SOURCE:
            ( A ) ORGANISM: HUMAN
            ( C ) INDIVIDUAL ISOLATE: IL-2R ( x i ) SEQUENCE DESCRIPTION:SEQ ID NO:75:

| ATATGGACAA | CTGGAGAAGG | GTGATAAAAA | AGCTTTAACC | 40 |
| TATGTGCTCC | TGCTCCCTCT | TTCTCCCCTG | TCAGGACGAT | 80 |

```
GCCCCGAATT  CCCACCCTGA  AGAACCTAGA  GGATCTTGTT                               120

ACTGAATACC  ACGGGAACTT  TTCGGTGAGA  ACGCTGTCAT                               160

AAGCATGCTG  CAGTCTATCA  ACTGCCAACT  GCCTGCCAGC                               200

AAGACAGACA  GAGTGT                                                           216
```

( 2 ) INFORMATION FOR SEQ ID NO:76:

( i ) SEQUENCE CHARACTERISTICS:
        ( A ) LENGTH: 301
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( C ) INDIVIDUAL ISOLATE: IL-2R ( x i ) SEQUENCE DESCRIPTION:SEQ ID NO:76:

```
GTACTCCTTT  GGACAGAGCT  CGGTCTTTTA  CTTCCTGCCC                                40

CTAATTGACC  CCTGACCTGG  ACATATCTGT  CTTTAGGCCT                                80

GGAGTGGTGT  GTCTAAGGGA  CTGGCTGAGA  GTCTGCAGCC                               120

AGACTACAGT  GAACGACTCT  GCCTCGTCAG  TGAGATTCCC                               160

CCAAAAGGAG  GGGCCCTTGG  GGAGGGGCCT  GGGGCCTCCC                               200

CATGCAACCA  GCATAGCCCC  TACTGGGCCC  CCCCATGTTA                               240

CACCCTAAAG  CCTGAAACCT  GAACCCCAAT  CCTCTGACAG                               280

AAGAACCCCA  GGGTCCTGTA  G                                                    301
```